United States Patent [19]
Seitz et al.

[11] Patent Number: 6,149,595
[45] Date of Patent: Nov. 21, 2000

[54] NONINVASIVE APPARATUS AND METHOD FOR THE DETERMINATION OF CARDIAC VALVE FUNCTION

[76] Inventors: Walter S. Seitz, 38 Panoramic Way, Berkeley, Calif. 94704; Steven P. Olsen, 720 S. Fielding Ave., Tampa, Fla. 33606

[21] Appl. No.: 09/108,769

[22] Filed: Jul. 2, 1998

[51] Int. Cl.[7] .................................................... A61B 8/00
[52] U.S. Cl. ............................................ 600/438; 600/455
[58] Field of Search .................................. 600/453, 454, 600/455, 437, 436, 451

[56] References Cited

U.S. PATENT DOCUMENTS 5,701,898 12/1997 Adam et al. ............................ 600/447

*Primary Examiner*—Marvin M. Lateef
*Assistant Examiner*—Maulin Patel
*Attorney, Agent, or Firm*—Jacqueline E. Hartt, P.A.

[57] ABSTRACT

A method and device for determining a plurality of cardiovascular parameters are described, wherein the parameters are determined from noninvasively obtained data, thereby obviating the need for invasive procedures such as cardiac catheterization. These determinations are enabled by incorporating fluid dynamics and thermodynamics equations with noninvasively obtained mechanical cardiac event data to estimate a desired cardiovascular parameter. Exemplary parameters obtainable with the method and device include aortic and mitral valve areas, cardiac left ventricular stroke volume, and aortic and mitral valve pressure gradients.

44 Claims, 6 Drawing Sheets

NONINVASIVE APPARATUS AND METHOD FOR THE DETERMINATION OF CARDIAC VALVE FUNCTION

BACKGROUND OF THE INVENTION

1. Field of the Invention

The present invention relates to apparatus and methods for the measurement of physiological functions, and, more particularly, to noninvasive apparatus and methods for the measurement of cardiac valve function.

2. Description of Related Art

Background on Cardiovascular Function Assessment Techniques

The cardiac cycle in a human heart is a well-studied phenomenon. As shown in FIG. 1 (Guyton, *Basic Human Physiology*, W.B. Saunders Co., Philadelphia, Pa., 1971), pressure, volumetric, electrical, and audible events can be correlated with the stages of the cardiac cycle.

Electrocardiograms (EKGs) detect the electrical potentials generated in the heart, but their interpretation is largely empirical, as the phenomena the peaks represent are not wholly understood, and diagnoses are primarily made via pattern matching techniques against known normal and disease states. Some myopathies that can be detected with an EKG are ventricular hypertrophy, bundle branch blocks, and fibrillation. However, such problems as valvular stenosis and regurgitation cannot be detected with an EKG, nor can transvalvular pressure gradients be assessed.

Cardiac catheterization is a technique that is used to measure blood pressure in various areas of the heart, as well as blood pumping rate and blood chemistry analysis. This procedure, however, has a nontrivial risk associated with it, even in relatively healthy patients, and infants and heart transplant patients are typically not candidates.

Echocardiographic techniques, including Doppler echocardiography, utilizes returned ultrasound pulses to map a graphic image of the heart and blood vessels, yielding information on the size, shape, and motion of the heart chambers and great vessels and the motion of the heart valves. It has recently been found that this method can compare favorably with cardiac catheterization in making assessments of cardiac hemodynamics in patients with cardiac disease (Dobaghi et al., *Am. J. Cardiol.* 76, 392, 1995; Nishimura and Tajik, *Prog. Cardiovasc. Dis.* 36, 309, 1994).

Esophageal echocardiography, in which a tube is placed down the patient's throat for visualizing the back of the heart, can detect a valve leakage, but this technique is expensive and uncomfortable, and requires great expertise to administer.

Heart sounds, which have been monitored in a gross manner via auscultation for hundreds of years, are representative of the vibration of the walls of the heart and major vessels around the heart caused by closure of the valves. The phonocardiogram is a recording of amplified low-frequency heart sounds detected by a microphone placed on the patient's chest. Abnormalities such as mitral and aortic stenosis, mitral and aortic regurgitation, and patent ductus arteriosus can be detected with this noninvasive technique.

Value Area Assessment Techniques

As early as the 1930s methods for obtaining sufficient hemodynamic information for the assessment of valvular stenosis through the application of hydraulic principles were becoming routinely available. However, it was not until 1951 that Gorlin and Gorlin published an orifice formula based upon hydraulic principles using information derived from cardiac catheterization.

The work of Gorlin and Gorlin represented a major advance in the diagnosis of stenotic valvular cardiac disease through the ability to reproducibly quantify the degree of stenosis in terms of valvular area. While this method has become almost universally accepted as the standard for assessing valvular stenosis, it does subject the patient to the highly invasive procedure of cardiac catheterization. It would be rewarding both from the point of view of improved patient care and evaluation and in the further understanding of cardiac mechanics if a method were developed that used diagnostic parameters of a less invasive nature than is the current practice.

The principal hemodynamic manifestations of a significant degree of aortic stenosis include an increased left ventricular pressure, "a" waves in the left atrial pressure pulse, an abnormally large systolic aortic valve pressure gradient whose value depends on the forward systolic flow rate, central aortic pressure pulse abnormalities, a prolonged systolic ejection interval and reduced cardiac output and coronary blood flow.

All these measurable manifestations of aortic stenosis are related to the degree of valvular stenosis but do not, in themselves, provide a quantification of the magnitude of the obstruction. Alterations in the fundamental hemodynamic variables of stroke volume, aortic valve pressure gradient and left ventricular ejection period are the basis for interpreting the principle clinical manifestations of aortic stenosis.

The hemodynamic foundation for the quantification of aortic stenosis from the fundamental variables was established by the investigations of Gorlin and Gorlin (1951). The principal result of these studies was the development of a hydraulic orifice formula that derived from a combination of two basic laws of fluid physics, the conservation of energy and conservation of mass. The resulting orifice formula determined the degree of outflow obstruction as specified by the aortic valve cross-sectional area. The valve area is precisely related to stroke volume, aortic valve pressure gradient, and systolic ejection time. Since the introduction of this hydraulic formula, it has become the most generally accepted diagnostic procedure for the accurate quantification of the degree of obstruction associated with aortic stenosis.

Despite the fundamental character of a diagnosis via the Gorlin formula, the highly invasive nature of the required hemodynamic measurements often necessitates diagnostic procedures of a less precise nature. Thus it would be desirable to provide a technique that would provide more precise data while at the same time presenting no risk to the patient.

Valve Pressure Gradient Assessment Techniques

Mitral valve disease is the result of a reaction on cardiac valve tissue of the body's defense mechanisms against a particular form of streptococcal infection known as rheumatic fever.

As a result of the relatively good public health measures in the industrialized world, mitral valve disease no longer represents the critical proportions that it assumes in the undeveloped world. Nevertheless, this disease still accounts for a significant health care concern. Statistics of the American Heart Association for 1978 indicate that approximately nine million adults have rheumatic heart disease in the United States, and the death rate due to this affliction is about 13,000 per year. Over one-half of all patients with rheumatic heart disease also develop mitral stenosis, and of this number 66% are women.

Of particular concern is heart disease in pregnancy. Heart disease of all classes occurs in approximately 1% of women of child-bearing age; however, rheumatic heart disease, particularly mitral stenosis, accounts for 90–95% of heart disease observed during pregnancy. Prenatal mortality rates are also strongly dependent on the degree of mitral stenosis. The infant mortality rate is approximately 12% for conditions of moderate maternal mitral stenosis and over 50% for severe mitral stenosis.

To minimize the maternal and fetal risks, it is recommended that pregnancies complicated by mitral stenosis be followed by serial observations of functional cardiac status. An important parameter of this abnormality is the capillary wedge pressure; however, it is clearly not feasible to perform serial catheterizations under these conditions.

Patients who have severe mitral valve disease are often given artificial valve replacements. While artificial valves alleviate the problem of stenosis, it is not uncommon for thrombi to form on the mechanical structures, producing systemic emboli and valve obstruction or re-stenosis. For this reason serial observation of the valve for possible malfunction and flow obstruction is important. Increased obstruction of the valve manifests itself by increased left atrial or capillary wedge pressure. A noninvasive estimate of pressure would be desirable to provide valuable diagnostic information for this class of patients.

Knowledge of the mitral valve area via the Gorlin and Gorlin method provides a quantitative measure of the severity of valve obstruction. Since the introduction of this method, the area computation has become a widely accepted diagnostic and investigative technique for cardiac valve obstructive disease. The fundamental variables required in the Gorlin formula are stroke volume, diastolic filling period (the duration that the valve is open), heart rate, and the pressure difference across the valve. Since cardiac echographic techniques now offer the possibility of determining stroke volume, heart rate, and diastolic filling period with good accuracy, it would be useful to have a method for estimating the pressure differential in an equally noninvasive manner. Doppler ultrasound will provide such a pressure estimate through application of the Bernoulli equation for the case of natural valves. The complex mechanical structure of many prosthetic valves precludes an accurate estimation of the blood jet velocity via Doppler methods, however.

It has proved possible to develop and verify an orifice equation that allows an expression of mitral valve area without explicit knowledge of the mitral valve gradient. This equation was validated using the original data of Gorlin and Gorlin and other published catheterization data. Furthermore, an effort to verify this equation using prospective echographic data has proved successful.

A significant method for assessment of the flow obstruction of aortic valves is to determine the pressure drop across the valve. The pressure drop across natural valves may be conveniently and noninvasively estimated by Doppler ultrasound velocity recordings with an approximate conversion to pressure via the Bernoulli equation. The more complex structure of prosthetic valves renders this technique less than meaningful. If stroke volume is known, an estimate of effective valve area may be obtained by the valve area formula.

Considerable effort has been directed to the assessment of left ventricular pressure, wall stress, and posterior wall thickness through ventricular dimension measurements. Furthermore, a relationship between aortic valve gradient and ventricular dimension has been suggested.

Current diagnostic techniques depend upon cardiac catheterization, Doppler ultrasound studies, or direct visualization of the mitral valve orifice by bi-dimensional echocardiography. It would thus be advantageous to provide a convenient and inexpensive screening test for natural and prosthetic mitral valve misfunction.

Assessment of Valvular Insufficiency

The pathogenesis of mitral and aortic regurgitation is extensive and varied. The conditions often present in association with, respectively, mitral/aortic stenosis or relative stenosis. While the etiology and symptoms are numerous, the one cardinal hemodynamic hallmark of this condition is a left ventricular stroke volume of greater magnitude than the forward stroke volume. This characteristic provides a basis for the quantitative assessment of the condition, through catheterization, angiography, or noninvasive methods. It would be useful to develop a noninvasive technique for estimating regurgitant fraction under conditions of pure or mixed mitral or aortic insufficiency.

Assessment of Stroke Volume

Numerous simplified mathematical formulations for the estimation of stroke volume from elementary echographic measurements have been proposed. One investigation analyzed eight recently proposed echographic formulae for stroke volume by comparing Fick principle and thermodilution determinations of cardiac output with M-mode echocardiographically derived values by simultaneous measurement of the appropriate echographic data. Comparison of the correlation coefficients for simultaneous stroke volume computations with values derived from cardiac catheterization has revealed that the Teichholz formula enjoyed the highest degree of correspondence with the invasive measurements and may be expected to correspond to invasive methods at a level of r=0.86 in the absence of wall motion asymmetries, hypokinesis, and arrhythmic states.

The cubic equation for cardiac volume represents the ventricular volume at any phase of the cardiac cycle in terms of a constant fraction ($\pi/3$) of the volume of a sphere. Teichholz et al. proposed an alternative model based upon the recognition that the ratio of the principal dimension of the ventricle does not remain constant from systole to diastole. This investigation analyzed the ventricular dimension in systole and diastole for 100 left ventricular configurations and permitted the derivation of a correction factor to the cubic equation that, on the average, accounted for the change in width-to-length ratio of the heart during contraction. Ventricular volume by this formula is represented by a single cardiac dimension measured perpendicular to the long axis of the heart at the level of the mitral valve. According to this model, cardiac volume is given as $V=7D^3/(2.4+D)$, where V is the cardiac volume in milliliters for any particular value of the ventricular dimension D measured in centimeters. The term $7/(2.4+D)$ may be viewed as a correction factor to the cubic formula, $V=D^3$, accounting for the changing D/L ratio during ventricular contraction, L being the apex-to-base length.

SUMMARY OF THE INVENTION

It is therefore an object of the present invention to provide a noninvasive apparatus and method for calculating cardiac valvular area and thereby assessing cardiac valvular stenosis.

It is an additional object to provide such an apparatus and method for assessing valve pressure gradients.

It is a further object to provide such an apparatus and method for assessing valvular insufficiency.

It is another object to develop a mathematical model of cardiac hemodynamics of sufficient generality to provide a framework for theoretical and experimental exploration of valvular flow dynamics with particular reference to the problem of specifying the effects of valvular orifice area.

It is yet an additional object to test the results of the predictions of this model against standard methods for assessing valvular orifice area.

It is yet a further object to apply the results of the theory of the noninvasive echocardiographic estimation of effective valvular orifice area.

It is also an object to provide a method for using noninvasively obtained cardiac data to calculate stroke volume and left ventricular volume.

It is another object to provide a noninvasive, convenient, and inexpensive method and device for screening for natural and prosthetic mitral valve misfunction.

These and other objects are achieved by the apparatus and method of the present invention, which include a method incorporating fluid dynamics and thermodynamics equations and noninvasive mechanical cardiac event data to estimate a desired cardiovascular parameter.

A first embodiment comprises a noninvasive method for measuring an area of a cardiac valve of a patient. The method comprises the steps of noninvasively measuring a plurality of mechanical cardiac parameters of the patient and calculating a cardiac valve area with the use of the measured cardiac parameters.

For the case of noninvasively measuring a cardiac valve area, the measuring step comprises measuring a heart rate and a stroke volume of the patient. When the cardiac valve desired to be measured is a mitral valve, the measuring step further comprises measuring a diastolic filling period of the patient. When the cardiac valve desired to be measured is an aortic valve, the measuring step further comprises measuring a systolic ejection period of the patient.

A second embodiment comprises noninvasively measuring a cardiac left ventricular stroke volume of a patient. The method comprises the steps of measuring an end diastolic dimension and an end systolic dimension and calculating the stroke volume therefrom.

A third embodiment comprises a noninvasive method for calculating a mitral valve pressure gradient of a patient. This method comprises the steps of noninvasively measuring a heart rate and a left ventricular diastolic filling period of the patient. From these measurements the mitral valve pressure gradient may be A fourth embodiment comprises a noninvasive method of measuring an aortic valve pressure gradient of a patient. This method comprises the steps of noninvasively measuring a left ventricular wall thickness and a left ventricular end-diastolic dimension of the patient. From these data can be calculated the aortic valve pressure gradient.

The features that characterize the invention, both as to organization and method of operation, together with further objects and advantages thereof, will be better understood from the following description used in conjunction with the accompanying drawing. It is to be expressly understood that the drawing is for the purpose of illustration and description and is not intended as a definition of the limits of the invention. These and other objects attained, and advantages offered, by the present invention will become more fully apparent as the description that now follows is read in conjunction with the accompanying drawing.

DETAILED DESCRIPTION OF THE PREFERRED EMBODIMENTS

Figure 1:
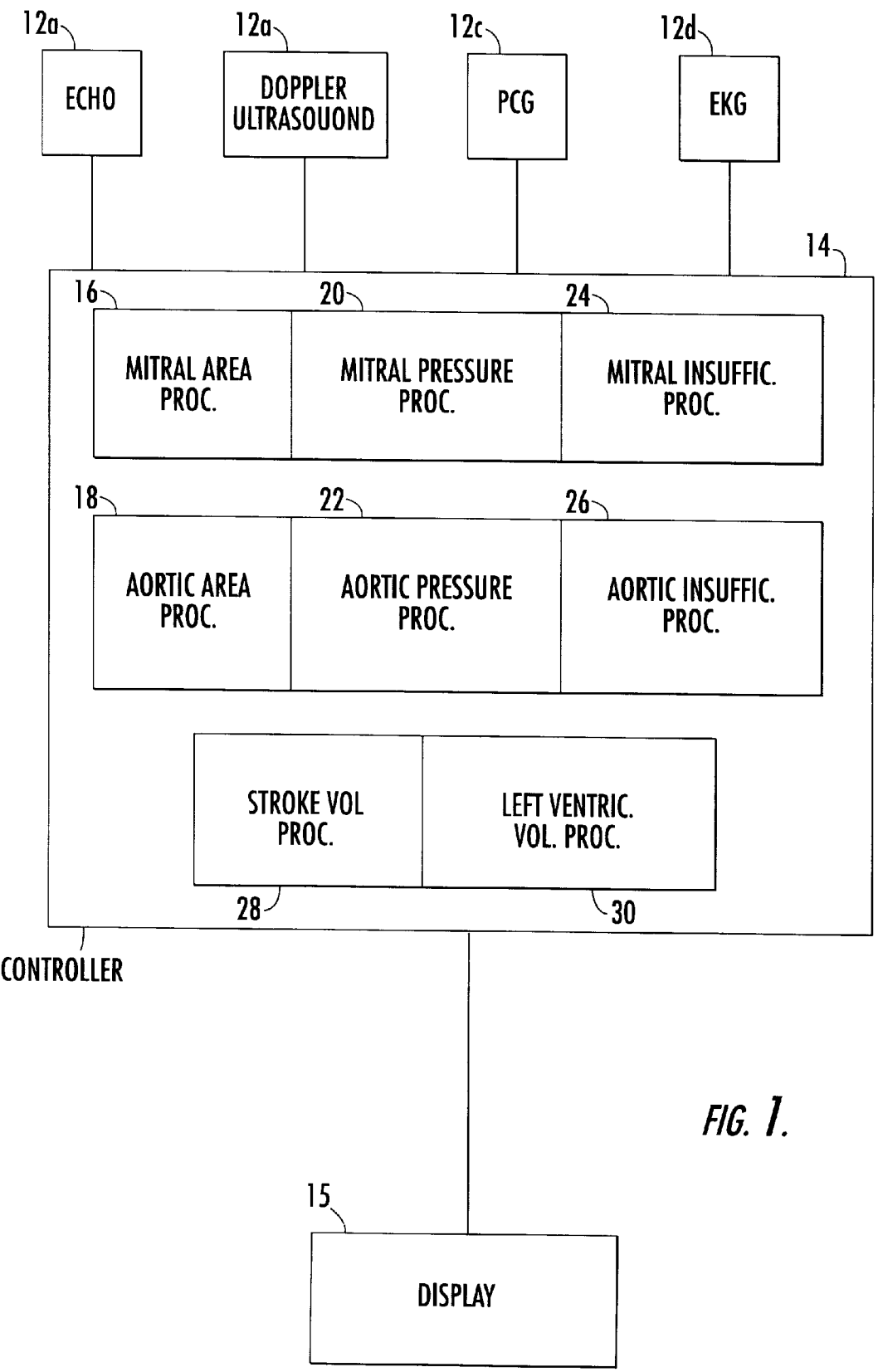
FIG. 1 is a schematic diagram of the apparatus of the present invention.
Figure 2A:
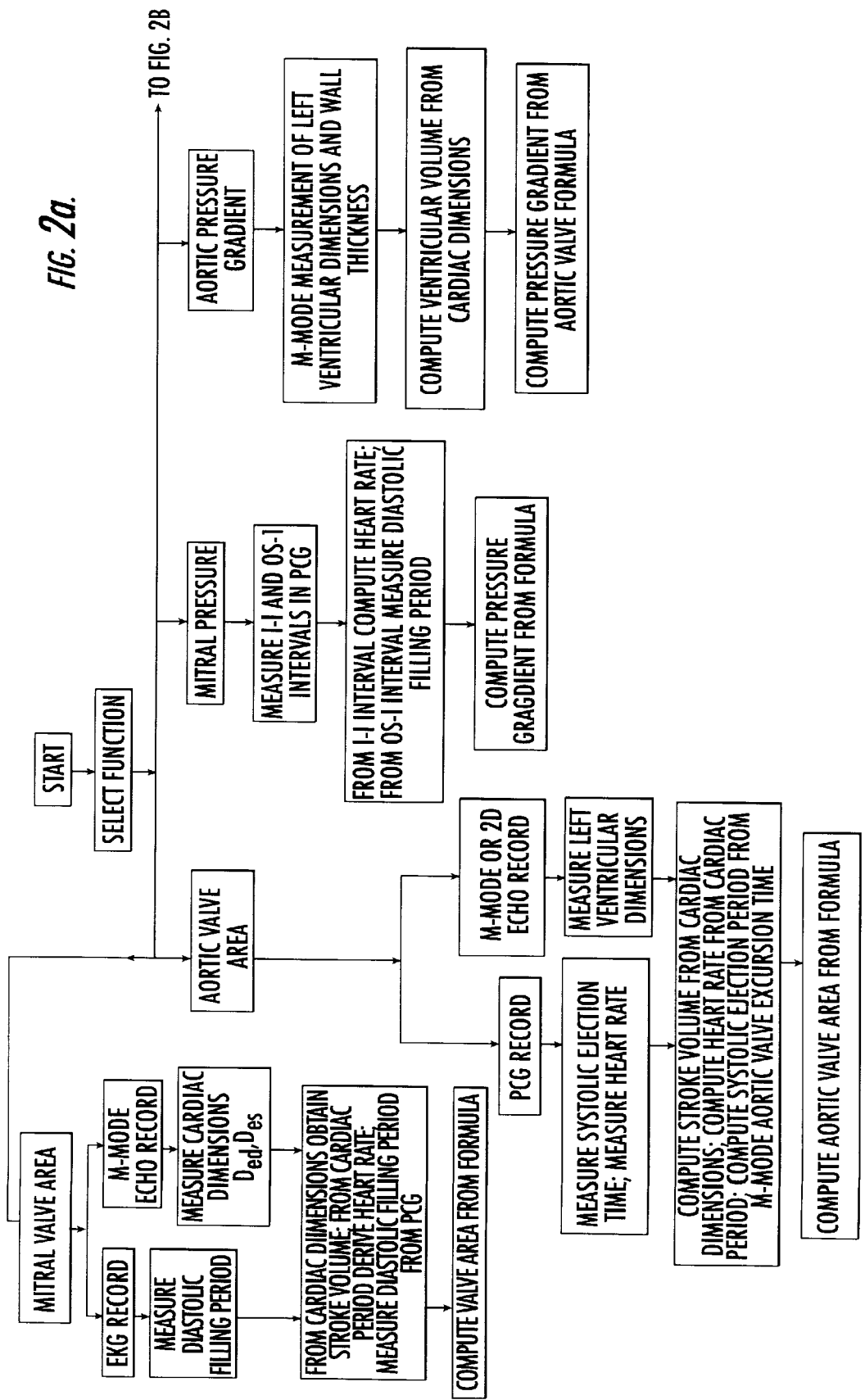
FIG. 2*a,b* are flow charts illustrating the process of the present invention.
Figure 2B:
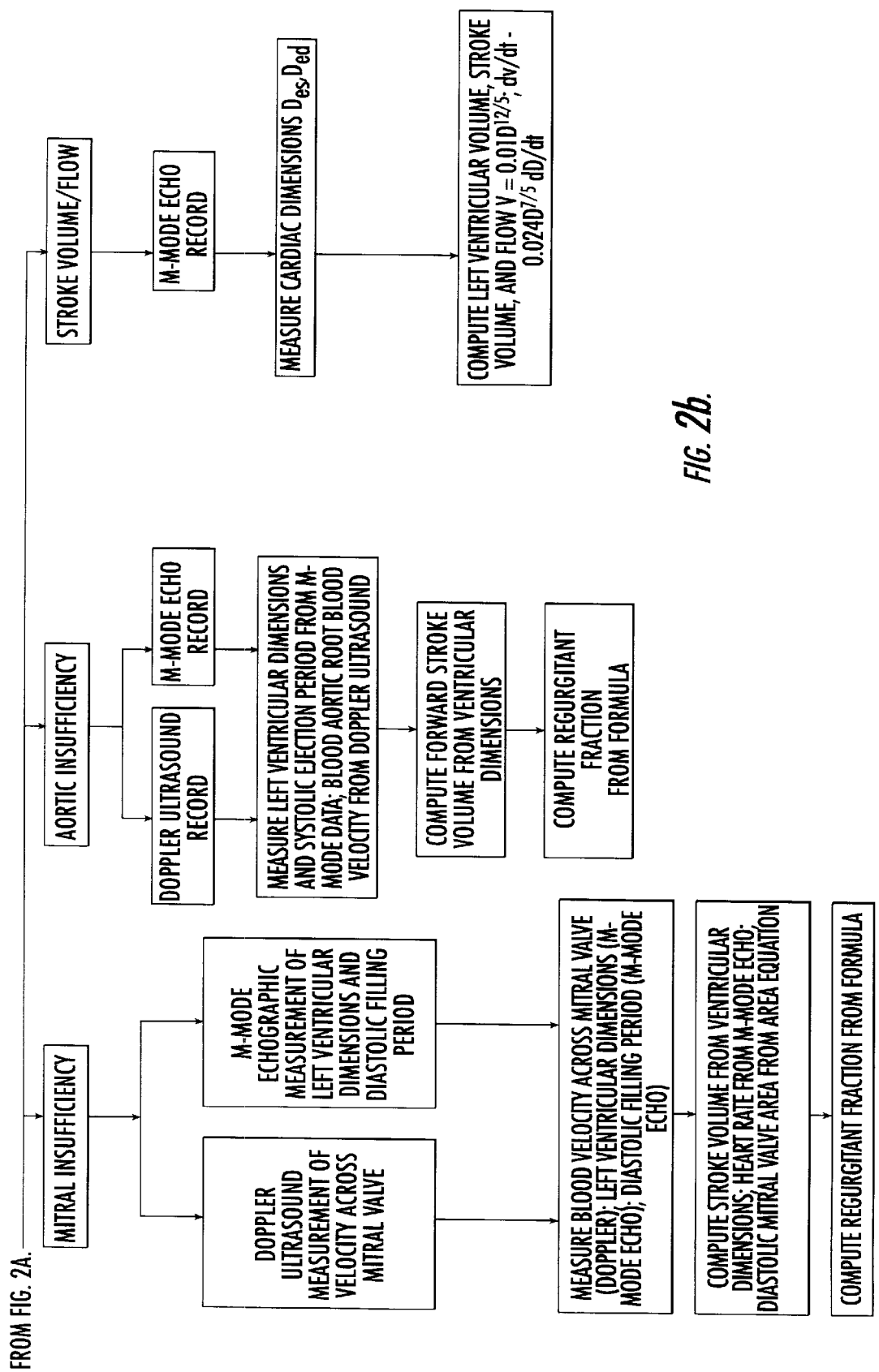
Figure 3A:
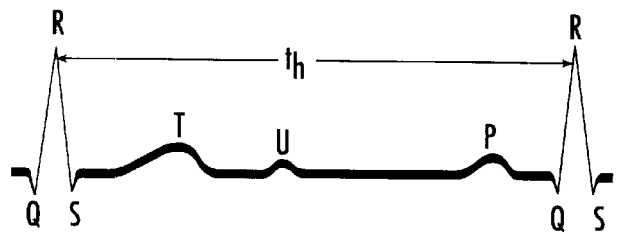
FIG. 3*a,b* are typical EKG and PCG records, respectively, of a patient with mitral valve stenosis showing relevant cardiac intervals for use in calculating mitral valve area.
Figure 3B:
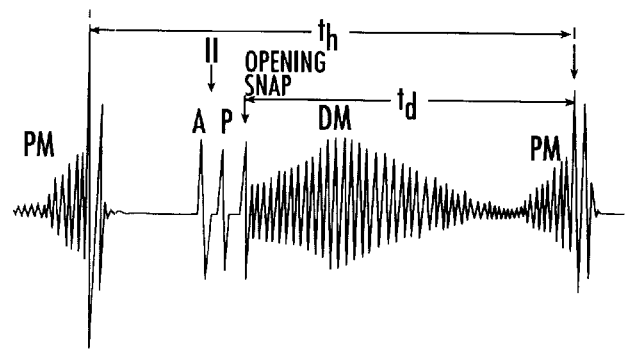

A description of the preferred embodiments of the present invention will now be presented with reference to FIGS. 1–8. As the theoretical model developed herein is applicable to a wide variety of cardiac valve parameters and conditions, the following discussion is segregated into seven sections to more clearly identify each embodiment of the invention. FIG. 1 is a block diagram illustrating the interconnections of the elements of all the embodiments of the apparatus to be discussed herein, although it should be pointed out that additional embodiments are contemplated as being subsumed under the present invention.

1. Noninvasive Assessment of Effective Mitral Valve Area

Derivation of the Cardiac Valve Orifice Area Equations

In this section it is demonstrated how the general system of equations governing the behavior of fluid motion may be applied to cardiac valve flow through the use of a set of simplifying assumptions. It will be seen that the general flow system may be reduced to the one-dimensional Euler continuity equation, which in turn yields a solution for orifice area. By combining the component solutions of this equation, it is further shown that a pressure-independent solution for orifice area may be developed for both the mitral and aortic valves (Section 2).

Application of the geometric mean to the three independent orifice area formulas yields two additional orifice equations that have application under two special conditions. First, in hemodynamic states where the pressure differential is uncertain, and second, in conditions where the valvular flow interval is uncertain, such as arrhythmic conditions.

The General Equations of Fluid Physics

A system of equations necessary and sufficient completely to specify the motion of a general fluid are (1) the equation of continuity, (2) the equations of motion, (3) the constitutive equations expressing the stress and strain relations with the fluid, (4) the first law of thermodynamics (conservation of energy), (5) the caloric equation of state describing the internal energy of the fluid as a function of density and temperature, (6) the Fourier law of heat conduction describing the transfer of heat energy in and out of the fluid, and (7) the kinetic equation of state expressing the relations between pressure, density, and temperature for a compressible fluid.

This system of equations may be expressed symbolically using standard tensor notion (Einstein summation convention assumed) as:

The equation of continuity:

$$\dot{q}+(qv_i)_{,i} \qquad (1.1)$$

where q is the density, $v_i$ is the velocity field vector, $\dot{q}$ is the total time derivative of the density, and $(qv_i)_{,i}$ is the spatial gradient of the product $(qv_i)$.

The equations of motion:

$$s_{ij,i}+qf_i=q\dot{v}_i \qquad (1.2)$$

where $s_{ij,i}$ is the divergence of the stress field tensor, $s_{ij}$ and $f_i$, are the external forces acting on a fluid element, and $\dot{v}_i$ is the total time derivative of the velocity field.

The constitutive equation:

$$s_{ij}=-pd_{ij}+sd_{ij}D_{kk}+2m\ D_{ij} \qquad (1.3)$$

where $s_{ij}$ is as in eq. (1.2), p is the scalar pressure field within the fluid, $d_{ij}$ is the Kroneker delta symbol ($d_{ij}=1$, i=j; $d_{ij}=0$, i≠j), s and m are the coefficients of viscosity, $D_{ij}$ is the symmetric portion of the spatial gradient of the instantaneous velocity field $[D_{ij}=(\frac{1}{2})(v_{i,j}+v_{j,i})]$, and $D_{kk}=v_{k,k}$.

The first law of thermodynamics (conservation of energy):

$$q\dot{u}=s_{ij}\ D_{ij}-c_{i,i}+qz \qquad (1.4)$$

where u is the internal energy of the fluid, $\dot{u}$ is the total time rate of change of internal energy, $D_{ij}$ and $s_{ij}$ are as in eq. (1.2), $c_i$ is the heat flux per unit area per unit time into the fluid due to conduction or convection, $c_{i,i}$ is the divergence of this flux, q is the fluid density, and z is the radiant heat constant per unit mass per unit time.

The caloric equation of state:

$$u=u(q, T) \qquad (1.5)$$

indicates that u, the internal energy of the fluid, is a function of density and temperature.

The Fourier law of heat transport:

$$c_i=-CT_{,i} \qquad (1.6)$$

where $c_i$ is as in eq. (1.4), C is the thermal conduction constant, and $T_{,i}$ is the spatial gradient of the temperature field.

The kinetic equation of state:

$$p=p(q,T) \qquad (1.7)$$

where p is the scalar pressure field, q is the density, and T is the internal temperature distribution.

These equations plus the associated boundary conditions appropriate to the flow configuration under consideration form a complete and determinate system, which in principle allows one to solve any flow problem in classical fluid mechanics. In this generalized form a solution for even the most elementary heart valve configuration is analytically inaccessible.

We shall now make a series of simplifying assumptions and approximations that will reduce this general system of equations to an elementary form yet preserve the essential features of valvular flow with respect to the development of an orifice equation.

Assumptions Allowing a Reduction of the General System

1. Blood is an incompressible fluid with constant density.
2. The blood temperature distribution within the heart is constant in time and uniform in space.
3. There is no significant transfer of heat by radiation, conduction, or convection between the heart and its immediate environment.
4. The Reynolds number for blood flow within the heart and cardiac valves is large (>>1); i.e., viscosity effects are insignificant relative to the dominant inertial term.
5. In the absence of an acute rheumatic process, the cardiac valvular orifice area is constant over many cardiac cycles.
6. The velocity and pressure variations along an axis parallel to the normal direction of the plane of the valvular area are representative of the variations along any other parallel axis; i.e., the flow is dominantly one-dimensional.
7. The flow-pressure variations across the cardiac valves are cyclic in nature and may be approximately represented by sinusoidally varying functions in space and time.

Discussion of the Assumptions

1. The incompressibility of blood follows from the fact that its principle constituent, water, is incompressible. The remaining molecular components, chiefly plasma proteins, have a minimal degree of compressibility at pressure levels expected within the cardiac chambers.

2. Uniformity of spatial and temporal blood temperature may be expected in the absence of inflammatory processes in or near the heart. It is conceivable that very low air temperature could influence the temperature of the pulmonary venus return blood temperature to the left heart; however, in normal environments this is not expected.

3. Radiation, conduction, and convective transport of heat energy require a temperature gradient between the energy-transmitting and -receiving objects. In the absence of a temperature gradient (assumption 2), we do not expect these terms to play a significant role in the motion of blood in heart chambers and valves.

4. The Reynolds number is defined as Re=ul/v, where u is a characteristic velocity, l a characteristic length, and v the kinematic viscosity of the fluid. If we assume a characteristic length for a typical cardiac dimension to be the radius of a sphere containing an average cardiac volume (V), l=(3V/4π)$^{1/3}$, we find l=3 cm. If we take a characteristic velocity u defined by a typical mitral valve flow (200 ml/sec) and a typical mitral valve area (4 cm$^2$), we find u=50 cm/sec. Taking blood viscosity as v=0.02 cm$^2$/sec yields a Reynolds number of Re=7500. Thus we expect the inertial term to dominate the flow considerations.

5. The assumption of constancy of the cardiac valve area for a wide range of hemodynamic states in the absence of acute obstructive conditions is consistent with the assumptions underlying the orifice area model of Gorlin and Gorlin (1951). The experimental validity of this assumption resides in the observation that the correlation between the valve areas in rest and exercise conditions from the original data of Gorlin and Gorlin is r=0.97. Furthermore, the correlation between autopsy measurements and valve areas as computed in vivo via the Gorlin formula correlate at a level of r=0.92.

6. The assumption that the flow may be represented as one-dimensional is based on earlier modeling studies and experimental pressure-flow measurements across artificial mitral and aortic valves. In theoretical and experimental studies it was demonstrated that a one-dimensional theory could predict the essential pressure and flow distribution in simulated valve flow configurations at a level consistent with the measurements.

7. The assumption of the approximate sinusoidal space-time behavior of the pressure-flow functions likewise has its basis in experimental observations, wherein approximate sinusoidal behavior of the pressure-flow wave form in simulated aortic valve flow was reported. Furthermore, pressure distributions have been measured across simulated aortic valves and were found to trace closely approximating sinusoidal wave forms. Fluid mechanical studies on artificial hearts and mitral valves have likewise revealed approximate sinusoidal behavior of the pressure-flow functions.

Application of the Assumptions to the General System of Fluid Flow Equations

According to assumption (1), we are considering only an incompressible fluid. The kinetic equation of state (1.7) describes the pressure, density, and temperature relationships in a compressible fluid. Assumption (1) thus allows the elimination of this equation from consideration.

Assumption (2) concerning the uniformity of the temperature distribution within the fluid implies that the spatial gradient of T, $T_{,i}=0$. Thus the Fourier law, eq. (1.6), becomes $c_j=0$.

Applying assumptions (1) and (2), q and T=constant, allows us to conclude that the internal energy is constant. Equation (1.5) thus becomes $u(q,T)$=constant.

The constancy of internal energy indicates that the time derivative of internal energy is zero. Thus u=0, and eq. (1.4) becomes:

$$0 = s_{ij} D_{ij} - c_{i,i} + qz \quad (1.8)$$

Application of assumption (2) leads to the result that $c_i$=0; thus the spatial gradient of $c_i$ is also zero; i.e., $c_{i,j}$=0. Application of assumption (3) regarding the absence of radiative energy transfer within the fluid indicates that qz=0. Thus eq. (1.8) becomes $s_{ij}D_{ij}$=0.

Substitution of the constitutive eq. (1.3) into the equations of motion (1.2) leads to:

$$qv_i = qf_i - gp_{,i} + (s+m)v_{jji} + mv_{i,jj} \quad (1.9)$$

Using assumption (1), the continuity equation may be written as $v_{i,j}$=0; i.e., the divergence of the velocity field vanishes, and eq. (1.2) becomes:

$$qv_i = qf_i - p_{,i} + mv_{i,jj} \quad (1.10)$$

where $v_{i,ji}$ is the Laplacian of the velocity field; i.e., $v_{i,ji} = \nabla^2 \underline{v}$, and the other terms are as defined above. Equation (1.10) expresses the Navier-Stokes equations for the flow. Assumption (4) allows a further simplification of eq. (1.10). Large Reynolds numbers imply that energy expended in inertial motion is large compared to energy dissipated by resistive losses mediated through the effects of viscosity. Setting m=0, eq. (1.10) becomes:

$$qv_i = qf_i - p_{,i} \quad (1.11)$$

The term $qf_i$ represents the external forces acting on a representative fluid element.

Application of the various assumptions has excluded the forces due to thermal expansion and heat transport; however, the possibility of the effects of a gravitational force acting on the fluid element has not yet been excluded. We shall judge the possible magnitude of the effect by comparing the pressure produced by a gravitational field with characteristic pressures within the heart chambers.

The pressure difference in dynes per $cm^2$ in a fluid produced by a gravitational field due to a vertical separation h is given as dp=qgh, where q is the fluid density and g is the gravitational constant (=980 $cm/sec^2$). If we take a characteristic internal dimension of the heart as 2.5 cm (the radius of a sphere containing a representative stroke volume), we find a regional pressure difference in the chamber due to gravitational effects of 2450 $dynes/cm^2$, or 1.85 mm Hg. Due to the predominantly horizontal position of the heart, this gravitationally produced regional pressure difference across the heart valves is minimized. If the normal axis to the surface of the valvular cross-sectional area is perpendicular to the vertical, the predominant case, the gravitational contribution to pressure differential across the cardiac valve is essentially zero, reaching an approximate maximum of 1.85 mm Hg in the extreme case. The theory to be developed herein is primarily concerned with pathological flow conditions (stenosis), wherein the pressures are elevated to levels considerably greater than 1.85 mm Hg. An assumption may thus be made that all external forces in eq. (1.2), including gravitational forces, are minimal and $qf_i$0. Thus:

$$qv_i + p_{,i} = 0 \quad (1.12)$$

The first term of this equation is the product of q with the total time derivative of the velocity field, $v_i$; the second term is the spatial gradient of the pressure field p. Rewriting eq. (1.12) in vector form and noting that the total time derivative is given by the partial time derivative plus the convective spatial derivative, we have:

$$q(d\underline{v}/dt) + q(\underline{v} \cdot \nabla) \cdot \underline{v} + \nabla p = 0 \quad (1.13)$$

According to assumption (5), the flow may be represented in one dimension; thus eq. (1.13) becomes (with q=1 g/ml):

$$(dv/dt) + v(dv/dx) + v(dp/dx) = 0 \quad (1.14)$$

Assumption (3) permits the writing of the equation of continuity as $v_{i,j}$=0 or $\nabla \cdot \underline{v}$=0. Using Green's theorem, eq. (1.1) may be transformed as:

$$\iiint \nabla \cdot \underline{v} \, dV = \iint v_n \, dA$$

where the left side represents an integral over volume (V), the right side is the surface integral over the surface (A) bounding the volume, and $v_n$ is the normal component of $\underline{v}$ across the area element dA. We thus have $\iint v_n \, dA$=0 for an arbitrary surface in the fluid. Representing the arbitrary volume, V, by a cylindrical element with cross-sectional area $A_o$ and A, we have $v_o A_o + vA$=0 as an expression of the equation of continuity. Here $v_o$ represents the velocity of fluid flowing into the volume element across $A_o$ and v the velocity of fluid flowing out of the element across A. We have not considered flow orthogonal to the axis of the arbitrary cylindrical test volume since by the one-dimensional assumption this is zero. Accounting for the sense of the flow, we may express eq. (1.1) as $vA - v_o A_o$=0. Identifying the flow Q in volume per unittime as Q=$v_o A$=vA enables us to express the flow in terms of velocity and area. Thus, in one dimension, the representative expressions for the Euler and continuity equations become:

$$(dv/dt) + qv(dv/dx) + (dp/dx) = 0 \quad (1.16)$$

$$Q = vA \quad (1.17)$$

Forming the partial temporal and spatial derivatives of eq. (1.17) yields:

$$(dQ/dt) = v(dA/dt) + A(dv/dt) \quad (1.18)$$

$$(dQ/dx) = v(dA/dx) + A(dv/dx) \quad (1.19)$$

We now apply assumption (7) regarding the constancy of valve area in the absence of acute obstructive processes. Thus, for $A(x,t)$=constant, $(dA/dt)=0$, $(dA/dx)=0$, and eqs. (1.18) and (1.19) become:

$$(dQ/dt)=A(dv/dt) \qquad (1.20)$$

$$(dQ/dx)=A(dv/dx) \qquad (1.21)$$

Equation (1.16) thus becomes:

$$(1/A)(dQ/dt)+(1/A^2)(dQ/dx)+(dp/dx)=0 \qquad (1.22)$$

We now note that the flow term, Q, has the meaning of volume per unit time. During the inertial phase of the valvular flow cycle, the flow may be expressed as $Q=(d \cdot V/dt)$, where V is interpreted as the stroke volume. During the convective or steady-state phase of the flow, we will interpret flow as $Q=(V/t)$, where t is the valvular flow interval. The spatial derivative $(dQ/dx)$ may be expressed as $(d^2V/dtdx)$. Since we take $(dV/dt)=(V/t)$ for the convective component of the total time derivative in eq. (1.22), $(d^2V/dtdx)=(V/t)(dV/dx)$. Next we express eq. (1.22) as:

$$(1/A)(dQ/dt)+(1/A^2)(V/t)(dV/dx)+(dp/dx)=0 \qquad (1.23)$$

and we apply assumption (6), which allows us to express the space-time behavior of the volume and pressure fields in the form of periodic functions of sinusoidal nature in x and t.

Thus we represent volume, $V(x,t)$, and pressure, $p(x,t)$, as:

$$V(x,t)=V\, e^{i(wt-kx)} \qquad (1.24)$$

$$p(x,t)=pe^{i(wt-kx)} \qquad (1.25)$$

forming the appropriate partial derivatives yields:

$$(dV/dt)=iwV \qquad (1.26)$$

$$(d^2V/dt^2)=iw^2V \qquad (1.27)$$

$$(dV/dx)=-ikV=-kVe^{-\pi i/2} \qquad (1.28)$$

$$(dp/dx)=-kip=-kVe^{-\pi i/2} \qquad (1.29)$$

$$(d^2V/dtdx)=-ke^{-\pi i/2}(dV/dt) \qquad (1.30)$$

Substituting eqs. (1.27), (1.28), and (1.29) into eq. (1.24) and noting that $(dV/dt)$ is interpreted as $(V/t)$ in the convective derivative term, we obtain:

$$A=(-2p\theta)^{-1}\{k^{-1}w^2V+[k^{-2}w^4V^2-4p(V/t)^2\theta^2]^{1/2}\} \qquad (1.31)$$

calling the phase term, $e^{-\pi i/2}=\theta$ and solving eq. (1.31) for A gives:

$$A=(-2p\theta)^{-1}\{k^{-1}w^2V \mp [k^{-2}w^4V^2-4p(V/t)^2\theta^2]^{1/2}\} \qquad (1.32)$$

Equation (1.32) represents the effective orifice area in terms of a pure imaginary number due to the presence of the phase $\theta$. The magnitude of this number contains the information of physical interest; thus we will take the modulus of eq. (1.32) as representing the effective orifice area. Additionally we will choose the positive sign on the radical so as to avoid a negative surface area and interpret dp as the valvular pressure differential. This yields:

$$A=[k^{-2}w^4V^2/4dp^2+(V/t)^2/dp)]^{1/2}+k^{-1}w^2V/2dp \qquad (1.33)$$

Equation for the Mitral Value Orifice Area

We now turn to the evaluation of the physical parameters, V, w, dp, t, and k, which define the variable of interest. We have already identified V with the stroke volume. The variable w is the frequency of the volume-pressure wave form in radians per second. We may convert this to heart frequency in conventionally measured units by noting that $60w=2\pi F$. The parameter dp is the valve pressure differential in $dyn/cm^2$. The relationship between mm Hg and $dyn/cm^2$ is 1 mm $Hg=1333$ $dyn/cm^2$. The variable t is the mitral valve flow interval in seconds per beat. The parameter k is the wave propagation number and is directly related to the distance over which a wavelike disturbance is propagated over one cycle. For the mitral valve flow problem this distance can be interpreted as the distance between the center of mass of the blood volume at the beginning and end of the valvular flow cycle, respectively. We shall take this to be the average distance between the centroid of the left atrium and the centroid of the left ventricle. We may estimate this distance by noting that the distance between the centroids of two spheres of volume V (in $cm^3$) is $1=2(3V/4\pi)^{1/3}$. The propagation number, k, is given by the terms of the distance, l, as $k=2\pi l$. The average stroke volume is circa 75 ml. This gives a value of k as $1.20$ $cm^{-1}$.

To complete the solution of the orifice area equation, we need to modify the area as computed by eq. (1.33) by determining the discharge coefficient appropriate to the flow conditions. The discharge coefficient relates area, flow, and pressure according to some functional relationships between the variables as determined by the specific form of the orifice equation and may be expressed symbolically as $C_d=_d(Q,A,dp,q)$.

When flow occurs from one cardiac chamber with cross-sectional area $A_o$ to another through an orifice of cross section A, the discharge coefficient may be expressed in terms of another function, the contraction coefficient $C_c$, as:

$$C_d=C_c[1-(C_cA/A_o)^2]^{-1/2} \qquad (1.34)$$

The coefficient $C_c$ is, in turn, a function of the cross-sectional area, $A^*$, of the jet emerging from the orifice and the orifice cross-sectional area, A. Experimental measurements of this function for a geometry similar to the present model indicate that this value is between 1.0 and 0.611 for $(A^*/A)$ ratios ranging from 1.0 to 0.01. Furthermore, a two-dimensional theory yields $C_c=\pi/(\pi+2)=0.611$ for a slot orifice in an infinite plane wall. The close correspondence with the axisymmetrical experimental configuration suggests that the theoretical values for the axisymmetrical problem are probably also identical.

The area, $A_o$, in eq. (1.32) represents the cross-sectional area of the left atrium. We can approximate this value by the cross-sectional area through the center of a sphere of volume equal to the average stroke volume in stenosis (75 ml). This gives an area of $A_o=(3V/4\pi)^{2/3}\pi=22$ $cm^2$. If we consider mitral valve orifice areas lying in the range of 1–6 $cm^2$, calculate $A/A_o$, and substitute this into eq. (1.31), we find that $C_d=C_c$ for this range of areas. Thus, for area ratios of interest for the mitral valve, $C_d$ is essentially equal to $\pi/(\pi+2)=0.611$.

In classical flow dynamics the discharge coefficient enters the orifice equation as a multiplicative factor of A. Thus we take the final form of eq. (1.32) to be:

$$A=1.64(k^{-2}w^4V^2/4dp^2+(V/t)^2(1/dp)^{1/2}+k^{-1}w^2(V/2dp) \qquad (1.35)$$

This solution to the Euler-continuity equation may be seen to comprise two distinct entities. First, a term $(V/t)^2/dp$ relating $v(dv/dx)$ and $(dp/dx)$. Second, a term $k^{-1}w^2V/2dp$, relating $(dv/dx)$ and $(dp/dx)$. We shall denote these terms $A_c$ and $A_m$, respectively.

The Euler equation may be viewed as an expression of the conservation of energy and momentum for the flow process. The Euler equation combined with the equation of continuity and the associated boundary conditions provides a complete description of the space-time history of the pressure and velocity fields for inviscid flow. In this study we are concerned with an expression for the valve orifice area rather than a complete description of the flow-pressure fields. Since both energy and momentum must be independently conserved for any physical process, there may be sufficient information in either the energy-continuity or momentum-continuity conservation components of the expression for A to derive a satisfactory orifice equation. If this concept is correct, we might well expect that the terms $A_e$ and $A_m$ will independently yield an equation for orifice area.

In order to evaluate this concept, we form the ratio of $A_e/A_m$ for a series of hemodynamic states and judge the constancy of this ratio. For the 150 cases of Tables 1–10, $A_m/A_e = 0.20 \pm 0.02$ (X+SD). The expected error in the ratio $(A_m/A_e)$ may be computed from $y=(A_m/A_e)=k^{-1}w^2t/(2dp^{1/2+1})$. Thus:

$$\max(dy/y) = [2dw/w + dk/k + dt/t + (\tfrac{1}{2})(dp/p)] \quad (1.36)$$

If we estimate expected relative measurement errors in w, t, k, and p of 5%, 10%, 10%, and 10% respectively, the ratio dy/y is expected to be uncertain by a maximum of 35%. As a further test of the relationship between $A_e$ and $A_m$, we correlate $A_e$ with $A_m$ for 46 catheterization investigations (Tables 8 and 9). This analysis revealed a correlation of r=0.95 between $A_e$ and $A_m$. We may thus express eq. (1.33) in terms of the conventionally used hemodynamic variables measured at cardiac catheterization using the conversion factors between radial frequency, heart rate, and pressure in mm Hg. This yields:

$$A_{EC} = 1.64[(V/t)^2/(36.5dp)^{-2} + 11.75 \times 10^{-12} R^4 V^2/dp^2]^{1/2} + 3.45 \times 10^{-6}(R^2 V/dp) \quad (1.37)$$

The component terms of $A_{EC}$ are:

$$A_e = V/(36.5 t dp^{1/2}) \quad (1.38)$$

$$A_m = 3.45 \times 10^{-6}(VR^2/dp) \quad (1.39)$$

Evaluation of the Scaling Factors $K_M$ and $K_A$

The ratio $y=(A_e/A_m)$ was found to be constant within the limits of expected measurement error. This observation suggested that the effective orifice area, $A_{EC}$, may be expressed either in terms of $A_e$ or $A_m$ when an appropriate scaling factor is applied. According to this concept, we write $A_e = k_m A_m$ and $A_{EM} = K_m A_m$. The solution of the Euler-continuity equation is seen to be:

$$A_{EM} = (A_e^2 + A_m^2)^{1/2} + A_m \quad (1.40)$$

Substituting $A_e = k_m A_m$ into eq. (1.40) gives:

$$A_{EM} = A_m[(1+k_m^2) + 1] \quad (1.41)$$

Calling $K_m = (1+k_m^2)^{1/2} + 1$, we may evaluate the scaling factor from the known averages of $(A_e/A_m)$ for the mitral and aortic valves. For the mitral valve the ratio $k_m$ was found to be 12.4. This gives $K_m = 13.45$. The theoretical value of the discharge coefficient is given as $(\pi+2)/\pi = 1.64$. Since the term $A_m$ contributes approximately 8% to the total value of $A_{EM}$, we must weigh its contribution to the discharge coefficient in the scaled value of $A_m$. This yields $K^m_m = [1 + (1.64/12.4)](11.45)$, or $K^m_m = 13.15$.

For the aortic valve the ratio $k_m = (A_e/A_m)$ was found to be 12.45, giving a value of $K^a_m = 13.5$. Since the discharge coefficient was found to be 1.0 for the aortic valve, the scaling factor for the $A^a_m$ term is $K^a_m = 13.5$. In terms of the parameters measured at catheterization, the valve area derived from the inertial term of the Euler-continuity equation becomes:

$$A^m_m = 5.2 \times 10^{-5}(VR^2/dp) \quad (1.42)$$

Derivation of a Pressure-Independent Orifice Formula

The development of an orifice formula directly from the one-dimensional Euler equation indicates that two terms, $A_e$ and $A_m$, contribute to the effective orifice area in a periodic flow system. One of these terms, $A_e$, is associated with the steady-flow component and may be viewed as relating kinetic energy and pressure through the continuity equation. The second term, $A_m$, is associated with the periodic nature of blood flow in cardiac valves and may be considered as relating the inertial forces reacting against the force per unit area produced by the pressure propelling the blood through the valve. The ratio $(A_m/A_e)$ is constant within the limits of measurement errors associated with the variables defining the ratio. We therefore make the final assumption of this model, that $A_m$ and $A_e$ are independently capable of predicting orifice area. We may therefore solve these expressions simultaneously so as to eliminate the pressure differential. The two equations are found to be:

$$A_e = aV/(t dp^{1/2}) \quad (1.43)$$

$$A_m = bVR^2/dp \quad (1.44)$$

where a and b are the constants of proportionality. Substituting dp from eq. (1.44) into eq. (1.43) leads to $$A = KV/(tR)^2 \quad (1.45)$$

where $K = /(a^2 b)$. We may identify the product, tR, with the valvular flow interval T in seconds per minute (T=tR). Equation (1.45) thus becomes:

$$A = KV/T^2 \quad (1.46)$$

The constant K must be evaluated separately for the particular cardiac valve considered. Here we consider only the mitral valve. K may be found from knowledge of the coefficients a and b as found from the analysis presented in the previous sections or by a regression analysis of the ratio of $(V/T^2)$ on A. The coefficient a may likewise be evaluated by regression analysis of $V/(t\, dp^{1/2})$ on $A_e$ or by the theoretical considerations given previously. The coefficient b may be determined by a regression analysis of the ratio $VR^2/dp$ on $A_m$ or by the theoretical estimates given previously. The coefficient k associated with the alternate derivation of the equation for $A_m$ may be combined with the Gorlin constant, $C_G$, through the relationship $K=1/kC^2_G$. The value of k is found to be $k_m = 4.75 \times 10^{-5}$ for the mitral valve. The Gorlin constant for this equation is 31. Combining these values yields $K_m = 21$. Evaluating $K_m$ from the theoretical considerations presented above leads to the value $K_m = 27$. These differences are within the expected error limits of the methods used to evaluate the relevant parameters. For the purposes of comparison with standard catheterization methods, we use the coefficient $K_m = 21$. Thus the final expression for effective orifice area is:

$$A_m = 21\, V/T^2_m \quad (1.47)$$

$$A_a = 7\, V/T^2_a \quad (1.48)$$

where $A_m$ is the mitral valve area in cm$^2$, V is the stroke volume in ml, $T_m$ is the diastolic filling period in seconds per diastolic minute, $A_a$ is the effective aortic valve area in cm$^2$ and $_aT$ is the systolic ejection period in seconds per systolic minute.

Extrapolation of the Inviscid One-Dimensional Solution to Include Three-Dimensional and Viscous Effects The derivation of the steady-flow solution is valid for a general three-dimensional inviscid flow. It is seen that the convective term for one-dimensional and three-dimensional flow differs by a factor of $2^{1/2}$. This result suggests that the steady-flow component of the one-dimensional flow, $A^1_e = gV/(36.5\ t\ dp^{1/2})$, should be modified to:

$$A^3_e = V(51.5 t dp^{1/2}) + tm \quad (1.49)$$

The theoretical justification for this correction resides in the fact that previously given results revealed that the steady-flow term $A_e$ was approximately ten times the magnitude of the inertial term $A_m$ for both mitral and aortic valve flow. Furthermore, it was seen that the ratio $(A_m/A_e)$ is constant to within the expected measurement error limits; thus the steady or convective acceleration component is the dominant term in the solution of the Euler-continuity equations for a wide range of hemodynamic states.

We have taken the value of the contraction coefficient to be given by the theoretical value as $\pi/(2+\pi)=0.611$. This value includes the expected resistive losses. Thus the steady-flow component $A^3_e$ for three-dimensional flow becomes:

$$A^3_e = V/(31 t dp^{1/2}) \quad (1.50)$$

This is equivalent to the Gorlin formula for the mitral valve. In one dimension we have seen that the propagation number was approximately 1.20 cm$^{-1}$ for the mitral valve. This value was found by considering the distance traveled by a mass of blood equal to an average stroke volume in stenosis. In three dimensions we must also consider the range of motion available to a representative fluid mass point in the two independent orthogonal directions of the axis normal to the valvular areas. We estimate the orthogonal ranges as the radii of spheres whose volume equals an average stroke volume in stenosis (75 ml). Thus $r_1=5.2$ cm, $r_1=r_2=2.6$ cm, $k_1=1.2$ cm$^{-1}$, $k_2=k_3=2.6$ cm$^{-1}$. The internal component of the Euler equation for the mitral valve thus becomes:

$$A^3_m = 1.16 \times 10^{-6}(VR^2/dp) \quad (1.51)$$

The orifice equation for the mitral valve is then:

$$A^3_{EC} = (1.64)(V^2/(51.5 t dp^{1/2})^2 + 1.35 \times 10^{-12} V^2 R^4/dp^2)^{1/2} + 1.16 \times 10^{-6}(VR^2/dp) \quad (1.52)$$

In summary:

$$A^{1m}_{EC} = (1.64)[V^2(36.5 t)^{-2} dp^{-1} + 11.75 \times 10^{-12} V^4 R^2/dp^2]^{1/2} + 3.45 \times 10^{-6}(R^2V/dp) \quad (1.53)$$

$$A^{3m}_{EC} = (1.64)[V^2(51.5 t)^{-2} dp^{-1} + 1.35 \times 10^{-12} V^4 R^2/dp^2]^{1/2} + 1.16 \times 10^{-6}(VR^2/dp) \quad (1.54)$$

Derivation of Two Alternate Expressions of Value Area for Use in Special Circumstances We have shown that the solution of the Euler-continuity equation yields an expression for orifice area in terms of a steady-state component that is functionally equivalent to the Gorlin formula, and an inertial- or unsteady-flow component that yields essentially the same valve areas as the Gorlin formula. Furthermore, it was demonstrated that a combination of the steady-flow and inertial-flow components of the Euler-continuity equation gave a new area equation that independently predicts valve areas at a level compatible with that of the Gorlin formula or independent anatomical measurements.

The area computed by the steady-flow component of the Euler-continuity equation is now defined as $A_E$, the area computed by the inertial component as $A_M$, and the area computed by the pressure independent equation as $A_N$. These three equations predict essentially the same values for valve area given the same hemodynamic parameters within the limits of expected measurement errors. In this discussion, therefore, these three expressions are regarded as independent expressions for valvular area.

If two functions, say, $f_1$ and $f_2$, independently map portions of the domains of their independent variables to the same range, the geometric mean, $(f_1 f_2)^{1/2}$, of the two functions also maps the domain of the independent variables to the range of $f_1$ and $f_2$. This formulation is common in certain fields of applied science such as electronics, optics, and acoustics, for representing the range of a function intermediate to two functions $f_1$ and $f_2$. We shall use this concept to derive two additional orifice area equations having a different functional dependence upon the independent hemodynamic variables.

The steady-flow solution is:

$$A_E = C^{-1}_d V t^{-1} dp^{-1/2} \quad (1.55)$$

The inertial component is given by:

$$A_M = k V R^2/dp \quad (1.56)$$

These equations can be combined by simultaneous solution so as to eliminate the pressure differential, yielding an additional orifice expression:

$$A_N = (1/C^2_d\ k) V/(Rt)^2 \quad (1.57)$$

We now form the geometric mean of eqs. (1.55) and (1.56):

$$A_{EM} = (k/C_d)^{1/2} V/(t^{1/2} dp^{3/4}) \quad (1.58)$$

where V (=RV) is the cardiac output in ml/min. Forming the geometric mean between eqs. (1.55) and (1.56) yields:

$$A_{EN} = (k/C_d)^{-1/2} (V/R) t^{-3/2} dp^{-1/4} \quad (1.59)$$

Both equations for $A_{EM}$ and $A_{EN}$ correlate with the Gorlin formula at r=0.99 and with independent valve area measurements at essentially identical levels as the Gorlin formula.

The equation $A_{EM}$ depends only on the cardiac output, pressure differential, and flow interval. The dependence on flow interval is to the power $-\frac{1}{2}$; thus this orifice formula would be most appropriate in conditions when the flow interval is of questionable accuracy or in arrhythmic states when accurate measurement of the filling period is difficult.

The equation $A_{EN}$ is weakly dependent upon the pressure differential; thus this formulation is most appropriate in conditions where there are reasons to suspect possible inaccuracies in the pressure measurement.

The final form of the equations for $A_{EM}$ and $A_{EN}$ for the mitral valve is:

$$A^m_{EM} = 1.25 \times 10^{-4} V/(t^{1/2} dp^{3/4}) \quad (1.60)$$

$$A^m_{EN} = 0.67 \times 10^{-4} V/(t^{1/2} dp^{3/4}) \quad (1.61)$$

These expressions are evaluated in comparison with the Gorlin formula, autopsy data, two-dimensional echocardiography and seizer measurements in Tables 1–10.

Summary of Orifice Area Equations for the Mitral Value

The orifice solution for the Euler-continuity equation is:

$$A_{EC}=(1.64)[V^2(51.1t)^{-2}dp^{-1}+1.35\times10^{-12}V^4R^2/dp^2]^{1/2}+1.16\times10^{-6}VR^2/dp \quad (1.62)$$

The steady-flow component solution of the Euler-continuity equation (Gorlin equation for the mitral valve) is:

$$A_E = V(31t)^{-1} dp^{-1/2} \quad (1.63)$$

The inertial component solution of the Euler-continuity equation is:

$$A_M = 4.75\times10^{-5} VR^2/dp \quad (1.64)$$

The pressure-independent orifice equation is:

$$A_N = 21V/(Rt)^2 \quad (1.65)$$

The geometric mean of the steady and inertial component is:

$$A_{EM}=(5.4)\times10^{-3}VRt^{-1/2}dp^{-3/4} \quad (1.66)$$

The geometric mean of the steady-flow and pressure-independent solutions is:

$$A_{EN}=(21/31)^{1/2}(V/R)t^{-3/2}dp^{-1/4} \quad (1.67)$$

Sample Mitral Valve Area Calculation

Referring to FIGS. 1, 2a, 2b, and 3, and using Eq. (1.65), an exemplary calculation for the mitral valve area is provided, although this particular method is not intended to be limiting. The stroke volume SV is computed from the M-mode echocardiogram 12a via eq. (3.1) as will be discussed in Section. 3, where the ventricular dimensions are measured in millimeters and SV is in cubic centimeters. t (here $t_d$, the diastolic filling period) is measured by the OS-I interval in a phonocardiogram 12c, and the heart rate is given by the reciprocal of the I—I interval of the phonocardiogram or the R—R interval in the EKG 12d.

For a particular case, $D_{es}=28$, $D_{ed}=45$, SV=63, $t_d=0.27$, R=95. The mitral valve area A is then calculated to be 1.95; A>2.5 is considered normal.

Tests of the Predictive Capacity of the Present Theory for the Mitral Valve

In this section is studied the validity of the predictions of the orifice area equations in comparison with direct autopsy mitral valve area measurements, measurements of orifice area of excised mitral valves by a special sizing apparatus, in vivo measurements of mitral valve orifice area using bidimensional echocardiographs, and comparisons of orifice areas as calculated by the Gorlin formula at cardiac catheterization.

Comparison of the Predictions of the Present Theory with Autopsy Measurements of Valve Area The development of the Gorlin model for valvular orifice area has been accompanied by autopsy measurements of six mitral valve specimens from patients whose hemodynamic state had been assessed in life. These hemodynamic measurements provide sufficient data to calculate valve areas by the present theory. Summary data are presented in Tables 1 and 2.

The valve areas of the six autopsy cases described in the original study of Gorlin and Gorlin were measured by precisely measuring flow rates and pressure differentials across the valves and then applying a hydraulic orifice equation to calculate area. The area was also measured geometrically to yield the best estimate for the six cases. The fact that the blood flow through the mitral valve in vivo represents a pulsatile system whereas the Gorlin formula was derived for steady-state conditions and yet yields in vivo correlations with autopsy measurements at a level of r=0.92 suggests that a steady-state approximation to the pulsatile system for the heart is valid.

A fundamental assumption of the original theory of Gorlin and Gorlin is that the mitral valve orifice area is constant for any one patient in the absence of an acute rheumatic process. Nevertheless, valve area computations in resting and exercise states often reveal differences in the computed valve areas. The original data of Gorlin and Gorlin revealed an average valve area variation between rest and exercise conditions of 13%, corresponding to a standard error of 0.21 cm$^2$.

TABLE 1

Comparison of mitral valve area measured at autopsy and computed by the Gorlin formula with the predictions of the present theory using the original autopsy data of Gorlin and Gorlin.

| CASE | V | R | dp | t | $A_o$ | $A_G$ | $A_{EC}$ | $A_M$ | $A_N$ | $A_{EM}$ | $A_{EN}$ |
|---|---|---|---|---|---|---|---|---|---|---|---|
| 1 | 51 | 106 | 22 | 0.25 | 1.40 | 1.40 | 1.45 | 1.25 | 1.50 | 1.30 | 1.45 |
| 2 | 33 | 94 | 24 | 0.34 | 0.75 | 0.06 | 0.65 | 0.60 | 0.65 | 0.60 | 0.60 |
| 3 | 33 | 82 | 25 | 0.36 | 0.70 | 0.60 | 0.60 | 0.45 | 0.80 | 0.50 | 0.70 |
| 4 | 40 | 79 | 16 | 0.44 | 0.60 | 0.80 | 0.75 | 0.75 | 0.70 | 0.75 | 0.75 |

TABLE 1-continued

Comparison of mitral valve area measured at autopsy and computed by the Gorlin formula with the predictions of the present theory using the original autopsy data of Gorlin and Gorlin.

| CASE | V | R | dp | t | $A_o$ | $A_G$ | $A_{EC}$ | $A_M$ | $A_N$ | $A_{EM}$ | $A_{EN}$ |
|---|---|---|---|---|---|---|---|---|---|---|---|
| 5 | 30 | 105 | 23 | 0.36 | 0.55 | 0.40 | 0.45 | 0.35 | 0.45 | 0.40 | 0.40 |
| MEAN | | | | | 0.76 | 0.73 | 0.75 | 0.67 | 0.76 | 0.71 | 0.73 |
| SE($A_o$; $A_G$, $A_{EC}$, $A_M$, $A_N$, $A_{EN}$) | | | | | | 0.11 | 0.09 | 0.18 | 0.10 | 0.11 | 0.11 |
| r | | | | | | 0.92 | 0.95 | 0.85 | 0.97 | 0.94 | 0.95 |
| SE($A_G$; $A_{EC}$, $A_M$, $A_N$, $A_{EM}$, $A_{EN}$) | | | | | | | 0.03 | 0.10 | 0.13 | 0.07 | 0.06 |
| r | | | | | | | 0.99 | 0.96 | 0.95 | 0.99 | 0.98 |

V = stroke volume from Fick principle, R = heart frequency, dp = mitral valve gradient in mm Hg, t = diastolic filling period in sec/beat, $A_o$ = mitral valve area measured at autopsy, $A_G$ = valve area from Gorlin formula, $A_{EC}$ = valve area from Euler-continuity equation (1.37), $A_M$ = valve area from inertial component of the Euler-continuity equation (1.58), $A_N$ = area from the pressure independent orifice equation (1.65), $A_{EM}$ = area from equation (1.66), $A_{EN}$ = valve area from equation (1.67), SE = standard error (cm²), r = correlation coefficient. Stroke volume is given in ml and area in cm².

TABLE 2

Matrix expressing correlation coefficients and standard errors relating autopsy measurements and areas calculated by the Gorlin formula with the present theory.

| SE\r | $A_0$ | $A_G$ | $A_{EC}$ | $A_M$ | $A_N$ | $A_{EM}$ | $A_{EN}$ |
|---|---|---|---|---|---|---|---|
| $A_0$ | D | .92 | .95 | .85 | .97 | .94 | .95 |
| $A_G$ | .11 | D | .99 | .96 | .95 | .98 | .98 |
| $A_{EC}$ | .09 | .03 | D | .95 | .95 | .98 | .98 |
| $A_M$ | .18 | .10 | .10 | D | .84 | .99 | .90 |
| $A_N$ | .10 | .13 | .10 | .21 | D | .94 | .99 |
| $A_{EM}$ | .11 | .07 | .08 | .08 | .15 | D | .99 |
| $A_{EN}$ | .11 | .06 | .06 | .15 | .05 | .07 | D |

Intersection of a given row and column yields the value of r or SE. Elements above the diagonal represent standard errors in cm². Symbol designations are as in Table 1.

It is not difficult, however, to attribute errors of this magnitude to measurement uncertainties in heart frequency, diastolic filling period, cardiac output, and mitral valve gradient. A recent investigation using prosthetic mitral valves in a pulsatile flow chamber demonstrated that orifice areas computed by the Gorlin formula can vary up to 2.8% per flow unit for flows between 10 to 30 liters per minute. The comparable change in the resting and exercise state mitral valve areas from the original data of Gorlin and Gorlin is 10% per flow unit. This suggests that clinical measurement uncertainties contribute to the difference in resting and exercise state valve areas.

The expected maximum error in an area measurement via the Gorlin formula is given by:

$$dA/A = dV/V + dt/t + (\tfrac{1}{2})dp/p \quad (1.68)$$

where dA/a, dV/V, dt/t, and dp/p are the fractional errors in area, stroke volume, diastolic filling period, and pressure gradient, respectively. Estimating errors in stroke volume determination at 5%, filling period at 10%, and pressure differential at 15% would indicate a maximum expected error of 30%. The error in the pressure measurement may be greater than this, however. The basis for this view relates to the measurement techniques employed in the original study. Here the mitral valve gradient was taken to be reflected by the pulmonary capillary wedge pressure minus the left ventricular filling pressure. This filling pressure was not measured but assumed to be 5 mm Hg for all patients. Therefore, the effects of possible pressure inaccuracies should be reflected in the results of area computations by the various orifice area formulas developed above. The equations for the inertial component, $A_M$, and the pressure-independent equation, $A_N$, represent extreme cases of pressure dependence with the Gorlin formula, $A_G$, occupying an intermediate position. $A_M$ depends upon pressure differential, dp, to the power −1, $A_N$ demonstrates no explicit pressure dependence, and $A_G$ depends upon pressure to the power −½. Thus inaccuracies in dp would be expected to manifest themselves maximally in the equation for $A_M$, minimally in that for $_NA$, and at an intermediate position in that $_G$ for A. This theoretically expected behavior is observed in $A_M$, $A_N$, and $A_G$ with respect to the autopsy data as reflected in the correlation coefficients and standard errors of Table 1, whereby: $(r_{No}, SE_{No}) = (0.97, 0.10)$, $(r_{M,o}, SE_{M,o}) = (0.85, 0.18)$ and $(r_{G,o}, SE_{G,o}) = (0.92, 0.11)$, respectively.

An additional source of discrepancy in valve area calculations as computed by the various formulas relates to the dependence on heart frequency. In the Gorlin formula, heart frequency R enters through the need to compute filling volume as the cardiac output divided by heart frequency. Thus heart frequency appears in $A_G$ to the power −1. The pressure-independent equation for $A_N$ depends upon heart frequency to the power −3, and the inertial component equation for $A_M$, depends on heart frequency to the power +1. The equations for $A_{EM}$ and $A_N$ depend upon heart frequency to the power 0 and −1, respectively. These considerations assume that cardiac output is the primary variable and stroke volume is derived from it by division by heart frequency.

Inaccuracies in the measurement of this variable thus influence the area computations according to its power in the respective orifice equations. Particularly significant in this respect is the dependence of $A_M$ and $A_M$ on heart frequency. $A_M$ depends on this variable to the power +1, while $A_N$ has a −3 dependence on R. Thus an error resulting in an overestimate of R by 10% has the effect of overestimating the area of $A_M$ relative to $A_N$ by 40%.

Like considerations apply to the other orifice equations with respect to heart frequency and the other hemodynamic variables. This effect may be appreciated by comparing the correlation coefficients between $A_M$ and $A_N$ relative to the other correlation coefficients in this series.

Comparison of the Predictions of the Present Theory with Measurements on Excised Mitral Valves In this investigation, 13 records from the Department di Cardiologist della Institute Ospitalieri di Verona for patients undergoing preoperative cardiac catheterization for mitral stenosis and prosthetic valve replacement were analyzed. The catheterization study provided the hemodynamic data required for area computations using the current theory. The orifice area of the intact stenotic mitral valve was measured geometrically by means of a conical (frustrum conoid) sizing apparatus in much the same manner as known in the art. This sizer had an elliptical cross-sectional area and was partitioned along its length by recessed markers preset to specify area differences of 0.1 cm$^2$. The sizer was guided snugly into the orifice from the atrial surface and positioned into the irregular ring of the valve so as to optimally adjust the orifice to the elliptical cross section of the conoid. The results of this study are summarized in Tables 3 and 4.

the stenotic mitral valve, particularly when irregularities in the leaflets or mitral ring are present.

These possible sources of error can be appreciated by comparing the correlation coefficients between the anatomical sizer measurements and the Gorlin/anatomic measurements or the two-dimensional area measurements whereby the comparisons with the sizer anatomic determinations display a consistently lower correlation than the data of either Table 2 or 6. Despite the generally reduced correlation, the relative relationship between the correlation coefficients in these three cases corresponds.

TABLE 3

Comparison of mitral valve area geometrically measured from excised valve specimens by a fustrum conid sized apparatus and the Gorlin formula with the predictions of the current theory.

| CASE | V | R | dp | t | $A_o$ | $A_G$ | $A_{EC}$ | $A_M$ | $A_N$ | $A_{EM}$ | $A_{EN}$ |
|---|---|---|---|---|---|---|---|---|---|---|---|
| 1 | 57.4 | 80 | 7 | .350 | 1.70 | 2.00 | 2.10 | 2.50 | 1.55 | 2.25 | 1.75 |
| 2 | 59.4 | 80 | 8 | .395 | 2.20 | 1.70 | 1.80 | 2.30 | 1.25 | 2.00 | 1.45 |
| 3 | 50.3 | 75 | 10 | .351 | 1.50 | 1.45 | 1.50 | 1.35 | 1.50 | 1.40 | 1.45 |
| 4 | 31.6 | 100 | 9 | .275 | 1.00 | 1.25 | 1.30 | 1.70 | 0.85 | 1.45 | 1.00 |
| 5 | 34.0 | 130 | 20 | .222 | 1.10 | 1.10 | 1.15 | 1.35 | 0.85 | 1.20 | 0.95 |
| 6 | 23.7 | 140 | 17 | .170 | 1.50 | 1.10 | 1.15 | 1.30 | 0.95 | 1.20 | 1.10 |
| 7 | 51.3 | 75 | 15 | .450 | 1.50 | 0.95 | 1.00 | 0.90 | 0.95 | 0.90 | 0.95 |
| 8 | 34.4 | 120 | 30 | .227 | 1.10 | 0.90 | 0.90 | 0.80 | 0.95 | 0.85 | 0.90 |
| 9 | 18.5 | 136 | 20 | .136 | 1.35 | 1.00 | 1.00 | 0.80 | 1.15 | 0.90 | 1.05 |
| 10 | 5.4 | 86 | 30 | .373 | 0.80 | 0.60 | 0.60 | 0.45 | 0.75 | 0.50 | 0.65 |
| 11 | 33 | 70 | 25 | .404 | 1.00 | 0.55 | 0.55 | 0.30 | 0.85 | 0.40 | 0.70 |
| 12 | 28.7 | 70 | 18 | .521 | 0.90 | 0.40 | 0.45 | 0.40 | 0.45 | 0.40 | 0.40 |
| 13 | 16.1 | 140 | 34 | .214 | 0.70 | 0.40 | 0.45 | 0.45 | 0.40 | 0.40 | 0.40 |
| MEAN | | | | | 1.26 | 1.02 | 1.07 | 1.12 | 0.95 | 1.06 | 0.97 |
| SE($A_o$; $A_G$, $A_{EC}$, $A_M$, $A_N$, $A_{EM}$, $A_{EN}$) | | | | | | 0.35 | 0.33 | 0.47 | 0.39 | 0.36 | 0.32 |
| r | | | | | | 0.82 | 0.82 | 0.78 | 0.78 | 0.83 | 0.83 |
| SE($A_G$; $A_{EC}$, $A_M$, $A_N$, $A_{EM}$, $A_{EN}$) | | | | | | | 0.04 | 0.26 | 0.24 | 0.14 | 0.98 |

$A_o$ = mitral valve area measured by conoid sizing apparatus (cm$^2$). Remaining symbols as in Table 1.

TABLE 4

Matrix expressing correlation coefficients and standard errors relating the anatomic sizer measurements and the results of the Gorlin formula computation with the predictions of the present theory.

| SE/r | $A_0$ | $A_G$ | $A_{EC}$ | $A_M$ | $A_N$ | $A_{EM}$ | $A_{EN}$ |
|---|---|---|---|---|---|---|---|
| $A_0$ | D | .82 | .82 | .78 | .78 | .83 | .83 |
| $A_G$ | .35 | D | .99 | .95 | .88 | .98 | .97 |
| $A_{EC}$ | .33 | .04 | D | .97 | .87 | .98 | .98 |
| $A_M$ | .47 | .26 | .24 | D | .72 | .99 | .87 |
| $A_N$ | .39 | .24 | .29 | .53 | D | .79 | .96 |
| $A_{EM}$ | .36 | .14 | .15 | .42 | .11 | D | .93 |
| $A_{EN}$ | .32 | .13 | .14 | .42 | .11 | .27 | D |

Symbol designations as in Table 3.

The interobserver correlation coefficient for the sizer measurements was r=0.99; thus the geometric measurement using this apparatus was highly reproducible. Despite this high level of reproducibility, certain criticisms may be directed at this measurement approach. First, in vivo, the stenotic mitral valve leaflets open to a degree determined by the dynamics of the blood flow through the orifice. The application of a mechanical force by the body of the sizing apparatus represents a force of a rather different nature than that applied by the uniform motion of fluid pressure. Second, the mechanical sizer, being uniformly elliptical in cross-sectional area, may not precisely conform to the orifice of Comparison of the Present Theory with Mitral Orifice Area Measurements from Two-Dimensional Echocardiography The patients admitted to this study presented at the Division of Cardiology of the University of Geneve Hospital during the period of October 1977 to October 1979. The patients accepted for evaluation purposes were those whose initial clinical evaluation suggested a diagnosis of predominant mitral stenosis so that comparisons with the Gorlin formula would be valid. The initial group comprised 50 patients. Of this consecutive series, 45 of the catheterization studies and 44 of the 2D echocardiographic studies provided information of sufficient technical quality to be used in the test of the theory of the present invention.

Visualization of the mitral value orifice was achieved by a mechanical sector scanning Smith-Kline 2.25 MHz transducer offering an angle of vision between 30 and 82 degrees. The real-time image of the mitral valve could be frozen in time for measurement purposes with a Sanyo VIC 7100 video replay apparatus. The mitral valve image was then realized for planimetric purposes by placing a transparent paper directly on the video screen and tracing the outline of the mitral orifice on the paper. The mitral valve was visualized in the short-axis configuration using a known technique. The echographic measurements were performed without knowing the results of the hemodynamic orifice area calculation.

Hemodynamic measurements comprised simultaneous right and left heart catheterization. The capillary wedge pressure was assumed to reflect left atrial pressure, and the filling pressure was taken as the average left ventricular pressure measured in diastole. Cardiac output was determined by the standard Fick principle method, and the diastolic filling period was measured from the simultaneous right and left pressure tracings. The mitral valve gradient was then determined as the capillary wedge pressure minus the average left ventricular pressure during the diastolic filling period. The mitral valve area was then computed from the standard Gorlin formula and the present theory.

The results of the analysis are summarized in Tables 5 and 6. The correlations achieved in comparison with the bidimensional echographic measured areas and those computed by the present theory compare favorably with those achieved by the results of the original Gorlin autopsy measurements and the direct sizer measurements of excised mitral valves. While the overall correlation for areas derived via two-dimensional echocardiography and the various ori-

TABLE 6

Matrix expressing correlation coefficients and standard errors relating bi-dimensional echocardiographic measurements, Gorlin formula computed areas, and the predictions of the present theory.

| SE/r | $A_O$ | $A_G$ | $A_{EC}$ | $A_M$ | $A_N$ | $A_{EM}$ | $A_{EN}$ |
|---|---|---|---|---|---|---|---|
| $A_O$ | D | .94 | .94 | .75 | .85 | .89 | .90 |
| $A_G$ | .24 | D | .99 | .81 | .91 | .95 | .97 |
| $A_{EC}$ | .26 | .05 | D | .81 | .91 | .95 | .97 |
| $A_M$ | .43 | .43 | .46 | D | .51 | .94 | .70 |
| $A_N$ | .44 | .31 | .33 | .72 | D | .76 | .95 |
| $A_{EM}$ | .26 | .12 | .13 | .25 | .48 | D | .88 |
| $A_{EN}$ | .31 | .15 | .16 | .25 | .21 | .31 | D |

Symbol designations as in Table 5.

TABLE 5

Comparison of mitral valve area measured from bi-dimensional echocardiography and computed by the Gorlin formula with predictions of the present theory.

| CASE | V | R | dp | t | Ao | $A_G$ | $A_{EC}$ | $A_M$ | $A_N$ | $A_{EM}$ | $A_{EN}$ |
|---|---|---|---|---|---|---|---|---|---|---|---|
| 1 | 56 | 110 | 10.6 | .186 | 3.40 | 3.00 | 3.10 | 3.05 | 2.80 | 3.00 | 2.90 |
| 2 | 49 | 96 | 8.4 | .195 | 3.20 | 2.80 | 2.90 | 2.60 | 2.95 | 2.70 | 2.85 |
| 3 | 53 | 96 | 8.5 | .217 | — | 2.70 | 2.80 | 2.75 | 2.55 | 2.70 | 2.60 |
| 4 | 45 | 93 | 6.0 | .269 | 1.90 | 2.20 | 2.30 | 3.10 | 1.50 | 2.60 | 1.80 |
| 5 | 91 | 70 | 9.0 | .467 | 2.20 | 2.10 | 2.20 | 2.35 | 1.80 | 2.20 | 1.95 |
| 6 | 73 | 100 | 17.7 | .280 | 1.90 | 2.00 | 2.05 | 1.95 | 1.95 | 2.00 | 2.00 |
| 7 | 91 | 75 | 12.6 | .433 | 1.80 | 1.90 | 2.00 | 1.95 | 1.80 | 1.90 | 1.85 |
| 8 | 104 | 64 | 9.4 | .612 | 2.00 | 1.80 | 1.85 | 2.15 | 1.40 | 1.95 | 1.60 |
| 9 | 102 | 74 | 18.8 | .463 | 2.20 | 1.80 | 1.85 | 1.55 | 2.00 | 1.65 | 1.90 |
| 10 | 54 | 80 | 12.5 | .288 | 1.45 | 1.70 | 1.75 | 1.30 | 2.15 | 1.50 | 1.90 |
| 11 | 85 | 68 | 12.2 | .463 | 1.75 | 1.70 | 1.75 | 1.55 | 1.80 | 1.60 | 1.75 |
| 12 | 56 | 70 | 10.6 | .368 | 1.90 | 1.50 | 1.55 | 1.25 | 1.75 | 1.35 | 1.60 |
| 13 | 59 | 74 | 9.0 | .487 | 1.70 | 1.30 | 1.35 | 1.70 | 0.95 | 1.50 | 1.15 |
| 14 | 102 | 49 | 8.1 | .771 | 1.50 | 1.50 | 1.55 | 1.45 | 1.50 | 1.50 | 1.50 |
| 15 | 76 | 56 | 7.3 | .603 | 1.70 | 1.50 | 1.60 | 2.15 | 1.00 | 1.80 | 1.25 |
| 16 | 61 | 72 | 11.6 | .412 | 1.50 | 1.40 | 1.45 | 1.30 | 1.45 | 1.35 | 1.40 |
| 17 | 46 | 94 | 8.2 | .368 | 1.40 | 1.40 | 1.50 | 2.35 | 0.80 | 1.80 | 1.05 |
| 18 | 96 | 55 | 10.3 | .745 | 1.40 | 1.30 | 1.35 | 1.35 | 1.20 | 1.30 | 1.25 |
| 19 | 50 | 82 | 10.4 | .385 | 1.20 | 1.30 | 1.35 | 1.55 | 1.05 | 1.40 | 1.15 |
| 20 | 52 | 80 | 9.3 | .426 | 1.50 | 1.30 | 1.35 | 1.70 | 0.95 | 1.50 | 1.10 |
| 21 | 44 | 94 | 8.5 | .371 | 1.50 | 1.30 | 1.40 | 2.20 | 0.75 | 1.70 | 1.00 |
| 22 | 59 | 80 | 13.1 | .418 | 1.40 | 1.25 | 1.30 | 1.40 | 1.10 | 1.30 | 1.15 |
| 23 | 49 | 90 | 10.9 | .377 | 1.50 | 1.25 | 1.35 | 1.75 | 0.90 | 1.45 | 1.05 |
| 24 | 61 | 75 | 8.9 | .552 | 1.50 | 1.20 | 1.25 | 1.85 | 0.75 | 1.45 | 0.90 |
| 25 | 49 | 72 | 11.5 | .461 | 1.40 | 1.00 | 1.05 | 1.05 | 0.95 | 1.00 | 1.00 |
| 26 | 52 | 80 | 21.7 | .363 | 0.90 | 1.00 | 1.00 | 0.75 | 1.30 | 0.85 | 0.90 |
| 27 | 83 | 65 | 12.2 | .767 | 1.20 | 1.00 | 1.05 | 1.35 | 0.70 | 1.15 | 1.05 |
| 28 | 55 | 94 | 10.9 | .540 | 1.20 | 1.00 | 1.10 | 2.15 | 0.45 | 1.45 | 1.20 |
| 29 | 55 | 84 | 12.5 | .500 | 0.80 | 1.00 | 1.05 | 1.50 | 0.65 | 1.20 | 1.10 |
| 30 | 50 | 76 | 12.3 | .461 | 1.00 | 1.00 | 1.05 | 1.10 | 0.85 | 1.05 | 1.00 |
| 31 | 53 | 72 | 10.8 | .516 | 1.30 | 1.00 | 1.05 | 1.20 | 0.80 | 1.00 | 1.05 |
| 32 | 59 | 75 | 13.6 | .540 | 0.80 | 0.95 | 1.00 | 1.15 | 0.75 | 1.05 | 1.00 |
| 33 | 49 | 70 | 11.1 | .494 | 1.00 | 0.95 | 1.00 | 1.05 | 0.85 | 1.00 | 0.95 |
| 34 | 36 | 100 | 14.9 | .317 | 0.90 | 0.95 | 1.00 | 1.15 | 0.75 | 1.05 | 1.00 |
| 35 | 65 | 74 | 19.4 | .527 | 1.20 | 0.90 | 0.95 | 0.90 | 0.90 | 0.90 | 0.90 |
| 36 | 35 | 88 | 21.1 | .306 | 1.10 | 0.80 | 0.80 | 0.60 | 1.00 | 0.70 | 0.75 |
| 37 | 56 | 80 | 16.8 | .553 | 0.90 | 0.85 | 0.85 | 1.00 | 0.65 | 0.90 | 0.70 |
| 38 | 44 | 82 | 17.9 | .476 | 1.10 | 0.70 | 0.75 | 0.80 | 0.60 | 0.75 | 0.70 |
| 39 | 44 | 110 | 13.4 | .550 | 1.10 | 0.70 | 0.80 | 1.90 | 0.25 | 1.15 | 0.75 |
| 41 | 23 | 120 | 29.5 | .190 | 0.90 | 0.70 | 0.75 | 0.55 | 0.90 | 0.60 | 0.80 |
| 42 | 34 | 80 | 10.2 | .525 | 1.00 | 0.65 | 0.70 | 1.00 | 0.40 | 0.80 | 0.50 |
| 43 | 63 | 68 | 18.1 | .798 | 0.80 | 0.60 | 0.60 | 0.75 | 0.45 | 0.65 | 0.60 |
| MEAN | | | | | 1.45 | 1.30 | 1.40 | 1.52 | 1.15 | 1.39 | 1.25 |
| SE($A_O$; $A_G$, $A_{EG}$, $A_M$, $A_N$, $A_{EM}$, $A_{EN}$) | | | | | | 0.24 | 0.26 | 0.43 | 0.44 | 0.26 | 0.31 |
| r | | | | | | 0.94 | 0.94 | 0.75 | 0.85 | 0.89 | 0.90 |
| SE($A_G$; $A_{EC}$, $A_M$, $A_N$, $A_{EM}$, $A_{EN}$) | | | | | | | 0.05 | 0.43 | 0.31 | 0.12 | 0.15 |
| r | | | | | | | 0.99 | 0.81 | 0.91 | 0.95 | 0.99 |

$A_o$ = valve area measured planigraphically from the 2D echocardiographic screen.
Remaining symbols as in Table 1.

fice equations are comparable for the hemodynamic and rhythmic states of Table 5, the two-dimensional echographic method yields a high specificity and a low false positive rate in comparison to the Gorlin formula. The equation for $A_N$, on the other hand, yields a low false negative rate and a high false positive rate in comparison with the Gorlin formula and 2D planimetry. A false positive is here defined as a valve area less than 1 cm² as computed by the Gorlin formula. It seems unlikely that the hemodynamic alterations of mitral regurgitation are sufficient to explain this discrepancy, as the correlation coefficient for all cases as compared with pure mitral stenosis correspond closely. A possibility is that 2D echocardiography may tend to consistently overestimate the orifice area due to its sensitivity to contrast settings or the difficulties of planigraphically measuring irregular valve margins, particularly in the presence of small orifice areas.

Previously reported studies have suggested that mitral valve calcification represents the singlemost important source of error in a 2D echographic determination of mitral valve orifice area. The presence of calcium deposits tend to yield underestimates of mitral valve area relative to catheterization. This would tend to lead to a high false positive rate, which is not the case in the present echographic study. A previous study found that 2D echocardiography correlated with direct anatomic measurements of excised valves at a level of r=0.83, SE=0.54 cm², N=19 for noncalcified valves and at a level of r=0.78, SE=0.60 cm², N=29 when 10 calcified valves were included. This appears to suggest that valvular calcification was not the principal source of the high false negative rate of the present echographic study relative to catheterization.

In an effort to further delineate the source of this high false negative rate, the data of Table may be subdivided according to the 14 largest areas (>1.3 cm²) in pure mitral stenosis and the 14 smallest areas in pure mitral stenosis and the relevant statistical parameters in each group computed. The correlations between catheterization and 2D echocardiography between the large-area and small-area groups were found to be r=0.89 and r=0.34, respectively. Subdividing the 29 cases reported into large- and small-area groups reveals that the correlations between anatomical area measurements of excised valves and 2D planimetry for the large (>1.5 cm²) and small-area groups were r=0.64, N=14 and r=0.13, N=14, respectively. 50% of the small-area valves were calcified in this study, which may account for the insignificant correlation in the small-area group.

These results suggest that 2D echography may enjoy its greatest predictive capacity for valve areas associated with mitral stenosis of less than clinical grade II.

Comparison of the Present Theory with the Area Predictions of the Gorlin Formula Valve area computed by the Gorlin formula is the standard by which valvular stenosis is assessed in the cardiac catheterization laboratory. Area calculated by the Gorlin formula correlates with autopsy-measured area at a level of r=0.92, N=6. Additionally, several published studies have confirmed correlations in the vicinity of r=0.90 in comparing Gorlin-formula-derived valve areas from catheterization data with the results of bidimensional echocardiography. Thus comparison with the Gorlin model as a secondary standard represents a significant test of a cardiac valve orifice area theory.

In the present study 23 randomly chosen records from the Stanford University Hospital of patients undergoing cardiac catheterization for the evaluation of mitral stenosis were evaluated. A second set of records consisted of the 23 resting-state catheterization studies from the original investigation of Gorlin and Gorlin. The results of this analysis are presented in Tables 7–10.

In both Tables 8 and 10 the correlations of the area equations and their respective intercorrelations are at a similar level, with the exception of $r(A_M, A_N)$, which is about 10% lower. Further, inspection of the $A_G$, $A_M$, and $A_N$ values of all the tables reveal that, in comparison with $A_G$, the area values of $A_M$ tend to be greater than $A_G$ when $A_N$ is less than $A_G$. This can be understood by the functional dependence of $A_M$ and $A_N$ on heart frequency, as previously discussed.

One of the important factors influencing the accuracy of the catheterization-derived valve area computation relates to the accuracy of the pressure measurement. This variable becomes potentially significant in the Gorlin formula and equations involving explicit pressure dependence. This may be appreciated by noting that, for a gradient measurement whose fundamental uncertainty is 1½ mm Hg, the error for a mitral gradient measurement of less than 6 mm Hg is greater than 25%. Such an uncertainty produces a computational error in the valve area of 25% in the equation for $A_M$ and 12½% in the equation for $A_G$.

A further factor affecting the value of the catheterization-derived area is that relatively large areas are associated with low valve gradients. In this case the majority of the flow occurs during the early portions of the diastolic filling period. If the pressure gradient is averaged over the entire diastolic filling period without adjusting the averaging process according to the magnitude of the flow at the given point in the flow interval, an inappropriately low average pressure gradient will be calculated. This low value of the mitral valve gradient yields an excessively large valve area in all the area equations that depend on pressure.

TABLE 7

Comparison of mitral valve area as computed by the Gorlin formula with value area computed by the present theory using the original catheterization data of Gorlin and Gorlin.

| CASE | V | R | dp | t | $A_G$ | $A_{EC}$ | $A_M$ | $A_N$ | $A_{EM}$ | $A_{EN}$ |
|---|---|---|---|---|---|---|---|---|---|---|
| 1 | 94 | 100 | 13.8 | .31 | 2.65 | 2.75 | 3.25 | 2.05 | 2.95 | 2.35 |
| 2 | 90 | 72 | 16 | .47 | 1.55 | 1.60 | 1.40 | 1.65 | 1.45 | 1.55 |
| 3 | 53 | 90 | 15 | .31 | 1.40 | 1.45 | 1.35 | 1.40 | 1.35 | 1.40 |
| 4 | 50 | 106 | 22 | .25 | 1.35 | 1.40 | 1.20 | 1.50 | 1.25 | 1.40 |
| 5 | 41 | 107 | 20 | .23 | 1.30 | 11.35 | 1.10 | 1.40 | 1.20 | 1.35 |
| 6 | 70 | 100 | 27 | .40 | 1.10 | 1.15 | 1.25 | 0.90 | 0.95 | 1.00 |
| 7 | 42 | 105 | 27 | .33 | 0.80 | 0.80 | 0.80 | 0.75 | 0.80 | 0.80 |
| 8 | 49 | 108 | 34 | .31 | 0.85 | 0.90 | 0.80 | 0.90 | 0.80 | 0.85 |
| 9 | 63 | 70 | 19 | .52 | 0.90 | 0.90 | 0.75 | 1.00 | 0.80 | 0.95 |
| 10 | 33 | 96 | 12 | .40 | 0.80 | 0.85 | 0.85 | 0.80 | 0.80 | 0.80 |
| 11 | 45 | 79 | 16 | .44 | 0.80 | 0.85 | 0.85 | 0.80 | 0.80 | 0.80 |

TABLE 7-continued

Comparison of mitral valve area as computed by the Gorlin formula with value area computed by the present theory using the original catheterization data of Gorlin and Gorlin.

| CASE | V | R | dp | t | $A_G$ | $A_{EC}$ | $A_M$ | $A_N$ | $A_{EM}$ | $A_{EN}$ |
|---|---|---|---|---|---|---|---|---|---|---|
| 12 | 48.5 | 80 | 21 | .50 | 0.70 | 0.70 | 0.70 | 0.65 | 0.70 | 0.65 |
| 13 | 37 | 84 | 23 | .44 | 0.55 | 0.60 | 0.55 | 0.55 | 0.55 | 0.55 |
| 14 | 25 | 140 | 31 | .23 | 0.60 | 0.65 | 0.75 | 0.50 | 0.70 | 0.55 |
| 15 | 33 | 94 | 24 | .34 | 0.65 | 0.65 | 0.60 | 0.65 | 0.65 | 0.65 |
| 16 | 33 | 82 | 25 | .36 | 0.60 | 0.60 | 0.40 | 0.80 | 0.50 | 0.70 |
| 17 | 40 | 105 | 49 | .32 | 0.55 | 0.60 | 0.45 | 0.75 | 0.50 | 0.65 |
| 18 | 46.5 | 75 | 29 | .49 | 0.55 | 0.60 | 0.45 | 0.70 | 0.50 | 0.60 |
| 19 | 30.5 | 105 | 23 | .36 | 0.55 | 0.60 | 0.70 | 0.45 | 0.60 | 0.50 |
| 20 | 12 | 204 | 41 | .13 | 0.45 | 0.50 | 0.60 | 0.35 | 0.50 | 0.40 |
| 21 | 32.5 | 80 | 18 | .50 | 0.50 | 0.50 | 0.55 | 0.40 | 0.50 | 0.45 |
| 22 | 41 | 56 | 17 | .77 | 0.45 | 0.45 | 0.50 | 0.40 | 0.45 | 0.45 |
| 23 | 30 | 100 | 30 | .40 | 0.45 | 0.45 | 0.50 | 0.40 | 0.45 | 0.45 |
| MEAN | | | | | 0.87 | 0.91 | 0.88 | 0.85 | 0.86 | 0.86 |
| SE($A_G$; $A_{EC}$; $A_M$; $A_N$; $A_{EM}$; $A_{EN}$) | | | | | | 0.03 | 0.16 | 0.16 | 0.08 | 0.07 |
| r | | | | | | 0.99 | 0.96 | 0.95 | 0.99 | 0.99 |

Symbol designations as in Table 1.

TABLE 8

Matrix expressing correlation coefficients and standard errors relating areas computed by the Gorlin formula and the present theory from the original hemodynamic data of Gorlin and Gorlin.

| SE/r | $A_G$ | $A_{EC}$ | $A_M$ | $A_N$ | $A_{EM}$ | $A_{EN}$ |
|---|---|---|---|---|---|---|
| $A_G$ | D | .99 | .96 | .95 | .99 | .99 |
| $A_{EC}$ | .03 | D | .96 | .95 | .99 | .99 |
| $A_M$ | .16 | .17 | D | .83 | .99 | .93 |
| $A_N$ | .16 | .17 | .32 | D | .89 | .98 |
| $A_{EM}$ | .08 | .08 | .08 | .24 | D | .96 |
| $A_{EN}$ | .07 | .07 | .23 | .08 | .15 | D |

Symbol designations as in Table 1.

TABLE 9

Comparison of mitral valve area as computed by the Gorlin formula with the predictions of the present theory from hemodynamic data derived from a series of cardiac catheterization studies from the Standford University Hospital.

| CASE | V | R | dp | t | $A_G$ | $A_{EC}$ | $A_M$ | $A_N$ | $A_{EM}$ | $A_{EN}$ |
|---|---|---|---|---|---|---|---|---|---|---|
| 1 | 52 | 100 | 10.1 | .22 | 2.40 | 2.50 | 2.45 | 2.25 | 2.40 | 2.30 |
| 2 | 40 | 95 | 8.8 | .28 | 1.55 | 1.65 | 1.95 | 1.20 | 1.75 | 1.35 |
| 3 | 56 | 75 | 8.5 | .40 | 1.55 | 1.60 | 1.75 | 1.30 | 1.65 | 1.40 |
| 4 | 46 | 82 | 11.0 | .30 | 1.50 | 1.55 | 1.35 | 1.60 | 1.40 | 1.55 |
| 5 | 57 | 73 | 8.7 | .42 | 1.50 | 1.55 | 1.65 | 1.25 | 1.55 | 1.35 |
| 6 | 111 | 37 | 6.75 | 1.10 | 1.25 | 1.30 | 1.10 | 1.40 | 1.15 | 1.30 |
| 7 | 49 | 76 | 12.1 | .38 | 1.20 | 1.25 | 1.10 | 1.25 | 1.15 | 1.20 |
| 8 | 69 | 61 | 12.5 | .57 | 1.10 | 1.15 | 1100 | 1.20 | 1.05 | 1.15 |
| 9 | 36 | 77 | 13.9 | .40 | 0.75 | 0.80 | 0.75 | 0.80 | 0.75 | 0.80 |
| 10 | 37 | 103 | 15.6 | .29 | 0.95 | 1.00 | 1.00 | 0.85 | 0.95 | 0.90 |
| 11 | 43 | 83 | 16.7 | .36 | 0.95 | 0.95 | 0.85 | 1.00 | 0.90 | 0.95 |
| 12 | 50 | 70 | 16.3 | .47 | 0.85 | 0.85 | 0.70 | 0.95 | 0.80 | 0.90 |
| 13 | 36 | 97 | 16.5 | .36 | 0.80 | 0.85 | 1.00 | 0.60 | 0.90 | 0.70 |
| 14 | 53 | 56 | 10.7 | .66 | 0.80 | 0.80 | 0.75 | 0.80 | 0.80 | 0.80 |
| 15 | 47 | 66 | 17.7 | .48 | 0.75 | 0.75 | 0.55 | 1.00 | 0.65 | 0.85 |
| 16 | 41 | 65 | 12.8 | .50 | 0.75 | 0.75 | 0.65 | 0.80 | 0.70 | 0.75 |
| 17 | 39 | 72 | 19.1 | .41 | 0.70 | 0.70 | 0.50 | 0.95 | 0.60 | 0.80 |
| 18 | 26 | 84 | 18.2 | .33 | 0.60 | 0.60 | 0.50 | 0.70 | 0.55 | 0.65 |
| 19 | 45 | 75 | 32.1 | .47 | 0.55 | 0.55 | 0.40 | 0.75 | 0.50 | 0.65 |
| 20 | 24 | 102 | 202 | .35 | 0.50 | 0.50 | 0.60 | 0.40 | 0.55 | 0.45 |
| 21 | 49 | 51 | 19.2 | .72 | 0.50 | 0.50 | 0.30 | 0.75 | 0.40 | 0.60 |
| 22 | 36 | 66 | 23.1 | .49 | 0.50 | 0.50 | 0.30 | 0.70 | 0.40 | 0.60 |
| 23 | 14 | 109 | 21.3 | .24 | 0.40 | 0.40 | 0.35 | 0.40 | 0.40 | 0.40 |
| MEAN | | | | | 0.97 | 1.00 | 0.94 | 0.99 | 0.95 | 0.96 |
| SE($A_G$; $A_{EC}$, $A_M$, $A_N$, $A_{EM}$, $A_{EN}$) | | | | | | 0.03 | 0.16 | 0.17 | 0.08 | 0.08 |
| r | | | | | | 0.99 | 0.97 | 0.94 | 0.99 | 0.98 |

Symbol designations as in Table 1.

TABLE 10

Matrix expressing correlation coefficients and standard errors relating areas computed by the Gorlin formula and the present theory from catheterization studies performed at Standard University.

| SE/r | $A_G$ | $A_{EC}$ | $A_M$ | $A_N$ | $A_{EM}$ | $A_{EN}$ |
|---|---|---|---|---|---|---|
| $A_G$    | D   | .99 | .97 | .94 | .99 | .98 |
| $A_{EC}$ | .03 | D   | .97 | .94 | .99 | .98 |
| $A_M$    | .16 | .03 | D   | .82 | .99 | .91 |
| $A_N$    | .17 | .08 | .32 | D   | .87 | .99 |
| $A_{EM}$ | .08 | .09 | .08 | .24 | D   | .95 |
| $A_{EN}$ | .08 | .09 | .24 | .08 | .16 | D   |

Symbol designations as in Table 2.

Previous investigations have related the mitral valve flow half-time and valve area and found that in nonstenotic valves, the predominant flow occurred in less than 25 msec. If, for example, the total diastolic flow interval lasts 300 msec and the predominant flow occurs within 30 msec, the pressure differential as computed by simple averaging over the full diastolic flow interval will be erroneously low in the absence of a correct weighting procedure.

A possible error of this nature may be suggested by case 1 of Table 3. Here the mitral gradient is relatively low, and the corresponding valve areas are significantly greater than the anatomically measured values, with the greatest valve area being associated with the equation for $A_M$, consistent with its greater pressure sensitivity. This trend appears to be reflected in the average values of area for the 13 cases considered in Table 3.

A further source of error in the pressure measurement has been studied in a series of open chest dogs. This investigation demonstrated regional pressure differences between the apex and base during diastole of 2.1±0.5 mm Hg, with a range of 0 to 9 mm Hg. These spatial pressure variations appear to be a result of turbulent eddies in the ventricle during the filling period.

Conclusions

1. Flow through the mitral valve may be represented by the motion of an inviscid fluid characterized by the Euler equation and the equation of continuity.

2. An orifice area solution of the Euler-continuity equation for valve area is expressed by two components: one representing the steady-flow component, the other an inertial or pulsatile component.

3. Both component solutions of the Euler-continuity equation yield a valid orifice area formula, agreeing with independent orifice area measurements within the limits of clinical measurement error.

4. Simultaneous solution of the component equations leads to an orifice equation suppressing explicit dependence on the valvular flow pressure differential, depending only on heart frequency, flow interval, and flow volume.

2. Noninvasive Assessment of Effective Natural and Prosthetic Aortic Valve Area Development of the Concept The Gorlin formula for aortic valve area in conditions of stenosis is:

$$A = V(44.5t)^{-1}(dP)^{-1/2} \qquad (2.1)$$

where A is the aortic valve area in $cm^2$, V is the stroke volume in $cm^3$, t is the systolic ejection period in sec, dP is the average aortic valve pressure gradient in mm Hg, and 44.5 is an orifice discharge coefficient derived from experimental measurements.

To achieve a noninvasive area expression, the pressure gradient in the area expression (2.1) must be eliminated. To do this another fundamental area expression independent of the Gorlin formula must be demonstrated and validated that can be combined with it in such a way as to eliminate the explicit pressure dependence.

A flow equation frequently employed by cardiologists for the computation of vascular impedance will be shown to possess the desired properties. This flow equation is:

$$P = kZQ \qquad (2.2)$$

where dP is the average pressure difference across the obstruction, k is a constant of proportionality relating the variables, Z is the impedance of the flow system considered, and Q is the flow through the obstruction. Equation (2.2) is frequently employed to compute systemic and pulmonary vascular resistance. In these conditions dP is interpreted as the pressure drop across the systemic or pulmonary vascular tree, Z is considered to be the steady flow resistance, and Q is the cardiac output. Equation (2.2) is a fundamental flow equation and may be applied to determine flow in pulsatile or time-varying systems such as cardiac valves if the impedance is generalized to encompass frequency-dependent effects.

The magnitude of the impedance of a pulsatile flow system may be expressed by a general concept from classical physics as:

$$z = [R^2 + (Iw - 1I/wC)^2]^{1/2} \qquad (2.3)$$

In this generalized expression for the magnitude of impedance, R is interpreted as the resistance factor due to steady flow across the obstruction, Iw is the contribution to total impedance due to inertial properties of the fluid transmitted and is known as the inertial reactance of the obstruction. The term 1/wC is the reactance of elastic distensibility. In both the reactance terms, w is the circular frequency of the pulsatile flow.

To apply this general concept of flow impedance to the aortic valve, we must properly associate an aspect of aortic valvular flow with each of the three impedance terms of eq. (2.3) and evaluate its contribution to the total impedance Z. This will result in an orifice equation specific to the aortic valve, independent of the Gorlin equation.

The resistive term R quantifies the hindrance to the flow resulting from energy dissipated in heat and mediated through blood viscosity. This term represents the steady-flow component of the overall impedance. In the original theory of Gorlin and Gorlin, this term was incorporated into the model by means of an empirically derived multiplicative discharge coefficient. The flow mechanisms of aortic stenosis have been studied by means of a theoretical model and flow experiments in artificial aortic valves. These investigations have substantiated the concept that the resistance term may be modeled by a multiplicative factor through the discharge coefficient as in the original theory of Gorlin and Gorlin. Similar results were shown by theoretical analysis and flow experiments through prosthetic aortic valves. This work indicates that the dominant character of the flow is affected by factors other than the resistance.

In the present formulation we assume that the resistance factor R is small relative to the remaining reactance terms and that it may be incorporated into the orifice discharge coefficient as a proportionality factor, as in the original model of Gorlin and Gorlin.

The reactance of structural distensibility, 1/wC, is proportional to the compliance of the structure confining the flow. For a highly rigid structure the elastic distensibility factor C is large, and hence the reactance of elastic distensibility, 1/wC, is small for normal values of the frequency w (proportional to the heart frequency). The compliance of the valvular structure can be estimated by measuring the structural distention of excised human aortic valves in simulated flow conditions. Such measurements have been published in which a human aortic valve was mounted in a pulsatile pressure chamber and cinephotographs of its action were taken under realistic flow conditions. Planigraphic measurements of the photographs reveal that the aortic valve annulus may be considered a rigid structure whose distensibility is less than 5% over the cardiac cycle. These published experimental results suggest that the elastic reactance term, 1/wC, is small relative to the total valvular impedance.

This approximation permits eq. (2.3) to be expressed as $Z=k_1 k_2 wI$, where $k_2$ is a constant incorporating the effects of resistance and $k_1$ is a constant incorporating the effects of the inertial reactance term.

The remaining impedance term is the inertial reactance, Iw. From the fundamental equations of classical fluid mechanics it is known that the conductance per unit pressure difference of a fluid through an orifice of cross-sectional area A is directly proportional to this area. By definition the impedance is the reciprocal of the conductance. Thus the impedance of inertial reactance per unit frequency must be proportional to the reciprocal of the cross-sectional area. The results thus far indicate that the flow impedance is predominantly specified by the term Iw and that the inertial reactance per unit frequency is proportional to the reciprocal of the orifice cross-sectional area, A. Identifying the radial frequency w with the heart frequency HF through the standard conversion factor, $w=2\pi$ HF, and incorporating $2\pi$ into the proportionality constant relating inertial reactance to total impedance, $k_3$, enables the expression of the aortic valvular impedance as:

$$Z=k_1 k_2 k_3 (HF/A) \qquad (2.4)$$

Equations (2.2) and (2.4) describe the same hemodynamic process and they may thus be equated to yield:

$$dPA=kQ\ HF \qquad (2.5)$$

where k is a constant combining $k_1$, $k_2$, and $k_3$ ($=k_1 k_2 k_3$). We shall identify the orifice coefficient k with the product of blood density and a proportionality constant with dimensions of length whose value is to be determined by clinical hemodynamic measurements. The left side of eq. (2.5) is the product of a pressure gradient and orifice area; it thus has dimensions of a force. This term represents the average force accelerating the blood across the aortic valve. The right side of the equation has dimensions of mass times acceleration. Thus eq. (2.5) is consistent with Newton's second law of motion and expresses the conservation of momentum across the aortic valve.

The variables forming eq. (2.5) are routinely measured during cardiac catheterization for the evaluation of aortic stenosis; hence its validity may readily be investigated once the orifice coefficient k is known.

An evaluation of the orifice coefficient k is now addressed. The data used in this evaluation were from 100 catheterizations of patients studied for aortic stenosis from six publications. A linear regression analysis was applied to derive the regression coefficient of the product HF Q on dP A. This analysis indicated that the coefficient k has an average value and standard estimated error given by $<k>=0.75\times 10^{-4}=0.20\times 10^{-4}$. Equation (2.5) may now be expressed for the computation of aortic valve area as:

$$A=0.75\times 10^{-4}\ HF(Q/dP) \qquad (2.6)$$

As a test of the validity of eq. (2.6) to predict orifice valve areas, a set of catheterization data independent of the data of the present study yielding HF, Q, dP, and A as computed by the Gorlin formula was used. These were the 33 studies comprising the catheterization procedures for the evaluation of patients with aortic stenosis presented in the published literature. Equation (2.6) was used to compute aortic valve areas for the 33 cases and was correlated with the results of an area computation by the Gorlin formula. The correlation of areas computed by eq. (2.6) with the results of the Gorlin formula (r=0.76, SE=0.32) suggest that eq. (2.6) may be considered to be an independent orifice equation enjoying a similar domain of validity as the Gorlin formula. Equations (2.1) and (2.6) independently describe the same hemodynamic process; thus they may be solved simultaneously so as to eliminate the independent variable of pressure gradient.

Substituting dP from eq. (2.6) into eq. (2.1) yields:

$$A=7Q\ HF^{-3} t^{-2} \qquad (2.7)$$

Calling the ratio Q/HF the stroke volume (SV) and the product HF t=T, we have the equation:

$$A=7SV/(HFt)^2=7SV/T^2 \qquad (2.8)$$

Equation (2.8) expresses aortic valve area in terms that are readily measurable by echocardiographic means or by cardiac catheterization techniques of a less invasive nature than are currently the practice for aortic valve function assessment.

As a test of this formulation, eq. (2.8) was used to compute the aortic valve area from a series of 37 patients evaluated for aortic stenosis at the Division of Pediatric Cardiology at the University of California at San Diego during the period 1975 to 1978. Of the 37 cases studied, 33 records included sufficient data to permit an evaluation of the new formulation. This patient group consisted of 26 boys and 7 girls with a mean age of 8.75 years. Aortic stenosis was the only significant lesion in the present series. Catheterization of the right and left heart was accomplished by standard techniques. Cardiac output was computed by the Fick principle, the thermodilution technique, or the dye dilution method. The mean aortic valve gradient was determined by planimetric integration of the difference between left ventricular and aortic systolic ejection pressure over at least five cardiac cycles. The systolic ejection period was determined from the simultaneous aortic pressure pulse and left ventricular pressure pulse. Using these hemodynamic data, the aortic valve area was computed from the standard Gorlin formula (2.1) and eq. (2.8).

In addition to the catheterization studies, 12 of these patients also had a pre- or postcatheterization M-mode echocardiographic study. The echographic parameters of left ventricular diastolic dimension, $D_d$, left ventricular systolic end dimension $D_s$, and the systolic ejection time $T_e$ in sec/min were measured. $D_d$ was taken as the perpendicular distance between the endocardial tracing of the left ventricular wall and the left septal tracing measured at end-diastole as indicated by the R wave of the simultaneously recorded EKG record. $D_s$ was measured as the perpendicular distance from the maximal anterior excursion of the endocardial tracing of the left ventricular posterior wall to the left septal tracing. The left ventricular systolic ejection time was determined echographically as the interval between the opening and closing of the aortic valve cusps. The heart frequency was measured by averaging the R—R interval of the associated EKG record over at least five cardiac cycles. Applying the Teichholz formula to the left ventricular dimensions yielded as estimate of the stroke volume. These data were then used to compute the predicted aortic valve area from eq. (2.8).

Of the 33 cases in the present study, there were five cases each of supravalvular and subvalvular stenosis. These cases were subject to further separate analysis for the relevant statistical parameters.

Sample Aortic Valve Area Calculation

Figure 5A:
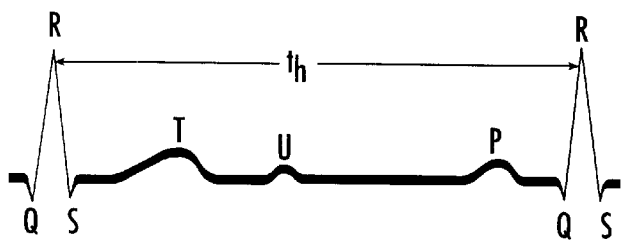
FIG. 5*a,b* are typical EKG and PCG records, respectively, of a patient with aortic stenosis showing relevant cardiac intervals.
Figure 5B:
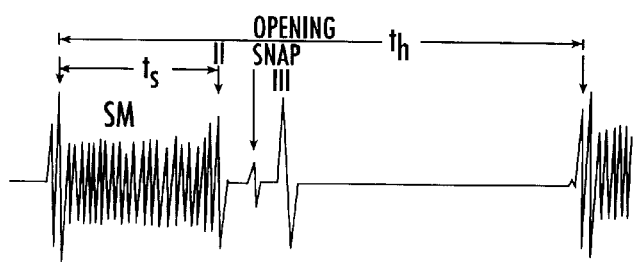

Referring to FIGS. 1 and 5a and b, and using Eq. (2.8), an exemplary calculation for the aortic valve area is provided, although this particular method is not intended to be limiting. The stroke volume SV is computed from the M-mode echocardiogram 12a as above for the mitral valve case. $t_s$, the systolic ejection period, is measured from the ES-II interval in the phonocardiogram 12c, and the heart rate is given by the reciprocal of the I—I interval of the phonocardiogram 12c or the EKG 12d R—R interval.

For a particular case, $D_{es}=18$, $D_{ed}=59$, SV=86, $t_s=0.32$, R=60. The aortic valve area A is then calculated to be 1.55; A>2.5 is considered normal.

Results

The principal result of this study is the development of a formulation for the quantitative assessment of aortic stenosis in a less invasive manner than is the conventional practice through application of the orifice equation $A=7\ SV/T^2$. Documentation of the predictive capacity of this and the independent auxiliary equation used in its derivation are presented in Tables 11–15.

TABLE 11

Comparison of aortic valve areas as computed by the Gorlin formula and Eq. (2.6) for an independent series of investigations.

| Case No. | HF | Q | T | dP | $A_G$ | $A_M$ |
|---|---|---|---|---|---|---|
| 1 | 72 | 7.5 | 21.2 | 20 | 1.75 | 2.75 |
| 2 | 70 | 4.2 | 16.1 | 30 | 1.10 | 0.75 |
| 3 | 90 | 7.8 | 4.3 | 47 | 1.05 | 1.50 |
| 4 | 95 | 6.5 | 1.0 | 45 | 1.05 | 1.05 |
| 5 | 61 | 6.4 | 7.7 | 68 | 1.00 | 0.55 |
| 6 | 90 | 4.3 | 7.1 | 35 | 0.95 | 0.85 |
| 7 | 82 | 6.2 | 19.7 | 54 | 0.95 | 0.70 |
| 8 | 72 | 6.8 | 8.0 | 81 | 0.95 | 0.45 |
| 9 | 80 | 6.5 | 13.7 | 54 | 0.90 | 0.95 |
| 10 | 98 | 6.4 | 23.5 | 45 | 0.90 | 1.05 |
| 11 | 72 | 6.3 | 21.7 | 51 | 0.90 | 0.90 |
| 12 | 82 | 5.8 | 18.8 | 61 | 0.90 | 0.60 |
| 13 | 97 | 7.2 | 26.2 | 40 | 0.90 | 1.75 |
| 14 | 85 | 3.5 | 17.0 | 34 | 0.80 | 0.65 |
| 20 | 110 | 4.5 | 19.8 | 40 | 0.80 | 0.90 |
| 21 | 68 | 4.7 | 17.4 | 53 | 0.75 | 0.45 |
| 22 | 84 | 4.8 | 22.2 | 41 | 0.75 | 0.55 |
| 23 | 72 | 4.8 | 20.4 | 66 | 0.65 | 0.50 |
| 24 | 102 | 4.2 | 22.4 | 47 | 0.65 | 0.75 |
| 25 | 107 | 5.1 | 26.5 | 45 | 0.65 | 1.20 |
| 26 | 77 | 5.4 | 25.0 | 60 | 0.60 | 0.65 |
| 27 | 73 | 5.1 | 21.2 | 76 | 0.60 | 0.50 |
| 28 | 62 | 3.5 | 19.0 | 57 | 0.55 | 0.40 |
| 29 | 79 | 4.9 | 23.4 | 88 | 0.55 | 0.45 |
| 30 | 90 | 5.2 | 24.3 | 88 | 0.50 | 0.50 |
| 31 | 89 | 3.5 | 20.3 | 64 | 0.50 | 0.50 |
| 32 | 73 | 3.8 | 22.0 | 63 | 0.50 | 0.45 |
| 33 | 80 | 3.0 | 26.8 | 88 | 0.35 | 0.25 |
| Mean | | | | | 0.81 | 0.81 |
| SE | | | | | | 0.32 |
| r | | | | | | 0.76 |

TABLE 11-continued

Comparison of aortic valve areas as computed by the Gorlin formula and Eq. (2.6) for an independent series of investigations.

| Case No. | HF | Q | T | dP | $A_G$ | $A_M$ |
|---|---|---|---|---|---|---|

HF = heart frequency, Q = cardiac output (l/min), T = systolic ejection time (sec/min), dP = average aortic valve gradient (mm Hg), $A_G$ = aortic valve area from the Gorlin formula (cm$^2$), $A_M$ = aortic valve area from equation (2.6) in cm$^2$, SE = standard error of $A_M$ relative to $A_G$ (1 mm Hg = 0.133 kPa).

TABLE 12

Comparison of aortic valve areas computed by the Gorlin formula with valve areas derived from the noninvasive eq. (2.8) from a series of 33 catheterization studies.

| Case | (n) | HF | Q | T | SV | dP | $A_G$ | $A_N$ |
|---|---|---|---|---|---|---|---|---|
| 1 | (1) | 90 | 8.4 | 22.2 | 93 | 30 | 1.55 | 1.35 |
| 2 | (1) | 80 | 9.7 | 22.2 | 122 | 54 | 1.35 | 1.80 |
| 3 | (1) | 115 | 7.0 | 30.6 | 61 | 25 | 1.05 | 0.45 |
| 4 | (1) | 60 | 3.6 | 19.8 | 60 | 17 | 1.00 | 1.05 |
| 5 | (2) | 90 | 6.9 | 27.6 | 99 | 43 | 0.85 | 0.90 |
| 6 | (3) | 100 | 6.6 | 26.4 | 66 | 44 | 0.80 | 0.65 |
| 7 | (1) | 106 | 6.2 | 26.4 | 58 | 50 | 0.75 | 0.60 |
| 8 | (1) | 100 | 5.4 | 26.4 | 54 | 42 | 0.70 | 0.55 |
| 9 | (1) | 133 | 5.2 | 25.2 | 39 | 42 | 0.70 | 0.45 |
| 10 | (1) | 90 | 5.8 | 36.0 | 64 | 26 | 0.70 | 0.35 |
| 11 | (1) | 85 | 4.9 | 27.6 | 58 | 33 | 0.70 | 0.55 |
| 12 | (1) | 85 | 4.7 | 24.6 | 55 | 42 | 0.65 | 0.65 |
| 13 | (1) | 80 | 6.0 | 40.8 | 75 | 30 | 0.65 | 0.30 |
| 14 | (1) | 110 | 2.5 | 34.2 | 23 | 20 | 0.55 | 0.15 |
| 15 | (2) | 120 | 4.4 | 40.0 | 37 | 27 | 0.50 | 0.15 |
| 16 | (1) | 80 | 4.7 | 33.6 | 59 | 39 | 0.50 | 0.40 |
| 17 | (1) | 112 | 5.3 | 33.0 | 47 | 48 | 0.50 | 0.30 |
| 18 | (1) | 75 | 4.1 | 27.6 | 55 | 50 | 0.45 | 0.50 |
| 19 | (1) | 125 | 2.5 | 26.4 | 20 | 20 | 0.45 | 0.20 |
| 20 | (1) | 90 | 3.1 | 30.0 | 35 | 25 | 0.45 | 0.30 |
| 21 | (1) | 78 | 3.5 | 24.6 | 32 | 48 | 0.45 | 0.40 |
| 22 | (1) | 90 | 4.1 | 30.0 | 46 | 17 | 0.40 | 0.35 |
| 23 | (1) | 70 | 3.6 | 30.6 | 51 | 45 | 0.40 | 0.40 |
| 24 | (2) | 110 | 2.8 | 30.0 | 25 | 27 | 0.40 | 0.20 |
| 25 | (3) | 88 | 5.9 | 31.8 | 67 | 67 | 0.35 | 0.45 |
| 26 | (3) | 95 | 2.5 | 27.0 | 26 | 37 | 0.35 | 0.25 |
| 27 | (1, 2) | 100 | 6.0 | 33.0 | 62 | 128 | 0.35 | 0.40 |
| 28 | (1) | 100 | 2.6 | 31.2 | 26 | 40 | 0.30 | 0.20 |
| 29 | (1) | 120 | 2.2 | 26.4 | 18 | 44 | 0.30 | 0.20 |
| 30 | (1) | 110 | 3.2 | 27.0 | 29 | 100 | 0.25 | 0.25 |
| 31 | (3) | 90 | 2.9 | 29.4 | 32 | 80 | 0.25 | 0.25 |
| 32 | (1) | 100 | 2.0 | 30.0 | 20 | 24 | 0.30 | 0.20 |
| 33 | (2) | 120 | 7.4 | 37.4 | 62 | 86 | 0.10 | 0.30 |
| MEAN | | | | | | | 0.57 | 0.47 |
| SE | | | | | | | | 0.22 |
| r | | | | | | | | 0.85 | n = 1 signifies valvular stenosis, n = 2, supravalvular stenosis, n = 3, subvalvular stenosis, HF = heart frequency, Q = cardiac output (l/min), T = systolic ejection period (sec/min), SV = stroke volume (cm$^3$), dP = mean valve pressure gradient (mm Hg), $A_G$ = Gorlin valve area, $A_N$ = valve area by eq. (2.8),SE = standard error (cm$^2$), r = correlation coefficient relating the areas.

TABLE 13

Comparison of aortic valve areas computed by the Gorlin formula from catheterization data an from eq. (2.8) from M-mode echographic data.

| Case | $HF_C$ | $HF_E$ | $Q_C$ | dP | $T_C$ | $T_E$ | $SV_C$ | $SV_E$ | $A_G$ | $A_{NE}$ |
|---|---|---|---|---|---|---|---|---|---|---|
| 1 | 90 | 60 | 8.3 | 30 | 22.2 | 19.2 | 38 | 86 | 1.55 | 1.65 |
| 2 | 80 | 75 | 9.7 | 54 | 22.2 | 21.7 | 121 | 81 | 1.35 | 1.20 |
| 5 | 70 | 75 | 6.9 | 70 | 27.6 | 21.0 | 99 | 79 | 0.85 | 1.25 |
| 8 | 100 | 90 | 5.4 | 42 | 26.6 | 29.4 | 54 | 65 | 0.70 | 0.55 |
| 16 | 80 | 55 | 4.7 | 72 | 33.6 | 26.9 | 59 | 54 | 0.50 | 0.50 |

TABLE 13-continued

Comparison of aortic valve areas computed by the Gorlin formula from catheterization data an from eq. (2.8) from M-mode echographic data.

| Case | $HF_C$ | $HF_E$ | $Q_C$ | dP | $T_C$ | $T_E$ | $SV_C$ | $SV_E$ | $A_G$ | $A_{NE}$ |
|------|--------|--------|-------|-----|-------|-------|--------|--------|-------|----------|
| 17   | 112    | 68     | 5.3   | 48  | 33.0  | 23.1  | 47     | 27     | 0.50  | 0.35     |
| 19   | 125    | 65     | 2.5   | 20  | 26.4  | 15.6  | 20     | 15     | 0.45  | 0.45     |
| 20   | 90     | 81     | 3.1   | 25  | 30.1  | 27.5  | 34     | 62     | 0.45  | 0.55     |
| 21   | 78     | 65     | 3.5   | 48  | 24.6  | 23.4  | 45     | 67     | 0.45  | 0.85     |
| 26   | 95     | 150    | 2.5   | 37  | 27.0  | 45.0  | 26     | 15     | 0.35  | 0.05     |
| 32   | 100    | 60     | 2.0   | 24  | 30.0  | 18.6  | 20     | 27     | 0.30  | 0.55     |
| 31   | 90     | 80     | 2.9   | 80  | 29.4  | 24.0  | 32     | 38     | 0.25  | 0.45     |
| MEAN |        |        |       |     |       |       |        |        | 0.64  | 0.69     |
| SE   |        |        |       |     |       |       |        |        |       | 0.21     |
| r    |        |        |       |     |       |       |        |        |       | 0.87     |

$HF_C$ = heart frequency measured during catheterization, $HF_E$ = heart rate during echo study, $Q_c$ = cardiac output at catheterization, dP = average aortic valve pressure gradient during catheterization, $T_C$ = systolic ejection period (sec/min) duringcatheterization, $T_E$ = systolic ejection period during echo study, $SV_C$ = stroke volume from cath study, $SV_E$ = stroke volume from echo study, $A_G$ = effective aortic valve area from the Gorlin formula, and $A_{NE}$ = aortic valve area from eq. (2.8) using M-mode echo data.

TABLE 14

Comparison of aortic valve areas as computed by the noninvasive equation and the Gorlin formula for cases of supravalvular aortic stenosis.

| Case | HF  | Q   | T    | SV | dP  | $A_G$ | $A_N$ |
|------|-----|-----|------|-----|-----|-------|-------|
| 6    | 60  | 3.6 | 19.8 | 60  | 24  | 1.00  | 1.05  |
| 15   | 120 | 4.4 | 40.0 | 37  | 27  | 0.50  | 0.15  |
| 24   | 110 | 2.8 | 30.0 | 25  | 27  | 0.40  | 0.20  |
| 27   | 100 | 6.2 | 33.0 | 62  | 128 | 0.35  | 0.40  |
| 33   | 120 | 7.4 | 37.0 | 62  | 86  | 0.10  | 0.30  |
| MEAN |     |     |      |     |     | 0.47  | 0.42  |
| SE   |     |     |      |     |     |       | 0.21  |
| r    |     |     |      |     |     |       | 0.80  |

Symbol designations as in Table 12.

TABLE 15

Comparison of aortic valve areas as computed by the noninvasive equation and the Gorlin formula for cases of subvalvular aortic stenosis.

| Case | HF  | Q   | T    | SV | dP  | $A_G$ | $A_N$ |
|------|-----|-----|------|-----|-----|-------|-------|
| 5    | 70  | 6.9 | 27.6 | 98  | 70  | 0.85  | 0.90  |
| 6    | 100 | 6.6 | 26.4 | 66  | 44  | 0.80  | 0.65  |
| 25   | 88  | 5.9 | 31.8 | 67  | 135 | 0.35  | 0.45  |
| 26   | 95  | 2.5 | 27.0 | 26  | 37  | 0.35  | 0.25  |
| 31   | 90  | 2.9 | 29.4 | 32  | 80  | 0.25  | 0.25  |
| MEAN |     |     |      |     |     | 0.52  | 0.50  |
| SE   |     |     |      |     |     |       | 0.09  |
| r    |     |     |      |     |     |       | 0.93  |

Symbol designations as in Table 12.

Table 11 compares the results of the auxiliary equation (2.6) and the Gorlin formula for a database independent of that of the present study. Here the hemodynamic data of 33 cases discussed in the literature are used to test the auxiliary equation. With these data, eq. (2.6) compares with the Gorlin formula at a level given by a correlation coefficient and standard error of r=0.76 and SE=0.32 cm$^2$.

Table 12 compares the results of area computations by the Gorlin formula and the noninvasive orifice equation (2.8) for the 33 cases of the present investigation, the pediatric cases from the University of California at San Diego. Here potentially noninvasive portions of the hemodynamic data were used in eq. (2.8) to compute areas for comparison with the Gorlin-formula-derived areas. These results are characterized by a correlation coefficient and standard error of r=0.85 and SE=0.22 cm$^2$.

Table 13 displays the application of eq. (2.8) to the computation of aortic valve area from M-mode echographic data and compares the results with the Gorlin formula valves. These areas correspond at a level of r=0.87, SE=0.21 cm$^2$.

Table 14 compares the results of area computation by eq. (2.8) in comparison with the Gorlin formula for the five cases of supravalvular aortic stenosis from the catheterization study. These areas correlate at a level given by r=0.80, SE=0.09 cm$^2$.

Table 15 compares the results of eq. (2.8) and the Gorlin formula for five cases of subvalvular stenosis. Here the relevant statistical parameters are r=0.93 and SE=0.09 cm$^2$.

Discussion

The level of correlation displayed between the noninvasive equation and conventional catheterization methods suggests that the formulation of the present invention may predict effective aortic valve areas at a clinically useful level of accuracy. A particularly interesting feature relates to the level of correlation achieved by M-mode echocardiography relative to the Gorlin formula at catheterization. The M-mode echographic stroke volumes correlate with the catheterization derived values at a considerably lower level than the associated aortic valve areas. There are at least two factors that could contribute to this relationship. First, the stroke volumes may have changed from the time of catheterization to that of the echographic studies, as some of the respective studies were separated by considerable intervals. Second, the stroke volume has considerably less relative influence on the computed area by eq. (2.8) than does the term in the denominator. The term T in eq. (2.8) is composed of the heart frequency HF and the systolic ejection period t in sec/beat. Since this is raised to the power 2, the affects of both HF and t dominate the ratio $SV/T^2$. Furthermore, both HF and t can be measured at an excellent level of accuracy by M-mode echography. Thus the most accurate measurements dominate in eq. (2.8).

In this study retrospective data were analyzed. Thus the investigators performing the catheterization and echographic measurements did not know of the existence of the theory being tested. Furthermore, neither the catheterization data nor the echographic data were reinterpreted by the present investigators, but rather reported values were assumed for the calculations. The formulation of the present invention did not yield any false negatives ($A_N$>0.75 cm$^2$>$A_G$) applied to the potentially noninvasive portions of the catheterization. However, it did predict valve areas significantly lower than the Gorlin formula in five cases (3, 13, 14, 15, 24) from the catheterization records and one echographic case (26). Additionally, one false negative relative to the Gorlin formula from the echographically derived areas was noted.

The noninvasive formulation appears to offer a significant degree of correlation with conventional methods. However, a more meaningful comparison would be with precise anatomical measurements of aortic valve cross-sectional area. The principal reason for this is that, while all the hemodynamic variables associated with eq. (2.8) can be measured at a highly reliable level by the Fick-principle methods of stroke volume in combination with echogaphic- or catheterization-derived values of left ventricular ejection period, the Gorlin formula requires an additional pressure measurement.

In the case of aortic stenosis, the pressure gradient is subject to considerable variation due to pressure fluctuations both proximal and distal to the aortic valve. Distal to the valve the pressure variations arise from turbulent flow in the ascending aorta as mediated through the mechanism of eddy formation. In a series of simulated studies of flow conditions in model aortic valves and ascending aortas, pressure variations have been observed and reported just distal to the aortic valve in the range of 10 to 30 mm Hg. Thus pressure probes in the vicinity immediately distal to the aortic valve may be expected to read pressure variations due to random turbulent eddy velocities of a significant level. This may suggest that pressure measurements at catheterization could be more accurately recorded at a point more distal to the aortic valve than is the conventional practice.

In addition to the random time-varying pressure fluctuations in the ascending aorta, it has been reported in the literature that significant spatial pressure variations exist within the left ventricle that could have an influence on the accuracy of the pressure gradient measurement. This investigation measured the left ventricular spatial pressure variation in a series of 20 dogs and observed an average pressure difference of 15.7 mm Hg between the apex and base during systole. This value corresponded to a 15% spatial variation in the pressure of the left ventricle during systole. To the extent that these findings are relevant to human conditions, they suggest that spatial pressure variations of approximately 20 mm Hg from the apex to the base in the left ventricle should be considered normal. The spatial variations also appear to be the result of turbulent velocity eddies.

These independent investigations suggest that spatial variations proximal to the aortic valve and random pressure fluctuations distal to it may contribute up to 40 mm Hg of uncertainty to the pressure gradient measurement. The spatial pressure variations within the left ventricle tend to vary along an axis extending from the apex to the base. Thus consistent probe placement would be expected to minimize this positional uncertainty. On the other hand, the random pressure fluctuations proximal to the aortic valve in the ascending aorta are nonsystematic in nature and can only be minimized by positioning the pressure probe more distal to the valve in a region where the initial turbulence has dissipated itself into more laminar flow.

If this concept is correct, it would be expected that there would be an observable difference in the behavior of subvalvular and supravalvular stenosis, with supravalvular stenosis producing greater turbulence immediately distal to the aortic valve and hence greater pressure uncertainties at the pressure probe site. If we compare the valve area computations from eq. (2.8) with the Gorlin formula for cases of subvalvular and supravalvular stenosis, a greater correspondence in the subvalvular case would be expected to be detected.

The data of these studies include five patients, each with supravalvular and subvalvular stenosis. The correlation between the Gorlin formula and the noninvasive equation reveals a significant difference in these two cases reveals a significant difference in these two cases, $(r_{sup}, r_{sub})=(0.80, 0.93)$, $(SE_{sup}, SE_{sub}=(0.2, 0.09)$. This effect may be further documented if the correlation coefficient for the cases of pure valvular stenosis are compared with those of sub- and supravalvular stenosis, respectively. If the reported observations as interpreted by the present theory are valid, the correlation for the purely valvular cases should occupy an intermediate position between the extremes. The correlation coefficient for the cases of pure valvular stenosis is $r=0.86$, $n=23$.

The areas in eq. (2.6) and the Gorlin formula depend upon the aortic valve gradient to the power $-1$ and $-\frac{1}{2}$, respectively. Thus it would be expected that the effects of pressure variations would likewise be reflected in comparisons between these two orifice equations. Again comparing the five patients with supra- and subvalvular stenosis, a correlation of $r=0.70$ is found between eq. (2.6) and the Gorlin formula in the subvalvular case and no significant difference in correlation between the two equations in the supravalvular cases. Again, this evidence supports the reported observations. It should be noted, however, that this comparison is subject to the influence of the difference in form of the dependence of heart rate in the Gorlin formula as compared to eq. (2.6). Errors in heart rate have an opposite effect on the area in eq. (2.6) compared to the Gorlin formula.

The spatial pressure variations within the left ventricle observed in previous work influence the relationship between the Gorlin formula and eq. (2.8) in yet another manner. At relatively low values of the aortic valve gradient, spatial pressure variations within the left ventricle or random temporal fluctuations in the ascending aorta would be expected to have the most adverse influence on a hydraulic formula utilizing pressure gradient. Thus at low aortic valve gradients a maximum divergence would be expected in the areas predicted by the Gorlin formula and other hydraulic orifice formulae with a different pressure dependence.

A potential source of uncertainty in the application of the noninvasive eq. (2.8) resides in aortic stenosis complicated by myocardial disease. The aortic valve gradient, dP, is the mean pressure difference accelerating a bolus of blood across the aortic valve during the early phase of the systolic ejection period. During this interval the blood is accelerated through the aortic valve to achieve its average steady-state level associated with the main portion of the ventricular ejection period. It is during the steady-flow state of the systolic ejection period that the Gorlin formula is valid. The fundamental assumption inherent in the present formulation is that the pressure difference during the early phase of the systolic ejection period is comparable to the average pressure gradient across the aortic valve during the total outflow period. Any ventricular condition that compromises its function other than stenosis may render this inherent assumption invalid. In addition, with decreased outflow impedance the rate of decrease of aortic pressure gradient may yield an average systolic ejection period gradient of less magnitude than during the early phase of systole. These considerations suggest that the present model may enjoy its greatest region of validity in conditions of moderate to severe stenosis, with less reliable predictions being associated with mild stenosis and normal valves.

While the current formulation eliminates the uncertainties associated with a pressure measurement, a potential source of computational error arises from the inverse quadratic dependence of the area on the left ventricular ejection period (sec/min). This term is the product of heart frequency and systolic ejection time (sec/beat). Measurement uncertainties in heart frequency or ejection time can therefore compound the uncertainties in the computed area by a factor of 2 for each of the associated measurements. Thus particular care should be directed to the accurate measurement of these variables, particularly in arrhythmic conditions. Resting-state conditions are expected to offer maximal hemodynamic stability for the formulation of the present invention.

In addition to the caution relative to the use of the noninvasive equation in aortic stenosis complicated by cardiomyopathies, conditions of hemodynamic disequilibrium, and arrhythmias, eq. (2.8) would not necessarily be valid for application in patients who have recently undergone aortic prosthetic replacement or valvotomy. In these situations the abrupt change in ventricular outflow impedance may not accurately reflect itself in a comparable change in left ventricular ejection period until a myocardial readjustment period has elapsed. Similar effects have been previously observed with regard to pressure, as estimated by the ratio of end-systolic wall thickness to end-systolic ventricular dimension as compared to left ventricular pressure at catheterization after valvular replacement of valvotomy. In this situation the left ventricle requires several months to redistribute myocardial mass so as to reflect a suddenly changed pressure state by the thickness-to-dimension ratio.

Current echocardiographic techniques offer the opportunity to measure the basic variables of the noninvasive orifice eq. (2.8) at a clinically useful level of accuracy. A series of forty patients have been studied previously using eight of the currently proposed M-mode echocardiographic stroke volume formulae, and it was concluded that the Teichholz formula can achieve correlations of up to 0.84 relative to the Fick principle and thermodilution methods in the absence of wall motion irregularities. Two-dimensional echocardiography would be expected to yield greater accuracy in stroke volume estimates. It has been previously demonstrated that this technique can compute stroke volume at a level of r=0.87. In this series of studies, 65% of the patients had one or more areas of wall motion asymmetry.

The extent to which areas computed by eq. (2.8) correspond with the Gorlin-formula-derived areas will partially depend upon the techniques used by the particular catheterization laboratory to determine the pressure gradient. The use of average peak values would be expected to produce somewhat lower valve areas than the use of average systolic pressure values. An elementary correction to the coefficient of eq. (2.8) may be defined from average values of heart frequency, systolic ejection period (sec/min), and pressure gradient from a series of cases at a particular catheterization laboratory from the ratio u=<HF><T>/(310<dP>). This ratio will have a value close to 1 for conventional laboratory techniques. Laboratories using modified values of the Gorlin constant or special pressure measurement techniques will be able to relate their computed areas to the present formulation by the modified equation:

$$A = 7uSV/T^2$$

where u is a factor determined by averaging a particular catheterization laboratory's data relative to the factor 7.

It should be noted that the average values of HF, T, and dP refer to series averages over many patient records for the particular catheterization laboratory and not single-patient average values at a particular catheterization study.

The expression that recommends itself for possible clinical application in resting-state conditions in the absence of associated cardiomyopathies is eq. (2.8).

Conclusion

It can be seen that the present invention provides a method of measuring aortic valve area noninvasively. The only parameters required are stroke volume, systolic ejection period, and heart rate. Stroke volume may be measured as in Section 3; systolic ejection period, by M-mode echocardiography or phonocardiography; and heart rate, by EKG or echo record.

3. Stroke Volume and Left Ventricular Volume Calculation

An elementary computational formula for estimating cardiac volume and stroke volume from either M-mode or bidimensional echographic data is developed from an analysis of retrospective catheterization, angiographic, and echographic data. The model of the present invention assumes the validity of the Teichholz correction factor to the volume of an ellipsoid of revolution as an approximation of left ventricular cardiac volume.

The Teichholtz equation summarizes the relationship between cardiac volume and the ventricular dimension based on 100 volume measurements. These data may be rearranged so as to derive an elementary exponential formula for cardiac volume. This expression was found by fitting a general exponential equation to the volume dimension data of Teichholz et al. The result of this analysis may be expressed as:

$$V = 0.01 D^{12/5} \qquad (3.1)$$

where V is cardiac volume in milliliters, 0.01 is a combination unit conversion and regression coefficient, and D is the standard ventricular dimension in millimeters. The stroke volume (SV) is readily determined from eq. (3.1) as:

$$SV = V_{ed} - V_{es} = 0.01(D_{ed}^{12/5} - D_{es}^{12/5}) \qquad (3.2)$$

where $V_{ed}$ and $V_{es}$ represent the end-diastolic and -systolic volumes, respectively, and $D_{ed}$ and $D_{es}$ represent the end-diastolic and systolic dimensions, respectively.

The validity of this formulation is readily tested by comparing stroke volume computed with eq. (3.2) and stroke volumes computed by standard invasive methods and the Teichholz formula from echographic records. Application of this model to retrospective echographic data reveals that the model enjoys an identical domain of validity as the Teichholz formula, deviating from this model by less than 1% over a range of cardiac volumes from 20 to 180 ml. Comparison of this cardiac volume formula with a series of 37 echographic and catheterization measurements of stroke volume yields a correlation of r=0.95 with a standard error of SE=14.3 ml in comparison with the Fick principle method for cardiac stroke volume (Table 16). The results suggest that the present expression offers the computational simplification of the Teichholtz formula, facilitating modifications for other configurations while retaining this expression's favorable correlation with invasive measurements of cardiac volume.

The test comprised analyzing 37 separate catheterization and echographic studies for cardiac volume and stroke volume using eqs. (3.1) and (3.2) in comparison with stroke volume as determined by the Fick principle at cardiac catheterization and the results of the Teichholz formula calculation for cardiac volume and stroke volume derived from echocardiographic data taken from the same patients. The catheterization and echocardiographic investigations have been published previously. Catheterization and echocardiographic studies were performed on a series of 54 patients. Twenty-four were excluded from the present investigation due to the documented existence of valvular regurgitation. The echographic study was completed during the interval over which time data for the Fick principle computation were obtained. The left ventricular dimension was defined as the distance between the endocardial echo of the posterior left ventricular wall and the endocardial echo of the left side of the interventricular septum. The patients were studied supine with the transducer positioned at the fourth or fifth intercostal space alone the left sternal border.

TABLE 16

Correlation between cardiac volume and stroke volume determined by cardiac catheterization and echocardiography using the Teichholz formula and the present formulation.

| CN | S | $D_d$ | $D_s$ | $V_{dT}$ | $V_{sT}$ | $V_{dN}$ | $V_{sN}$ | $SV_F$ | $SV_T$ | $SV_N$ | DX |
|---|---|---|---|---|---|---|---|---|---|---|---|
| 1 | R | 4.3 | 2.9 | 83.1 | 32.2 | 83.3 | 32.2 | 63.0 | 50.8 | 50.9 | CAD |
| 2 | R | 4.4 | 3.9 | 87.7 | 65.9 | 87.9 | 65.8 | 24.0 | 21.8 | 22.1 | CMP |
| 3 | R | 5.6 | 4.6 | 153.6 | 97.3 | 156.9 | 97.8 | 58.0 | 48.2 | 49.5 | AS |
| 5 | R | 3.9 | 2.7 | 65.9 | 27.0 | 65.8 | 27.2 | 46.0 | 38.9 | 38.6 | MS |
| 6 | R | 4.1 | 2.6 | 74.2 | 24.6 | 74.2 | 24.9 | 57.0 | 49.6 | 49.3 | HCVD |
| 7 | R | 5.0 | 3.8 | 118.2 | 69.9 | 119.5 | 61.8 | 75.0 | 56.3 | 57.7 | AS |
| 8 | R | 5.8 | 4.4 | 166.5 | 87.8 | 170.7 | 87.9 | 111.0 | 78.8 | 82.7 | AS |
| 9 | R | 4.0 | 3.0 | 70.0 | 35.0 | 69.9 | 35.1 | 39.0 | 35.0 | 34.9 | CP |
| 10 | R | 5.5 | 4.2 | 147.4 | 78.6 | 150.2 | 78.7 | 83.0 | 68.8 | 71.6 | AS |
| 11 | R | 4.8 | 3.8 | 107.5 | 61.8 | 108.4 | 61.8 | 57.0 | 45.5 | 46.5 | AS |
| 12 | R | 5.8 | 5.3 | 166.5 | 135.3 | 170.7 | 137.5 | 64.0 | 31.2 | 33.2 | VA |
| 13 | R | 4.0 | 2.8 | 70.0 | 24.5 | 69.9 | 29.7 | 44.0 | 40.4 | 40.2 | MS |
| 14 | R | 4.7 | 3.2 | 102.3 | 40.9 | 103.0 | 40.9 | 65.0 | 61.4 | 62.1 | AS |
| 15 | R | 5.4 | 5.0 | 141.3 | 118.2 | 143.8 | 119.5 | 37.0 | 23.1 | 24.2 | CMP |
| 16 | R | 3.9 | 2.2 | 65.9 | 16.2 | 65.8 | 16.6 | 59.0 | 49.7 | 49.1 | MS |
| 17 | R | 4.6 | 2.4 | 97.3 | 20.1 | 97.8 | 20.5 | 84.5 | 77.1 | 77.3 | CAD |
| 18 | R | 4.7 | 3.6 | 102.3 | 54.4 | 103.0 | 54.3 | 53.3 | 47.9 | 48.7 | CMP |
| 19 | R | 3.6 | 2.0 | 54.4 | 12.7 | 54.3 | 13.2 | 48.0 | 41.7 | 41.1 | MS |
| 20 | R | 4.3 | 3.4 | 83.1 | 47.4 | 83.2 | 47.3 | 44.0 | 35.6 | 35.6 | COA |
| 21 | R | 5.5 | 4.9 | 147.4 | 112.8 | 150.2 | 113.8 | 43.0 | 34.6 | 36.4 | CMP |
| 22 | R | 4.0 | 2.6 | 70.0 | 24.6 | 69.9 | 24.9 | 63.0 | 44.4 | 45.1 | FM |
| 23 | R | 4.7 | 4.4 | 102.3 | 87.8 | 103.0 | 87.8 | 24.0 | 14.7 | 15.1 | CP |
| 24 | R | 5.4 | 4.0 | 141.3 | 70.0 | 143.8 | 69.9 | 99.0 | 71.3 | 73.8 | CAVP |
| 25 | E | 5.6 | 3.3 | 153.6 | 44.1 | 156.9 | 44.1 | 135.0 | 109.5 | 112.8 | CAVP |
| 26 | R | 4.7 | 3.3 | 102.4 | 44.1 | 103.1 | 44.1 | 71.2 | 58.2 | 58.9 | MS |
| 27 | E | 4.5 | 2.8 | 92.4 | 29.1 | 92.8 | 29.7 | 68.0 | 62.9 | 63.1 | MS |
| 28 | R | 5.9 | 5.3 | 173.2 | 135.3 | 177.8 | 137.5 | 60.0 | 37.8 | 40.4 | AS |
| 29 | E | 6.0 | 5.3 | 180.0 | 135.3 | 185.1 | 137.5 | 62.0 | 44.6 | 47.7 | AS |
| 30 | R | 4.7 | 3.2 | 102.3 | 40.8 | 102.5 | 40.9 | 76.0 | 61.4 | 62.1 | MS |
| 31 | E | 4.6 | 3.9 | 97.3 | 65.9 | 65.8 | 97.8 | 38.0 | 31.4 | 32.0 | MS |
| 32 | R | 6.2 | 5.8 | 194.0 | 166.5 | 200.3 | 170.7 | 43.0 | 27.4 | 29.6 | AS |
| 33 | E | 6.2 | 5.8 | 186.9 | 166.5 | 192.6 | 170.7 | 38.0 | 20.3 | 22.0 | AS |
| 34 | R | 4.5 | 3.5 | 92.4 | 50.8 | 92.8 | 50.8 | 49.0 | 41.6 | 42.0 | MS |
| 35 | E | 4.2 | 3.3 | 44.4 | 34.4 | 44.5 | 34.5 | 40.0 | 34.4 | 34.5 | MS |
| 36 | R | 4.5 | 3.4 | 92.4 | 47.4 | 92.8 | 47.4 | 66.0 | 45.0 | 45.4 | FM |
| 37 | E | 4.8 | 4.0 | 107.5 | 70.0 | 108.4 | 69.9 | 62.0 | 37.5 | 38.4 | FM |
| MEAN | | | | | | | | 60.3 | 46.9 | 47.9 | |
| $SE(V_F; V_T, V_N)$ | | | | | | | | | 15.6 | 14.3 | |
| $r(V_F; V_T, V_N)$ | | | | | | | | | 0.94 | 0.95 | |
| $SE(V_T, V_N)$ | | | | | | | | | | 1.55 | |
| $r(V_T, V_N)$ | | | | | | | | | | 0.99 | |

CN = case number; S = state (R = rest, E = exercise); $D_d$ = left ventricular end diastolic dimension in cm; $D_s$ = left ventricular left systolic end dimension in cm; $V_{dT}$ = left ventricular end diastolic volume by the Teichholz formula in ml; $V_{sT}$ = left ventricularend systolic volume by the Teichholz formula in ml; $V_{dN}$ = left ventricular end diastolic volume from eq. (3.1) in ml; $V_{sN}$ = left ventricular end systolic volume from eq. (3.1) in ml; $SV_F$ = stroke volume measured by the Fick principle method; $SV_T$ = stroke volume computed from the Teichholz formula; $SV_N$ = stroke volumecomputed from eq. (3.1); DX = laboratory diagnosis (AS = aortic stenosis; CAD = coronary artery disease; CMP = cardiomyopathy; COA = coarctation of the aorta; CAVB = congenital atrioventricular block; CP = constrictive pericarditis; FM = functional murmur; HCVD = hypertensive cardiovascular disease; MR = mitral regurgitation; MS = mitral stenosis);$SE(V_F; V_T, V_N)$ = standard error of $V_T$ and $V_N$ relative to $V_F$; $r(V_F; V_T, V_N)$ = correlation coefficient of $V_T$ and $V_N$ relative to $V_F$; $S_E(V_T, V_N)$ relative standard error between $V_T$ and $V_N$ and $r(V_T, V_N)$ = correlation coefficient of $V_N$ relative to $V_T$.

The correlation of the new formula with the Teichholz formula is characterized by a linear correlation coefficient of 0.99 and a standard error of SE=1.55 ml. Comparing eq. (3.2) with the invasively derived stroke volume yields a correlation coefficient and standard error of r=0.95 and SE=14.3 ml, respectively.

The proposed cardiac volume formula, eq. (3.1), appears to offer a meaningful degree of correspondence with standard invasive methods for stroke volume and with the Teichholz formula with respect to cardiac volume. The fact that eq. (3.1) slightly overestimates cardiac volume relative to the Teichholz formula could offer some computational advantage in that it has been indicated that the Teichholz formula tends to underestimate cardiac volume in comparison with conventional invasive methods. Extrapolating the original data of Teichholz et al. reveals a SE relative to the angiographically determined stroke volume of approximately 14 ml.

The principal advantage of the present invention resides not in its slight correlational advantage with respect to the Teichholz formula, but rather in both its computational and manipulative simplicity. For example, the first derivatives of cardiac volume with respect to time for the Teichholz and present expressions may be expressed, respectively, as:

$$dV/dt = 7D^2(2.4+D)^{-2}[3(2.4+D)-1]dD/dt \quad (3.3)$$

$$dV/dt = 0.024D^{7/5}dD/dt \quad (3.4)$$

Higher-order derivatives become progressively more complex with the Teichholz formula but retain their elementary exponential form with eq. (3.1).

At least two other studies have indicated that the short-axis cardiac dimensions of the fetal right and left hearts are approximately equal. This result suggests that the fetal heart volume may be expressed by an elementary modification of the expansion coefficient (0.01) or the exponential term (12/5) of eq. (3.1) so as to yield an elementary expression for various fetal configurations.

As other echocardiographic techniques for viewing the heart become available, the elementary form of eq. (3.1) can be expected to allow adjustments permitting modifications so as to take advantage of other viewing aspects of the cardiac chambers. For example, a sub-xiphoid M-mode echographic approach has been developed for viewing the left ventricle. This technique can yield a short-axis ventricular dimension measurement in a direction approximately perpendicular to the conventional parasternal approach. Two left ventricular dimension measurements can thus be combined by applying eq. (3.1) in terms of the arithmetic mean to yield a volume representing the average volume corresponding to the parasternal and subxiphoid measurements according to the equation $V_{12}=0.005(D_1^{12/5}+D_2^{12/5})$, where $D_1$ is the ventricular dimension from the parasternal approach and $D_2$ is the ventricular dimension measured from the subxiphoid aspect. This composition of two different M-mode dimensions, in effect, takes into account the oblateness factor of the left ventricle in much the same manner that a bidimensional echocardiogram allows the oblateness of the ventricle to be visualized and corrected for.

It is thus seen that this invention provides an echographic method for calculating stroke volume that offers a high degree of correlation with both catheterization-derived stroke volume measurements and the Teichholz formula, while, at the same time, providing a more elementary mathematical structure and computational facility.

Sample Ventricular and Stroke Volume Calculation

Figure 4:
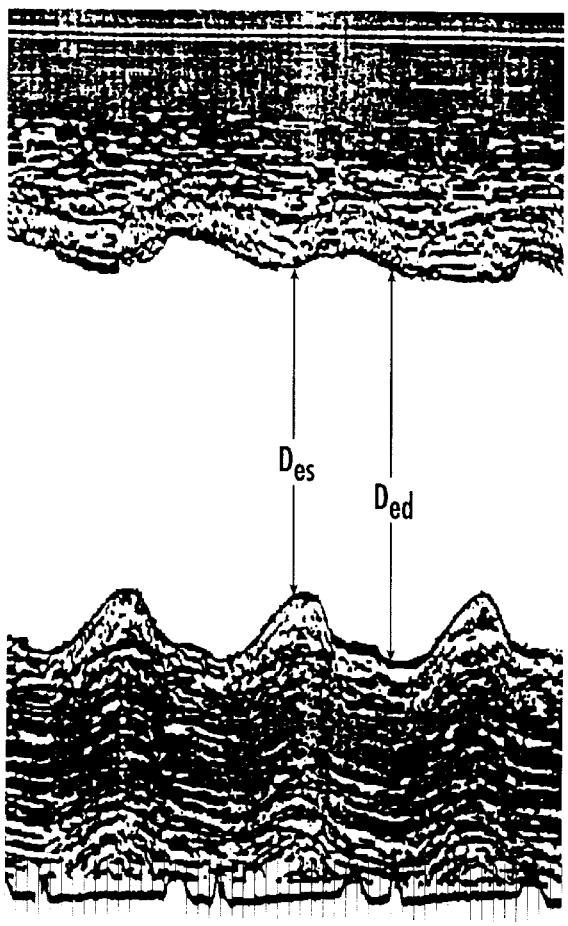
FIG. 4 is an M-mode echocardiogram showing cardiac dimensions needed for the mitral stenosis calculation, mitral and aortic pressure gradient calculations, and cardiac volume and flow calculations.

Take a case in which the end diastolic dimension $D_{ed}=43$ and the end systolic dimension $D_{es}=29$, which can be read off an M-mode echocardiogram 12a (FIG. 4).

With the use of eqs. (3.1) and (3.2), ventricular volume and stroke volume are calculated to be, respectively, 83 and 51 ml.

4. Noninvasive Assessment of Mitral Valve Pressure Gradient

The noninvasive formulation of the mitral valve area calculation in Section 1 has led to the simultaneous solution of two fundamental fluid flow equations that lead to an expression of mitral valve pressure gradient in terms of two fundamental time intervals in the cardiac cycle, the diastolic filling period and the length of the cardiac cycle. The validly of this theory has been tested by application of catheterization data.

This section describes the theoretical and experimental basis required to develop a method and instrumentation capable of measuring certain diagnostically useful heart chamber and lung vessel pressures by extracting the appropriate signals from a standard electrocardiogram. The pressures to be measured are intimately related to the valve area, valvular flow rate, and valve flow intervals through the laws of fluid physics.

The relationship between valvular flow, pressure gradient across the valve, valve area, and flow interval as applied to the mitral valve was first developed by Gorlin and Gorlin. This formula, an expression of the conservation of energy during the flow interval, determines the mitral valve area in terms of variables measurable at cardiac catheterization and has become the generally accepted technique for the assessment of stenotic mitral valve disease. Measurement of the mitral valve area using this method requires a direct pressure measurement within the heart chambers via catheterization.

In 1977 a series of investigations were initiated and later published to determine the possibility of measuring the mitral valve area by methods of a less invasive nature than conventional cardiac catheterization. These studies led to the derivation of an independent valve orifice equation utilizing the concept of the conservation of momentum across the valve orifice to derive the mitral valve area. By simultaneously solving the two independent orifice formulas describing conservation of energy, momentum, and fluid mass, it was demonstrated above that an additional valve orifice equation could be found that was capable of determining orifice area to a degree of accuracy comparable with conventional methods. Specifically this formula has been shown to correlate with the classical Gorlin formula at a level of r=0.95. The equation of the present invention specifies valve area in terms of variables measurable by, for example, an echocardiograph in a noninvasive manner.

Further investigations revealed that a combination of the orifice equation of the present invention with the classical Gorlin equation yielded an additional equation expressing the mitral valve pressure differential in terms of variables measurable with a standard electrocardiogram, specifically the heart rate and the T-R interval.

In mitral stenosis, the Gorlin equation has found extensive practical application in the determination of the mitral valve area. In this formulation the mitral valve area is expressed as a function of the hemodynamic variables of average mitral valve pressure gradient (dP), cardiac output (Q), heart rate (R), and diastolic filling period (T) in seconds according to the equation $$A=Q/(31RTdP^{1/2}) \tag{4.1}$$

In the original formulation, the average mitral valve pressure gradient, dP, was taken to be the capillary wedge pressure (P) minus the average left ventricular filling pressure ($P_o$). This average filling pressure is approximately 5 mm Hg in the absence of left ventricular dysfunction.

A fluid mechanical theory is now developed that offers the capacity of computing capillary wedge pressure, left atrial pressure, and the mitral valve pressure gradient from variables measurable by the standard phonocardiogram or electrocardiogram. A fundamental assumption of this model is that left atrial pressure is equivalent to capillary wedge pressure and this, in turn, equals the mitral valve pressure gradient plus the average ventricular filling pressure. This is indicated by the expression $P=dP+P_o$. Solving the Gorlin equation for average pressure gradient yields:

$$dP=Q^2/(31RAT)^2 \tag{4.2}$$

To develop a noninvasive determination of dP, a supplementary equation must be found relating the variables of interest and its validity must be demonstrated within satisfactory limits. This equation then must be solved simultaneously with eq. (4.2) so as to eliminate explicit dependence on all invasively measured variables, namely, Q and A, thereby expressing dP in terms of the remaining noninvasively measurable terms, R and T.

It will be demonstrated that a flow equation known to cardiologists as the mitral valve impedance equation possesses the desired properties. This equation is:

$$dP = k_1 ZQ \quad (4.3)$$

where dP is the pressure difference across the mitral valve responsible for accelerating blood into the left ventricle. This pressure gradient is essentially the same pressure used in the Gorlin equation. $k_1$ is a constant of proportionality and Q is the cardiac output. The term Z is often referred to by cardiologists as valvular resistance, incorrectly implying a steady flow condition. Since the flow mechanics of the mitral are described by a time-varying system, eq. (4.3) must be frequency dependent. In the general circuit theory of unsteady fluid flow, the magnitude of the impedance of the elements in the flow circuit may be expressed as:

$$Z = [Ri^2 + (Iw - 1/wC)^2]^{1/2} \quad (4.4)$$

where Ri is the contribution to flow impedance accounted for by resistive dissipation, Iw is the component describing the inertial reactance of the circuit, and 1/wC represents the contribution to reactance related to the distensibility of the structure containing the flow. For a relatively nondistensible structure, such as the mitral valve annulus in stenosis, C is large. The term I represents the reactance per unit frequency of the flow element associated with the mass of the fluid traversing the valve. The magnitude of 1 is directly proportional to the mass of the material the valve orifice is capable of transmitting per unit time. If it is assumed that the mitral valve is capable of transmitting blood with viscous or frictional losses small in comparison with the kinetic energy of the blood transmitted, the magnitude of the term Iw relative to Ri is large. Further, if it is assumed that the mitral valve walls are sufficiently rigid to prevent the distention of the mitral valve throughout the diastolic filling period, that is, if a constant mitral valve are from one cardiac cycle to the next is assumed, it may be assumed that the structural rigidity is great relative to the flow pressures and that 1/wC is small relative to Iw.

It now remains to determine precisely what valvular characteristics specify the valvular inertial reactance. The considerations thus far have suggested that the major contribution to valvular impedance is represented by Iw, and since the mass of the fluid transmitted through the valve per unit pressure difference is directly proportional to the valve area, Iw must be inversely proportional to valve area. This follows from the fact that impedance and conductance are reciprocal quantities by definition. Finally, if we identify w with the heart frequency R, we may express the valvular impedance as:

$$Z = k_2 R/A \quad (4.5)$$

where $k_2$ is a constant of proportionality and R and A have the same significance as in eq. (4.2). Equating the concepts of impedance expressed by eqs. (4.3) and (4.4) leads to:

$$dPA = kQR \quad (4.6)$$

where k is a constant combining $d_1$ and $k_2$ (=$k_1/k_2$). This expression expresses the conservation of momentum across the mitral valve. Since eq. (4.5) relates variables normally measured during cardiac catheterization, its validity is easily verified. As a test, eq. (4.5) was solved for the mitral valve area A for the 40 resting- and exercise-state cases described by Gorlin and Gorlin. The areas computed by eq. (4.5) correlate with the areas computed by the Gorlin equation at a level of r=0.90. Considering only the greater hemodynamic equilibrium associated with resting-state conditions, the data of Gorlin and Gorlin yield a correlation of r=0.95. Analysis of the 9 resting- and exercise-state cases for the same patient described by Gorlin and Gorlin indicates that the areas for the same patient measured twice are invariant to within 13%. Since valve orifice area is expected to be identical in the same patient for two different hemodynamic states, it seems likely that the average 13% variation is accounted for by measurement uncertainties. The level of correlation of the areas computed by eqs. (4.2) and (4.5) are describing the same hemodynamic process they may be solved simultaneously for the average mitral valve pressure differential dP. This process eliminates both Q and A, yielding dP in terms of easily measured quantities, R and T. Substituting area from eq. (4.5) into eq. (4.2) results in an expression for dP:

$$dP = 2.25 \times 10^{-6} R^4 T^2 \quad (4.7)$$

where pressure is measured in mm Hg. Since the original Gorlin and Gorlin data and the Stanford data are evaluated according to the method initially introduced by Gorlin and Gorlin, it will be assumed, following these authors, that the average mitral valve pressure gradient may be expressed as the capillary wedge pressure (left atrial pressure) minus the average left ventricular end diastolic pressure. This leads to an expression for capillary wedge pressure (P):

$$P = 2.25 \times 10^{-6} R^4 T^2 + 5 \quad (4.8)$$

This equation clearly indicates the sensitivity of pressure to errors in heart rate, as this variable appears to the fourth power. To accurately specify this variable, relatively long-term averages in a state of equilibrium should be used. In the analysis of retrospective data one cannot directly judge the accuracy of the reported heart rate measurement. It is possible, however, to gain some insight as to the likelihood of accurate values of the heart frequency with the aid of eq. (4.6). Since this orifice equation is an independent formula for the mitral valve area that correlates with the Gorlin equation at a level compatible with the accuracy of the original experimental data, and further since heart frequency appears in the numerator of eq. (4.5) and in the denominator of the Gorlin equation, comparison of the areas computed by the two equations would be expected to be quite sensitive to errors in the frequency measurement. This expression may thus be used to establish a criterion for estimating the expected accuracy of the heart rate data in the retrospectively determined areas.

The criterion adopted in selecting the data for the pressure computation was that the areas computed by eqs. (4.6) and (4.2) agree within 13% for the same hemodynamic state in accord with the area-invariance limits of the original Gorlin and Gorlin data. Further, since resting states may be considered to provide conditions most closely approximating hemodynamic equilibrium and stable heart rates, only resting-state cases were evaluated. Applying these criteria to the cases available from the Stanford University Hospital records and the original Gorlin and Gorlin cases from the Harvard University Hospital yielded 14 resting-state Harvard cases and 16 resting-state Stanford cases. For each of the 30 cases selected by these criteria, eq. (4.8) was used to compute the predicted capillary wedge pressure (see Table 17). The computed capillary wedge pressures were then correlated with the measured values. The computed and measured pressures correspond at a level of r=0.90 with a standard deviation of SEE=2.40.

TABLE 17

Comparison of catheterization-measured left atrial pressure, $P_c$, with left atrial pressure as computed by eq. (4.8), $P_e$, from case records of the Harvard University Hospital and the Stanford University Hospital.

| CASE | Lab | HF | T | $P_c$ | $P_e$ |
|---|---|---|---|---|---|
| R.C. | H | 108 | 33.5 | 39 | 36 |
| D.V. | H | 100 | 40.0 | 35 | 42 |
| Ba. | H | 105 | 34.6 | 32 | 36 |
| Gr. | H | 100 | 40.0 | 32 | 32 |
| M.G. | H | 82 | 29.0 | 30 | 19 |
| C.M. | H | 94 | 31.9 | 29 | 27 |
| E.S | H | 89 | 36.9 | 28 | 30 |
| N.L. | H | 105 | 37.8 | 28 | 28 |
| L.C. | H | 106 | 26.5 | 27 | 24 |
| E.S. | H | 80 | 40.0 | 26 | 29 |
| J.M. | H | 107 | 24.6 | 25 | 24 |
| L.T. | H | 70 | 36.4 | 24 | 20 |
| A.R. | S | 109 | 26.2 | 24 | 27 |
| W.F. | H | 80 | 40.0 | 23 | 29 |
| M.T. | S | 66 | 31.7 | 22 | 21 |
| M.M. | H | 56 | 43.1 | 22 | 19 |
| M.T. | H | 79 | 34.7 | 21 | 23 |
| J.F. | H | 72 | 33.8 | 21 | 19 |
| L.B. | H | 90 | 27.9 | 20 | 20 |
| J.F. | S | 83 | 29.9 | 19 | 20 |
| S.L. | S | 84 | 27.9 | 19 | 23 |
| A.B. | S | 70 | 32.9 | 18 | 18 |
| R.B. | S | 61 | 34.8 | 18 | 16 |
| A.D. | S | 82 | 24.6 | 18 | 15 |
| A.M. | S | 77 | 30.5 | 17 | 18 |
| M.S. | S | 65 | 32.5 | 16 | 16 |
| E.L. | S | 56 | 37.0 | 16 | 15 |
| F.K. | S | 95 | 26.6 | 14 | 20 |
| P.D. | S | 100 | 22.0 | 14 | 16 |
| S.V. | S | 37 | 10.7 | 8 | 10 |
| MEAN | | 82.5 | 33.3 | 23.0 | 23.1 |
| SEE | | | | | 2.4 |
| r | | | | | 0.89 |

HF = heart rate and T = diastolic filling period in sec/min.

Since the mitral valve pressure differential is seen to depend only on heart rate and the diastolic filling period, pressure differentials for several different patients as computed by eq. (4.8) will correspond on the average to the average measured pressure of such a group. The various combinations of (R, T, dP) for differing possible hemodynamic states corresponding to different patients may be regarded as a set of consistent hemodynamic states for a single hypothetical patient. This concept allows another test of the formulation. Since random errors in the measured heart rate and diastolic filling period may be expected to cancel out on the average, computation of the average pressure differential for several hemodynamic states should average the random measurement errors and yield an accurate average pressure gradient value. This concept was applied to the data studied and led to average pressure gradient values of 17.0 and 16.9 mm Hg for the computed and measured values, respectively. In this computation the average computed pressure gradient was found by the equation:

$$dP = 2.25 \times 10^{-6} R^4 T^2 \tag{4.9}$$

where R and T are the average heart rate and diastolic filling period of the 30 patients studied and $T = t_d R$. The average measured pressure differential was computed according to the equation:

$$dP = dP_n / N, \quad N = 30 \tag{4.10}$$

This result suggests that many-cycle averaging will allow a clinically useful level of accuracy in the pressure measurement.

Another test of the theory is possible by using an elementary transformation equation from differential calculus. Calling D (=RT) the diastolic filling period in seconds per minute allows eq. (4.8) to be expressed as:

$$dP = 2.25 \times 10^{-6} R^2 D^2 \tag{4.11}$$

Forming the total differential of dP yields:

$$d(dP) = 4.5 \times 10^{-6} (R^2 dD + D^2 dR) \tag{4.12}$$

This expression allows computation of the change in pressure through a knowledge of the change in R and D, according to the expression:

$$dP_1 + d(dP) = dP_2 \tag{4.13}$$

where the subscripts 1 and 2 refer to pressure gradients computed at two different times. For example, pressures measured at cardiac catheterization may be compared with pressure values computed by electrographic means after or before catheterization through use of the transformation equation (4.12).

Such a test was conducted with prospective data at the Division of Cardiology of the University of Vienna. In this study five patients were evaluated for mitral stenosis by conventional cardiac catheterization, by echocardiography, and by the standard electrocardiogram. First, eq. (4.9) was used to compute the left atrial pressure from the electrographic data taken simultaneously with direct pressure measurements in the left atrium. These results are presented in Table 18. A correlation of r=0.89 is associated between the measured and computed pressures. Next, the same group of patients were evaluated by simultaneous echocardiogram and a electrocardiogram study. This investigation was separated in time from the catheterization study by an interval of approximately one hour. The patients were thus in a different hemodynamic state and would be expected to have different atrial pressures than recorded at the catheterization study. Left atrial pressures were again computed with eq. (4.9) based on the noninvasive electrographic data and compared with left atrial pressure measured at catheterization. It would be expected that these values would be different from conditions at catheterization. The data summary is shown in Table 19. A correlation coefficient of r=0.66 characterizes this relationship. Finally, left atrial pressures were computed from the electrographic data using the two-state transformation equation:

$$P_2 = dP_1 + d(dP) + 5 \tag{4.14}$$

and compared with the catheterization derived pressures. The results are shown in Table 20. A correlation coefficient of r=0.91 is associated with this relationship.

Two time intervals within the EKG complex are required for estimation of the valve gradient by the proposed concept: the R—R interval and the T-R interval. The T(RR) and T(TR) intervals are of fundamental importance for the mitral valve gradient according to the proposed formulation. Determination of the T(RR) interval is relatively easy since the R-wave is usually the most prominent wave of the EKG. Detection of the T-wave is more difficult because of its smaller amplitude, sometimes negative amplitude, and slow rise and fall times. It should be noted, however, what while the T-wave is not always observable in any one lead of the standard EKG, it is generally present in one of the leads, even if inverted. Since the proposed concept depends only on time interval measurements and not electrode position for information, any lead yielding a recognizable T-wave may be selected for analysis. Furthermore, in a T-wave not readily discernible or of low amplitude in the standard positions, the electrodes may be repositioned on the patient so as to elicit the maximal T-wave response. Thus it would be expected that the conventional difficulties associated with computerized detection of the "R-T" interval can be minimized.

TABLE 18

Comparison of catheterization measured pressures, $P_c$, and pressures derived from electrographic data taken at catheterization, $P_e$ from the University of Vienna Hospital.

| CASE | R | T | $P_c$ | $P_e$ |
|------|----|----|----|----|
| P.I. | 80 | 37 | 31 | 26 |
| K.A. | 68 | 32 | 17 | 16 |
| S.E. | 65 | 35 | 21 | 18 |
| J.M. | 90 | 32 | 35 | 25 |
| M.J. | 85 | 29 | 16 | 19 |
| MEAN |    |    | 24 | 26 |
| SEE  |    |    |    | 3.44 |
| r    |    |    |    | 0.89 |

Symbols as in Table 4.1.

TABLE 19

Comparison of catheterization-measured left atrial pressures, $P_c$, with pressures derived from noninvasive electrographic data, $P_e$, more than one hour after catheterization without the use of the time transformation equation (4.14).

| CASE | HF | T | $P_c$ | $P_e$ |
|------|----|----|----|----|
| P.I. | 78 | 39 | 31 | 27 |
| K.A. | 65 | 34 | 17 | 18 |
| S.E. | 44 | 40 | 21 | 12 |
| J.M. | 75 | 36 | 35 | 23 |
| M.J. | 77 | 32 | 16 | 19 |
| Mean |    |    | 24 | 19 |
| SEE  |    |    |    | 4.5 |
| r    |    |    |    | 0.66 |

Symbols as in Table 4.1.

TABLE 20

Comparison of catheterization measured left atrial pressure, $P_c$, with pressures derived from noninvasive electrographic data, $P_e$, at a different time after applying the two state time transformation equation (4.14).

| CASE | HF | T | $P_c$ | $P_e$ |
|------|----|----|----|----|
| P.I. | 78 | 39 | 31 | 29 |
| K.A. | 65 | 34 | 17 | 20 |
| S.E. | 44 | 40 | 21 | 21 |
| J.M. | 75 | 36 | 35 | 35 |
| M.J. | 77 | 32 | 16 | 24 |
| Mean |    |    | 24 | 26 |
| SEE  |    |    |    | 3.3 |
| r    |    |    |    | 0.91 |

Symbols as in Table 4.1.

Sample Mitral Valve Pressure Gradient Calculation

Figure 6:
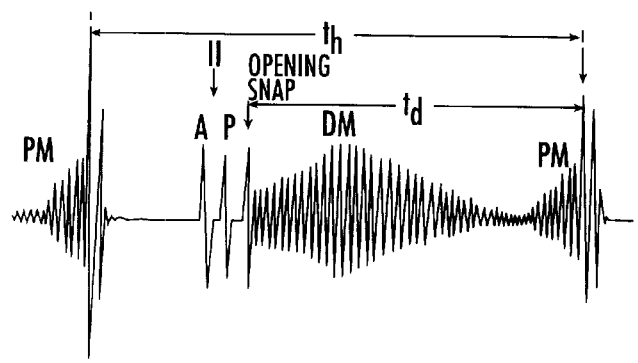
FIG. 6 is a PCG record showing intervals used in the mitral valve pressure gradient calculation.
Figure 8:
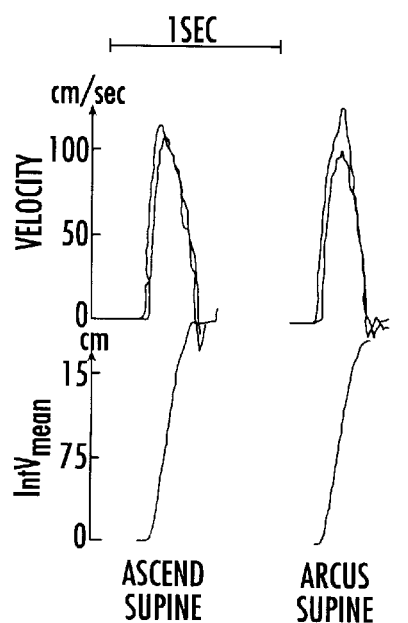
FIG. 8 is a Doppler ultrasound record showing a velocity tracing appropriate to the mitral and aortic insufficiency calculations.

As an example of calculating a mitral valve pressure gradient noninvasively via the method described above, insert into eq. (4.9) data obtained from a phonocardiogram 12c (FIG. 6). The heart rate R may be obtained by the inverse of $t_h$, which is the I—I interval. $t_d$ is given by the OP-I interval of the PCG 12c.

In a particular case, for R=78, $t_d$=0.51, $dP_p$ is calculated as 29, while the value found by cardiac catheterization is 31. A normal value would be <10.

This example is not intended to be limiting, as other noninvasively obtained data such as EKG records can also be used.

A Device for Measuring Mitral Valve Pressure Gradient

An automated device for carrying out the preceding calculation comprises a processor 20 that accepts analog voltage signals from the standard electrocardiogram 12d (EKG), performs specific mathematical operations on these signals, and reads out a digital number representing the pressure difference between the upper and lower left heart chambers. The device can thus measure the pressure difference across a natural or artificial nitral valve in any condition, for example, under obstructed flow such as is associated with rheumatic heart disease or the stenosis accompanying thrombus formation on artificial mitral heart valves.

The information used by this device derives from standard electrocardiographs 12d, thereby allowing a convenient and totally noninvasive assessment of mitral valve obstruction. Current diagnostic techniques depend upon cardiac catheterization, Doppler ultrasound studies, or direct visualization of the mitral valve orifice by bidimensional echocardiography. The proposed device could provide a convenient and inexpensive screening test for natural and prosthetic mitral valve misfunction.

5. Noninvasive Assessment of Aortic Valve Pressure Gradient

The classical Gorlin formula for aortic valve area is:

$$A = SV/(44.5\ t_s dP^2) \tag{5.1}$$

where A is the aortic valve area in $cm^2$, SV is the stroke volume in ml, $t_s$ is the systolic ejection period in seconds, and dP is the aortic valve pressure gradient in mm Hg.

In flow through a constricted region, the pressure drop is proportional to the degree of stenosis. For the case of the stenotic aortic valve, an approximate linear relation exists between the left ventricular pressure and the pressure gradient. This follows from the laws of hydrodynamics if the poststenotic pressure is independent of the pressure in the prestenotic space. Clinically, this principle is suggested by the observation that patients with aortic stenosis may have relatively normal aortic systolic and diastolic pressures and yet highly abnormal ventricular pressures. The detailed calculation in terms of energy loss across the aortic valve has been developed and published previously. Experimental confirmation of this relation is supported by the present study.

This analysis suggests that aortic valve pressure gradient may be expressed as a constant times the left ventricular pressure. Specifically, $dP=0.33\ P_v$, where dP is the aortic valve pressure gradient and $P_v$ is the left ventricular pressure. The value of the constant, 0.33, was determined from a linear regression of aortic valve gradient on left ventricular pressure. In this investigation the aortic valve gradient is expressed in accordance with this principle, and the results of previous studies relating wall stress with left ventricular pressure as:

$$P = K(W/D) \tag{5.2}$$

The value of the diastolic constant wall stress was found to be K=300 from a statistical analysis of end-diastolic ventricular wall thickness and dimension measurements associated with aortic valve pressure gradient. Combining eqs. (5.1) and (5.2) allows the derivation of a formula for aortic valve area:

$$A = SV(D/W)^{1/2}/(750t) \quad (5.3)$$

The patients included in this study were a series of 13 patients presenting for evaluation for possible aortic valvular disease via left and right heart catheterization. These procedures were conducted by the standard methods with all the parameters required for an evaluation of effective valve area by the Gorlin formula. Additionally M-mode echographic records of the left heart were obtained immediately prior to the catheterization study. These provided data required to compute left ventricular wall stress and relate this value to ventricular pressure.

A demonstration of the predictive capacity of the noninvasive pressure gradient and effective valve area expressions is shown in Table 21. The correspondence between the predictions of the new equation using pressure estimated by eq. (5.2) and the Gorlin formula from pressure measured by classical catheterization techniques is characterized by a correlation coefficient and standard error of r=0.95, SE=0.08, N=13.

Left ventricular pressures computed by eq. (5.2) using ventricular dimensions correspond to measured aortic valve gradients at a level given by a correlation coefficient of r=0.54 and a standard error of SE=16 mm Hg. An estimate of aortic valve gradient using eq. (5.2) is characterized by a correlation coefficient of r=0.85, N=13.

TABLE 21

Comparison of aortic valve pressure gradient and effective area computed by noninvasive methods with the results of classical cardiac catheterization.

| Case | Q | HF | SV | $P_v$ | $dP_c$ | W/D | $dP_s$ | t | $A_G$ | $A_n$ |
|---|---|---|---|---|---|---|---|---|---|---|
| 1 | 8.3 | 75 | 111 | 200 | 52 | .17 | 50 | .27 | 1.30 | 1.35 |
| 2 | 6.2 | 72 | 91 | 176 | 53 | .21 | 64 | .31 | 0.90 | 0.85 |
| 3 | 7.2 | 68 | 106 | 245 | 83 | .23 | 71 | .35 | 0.75 | 0.85 |
| 4 | 6.3 | 86 | 73 | 208 | 58 | .30 | 64 | .30 | 0.70 | 0.70 |
| 5 | 6.6 | 82 | 81 | 240 | 77 | .27 | 81 | .31 | 0.65 | 0.65 |
| 6 | 3.4 | 68 | 50 | 245 | 39 | .19 | 57 | .30 | 0.60 | 0.50 |
| 7 | 6.2 | 97 | 63 | 204 | 69 | .21 | 62 | .32 | 0.55 | 0.40 |
| 8 | 4.5 | 80 | 56 | 168 | 55 | .24 | 71 | .33 | 0.55 | 0.45 |
| 9 | 4.2 | 60 | 60 | 264 | 107 | .35 | 83 | .35 | 0.45 | 0.50 |
| 10 | 3.8 | 95 | 40 | 208 | 62 | .28 | 83 | .24 | 0.24 | 0.45 |
| 11 | 4.9 | 86 | 57 | 235 | 93 | .19 | 56 | .30 | 0.30 | 0.45 |
| 12 | 4.4 | 80 | 55 | 208 | 93 | .35 | 105 | .30 | 0.40 | 0.40 |
| 13 | 3.5 | 88 | 40 | 200 | 68 | .22 | 65 | .31 | 0.35 | 0.35 |
| Mean | | | | | 208 | | 70 | .24 | 0.62 | 0.61 |
| SE | | | | | | | | | | 0.08 |
| r | | | | | | | | | 0.85 | 0.95 |

Q = cardiac output from Fick principle method, HF = heart frequency, SV = stroke volume from catheterization (Q/HF), $dP_s$ = aortic valve pressure gradient at catheterization in mm Hg, W/D = ratio of the posterior wall thickness to the minor left ventricular dimension, t = systolic ejection period in sec, $A_G$ = aortic valve area in sq cm from the Gorlin formula, $A_n$ = aortic valve area from eq. (5.3), $dP_s$ = pressure gradient computed from wall stress measurements, SE = standard error of $A_n$ relative to $A_G$ and r = linear correlation coefficient.

Sample Aortic Valve Pressure Gradient Calculation

Figure 7:
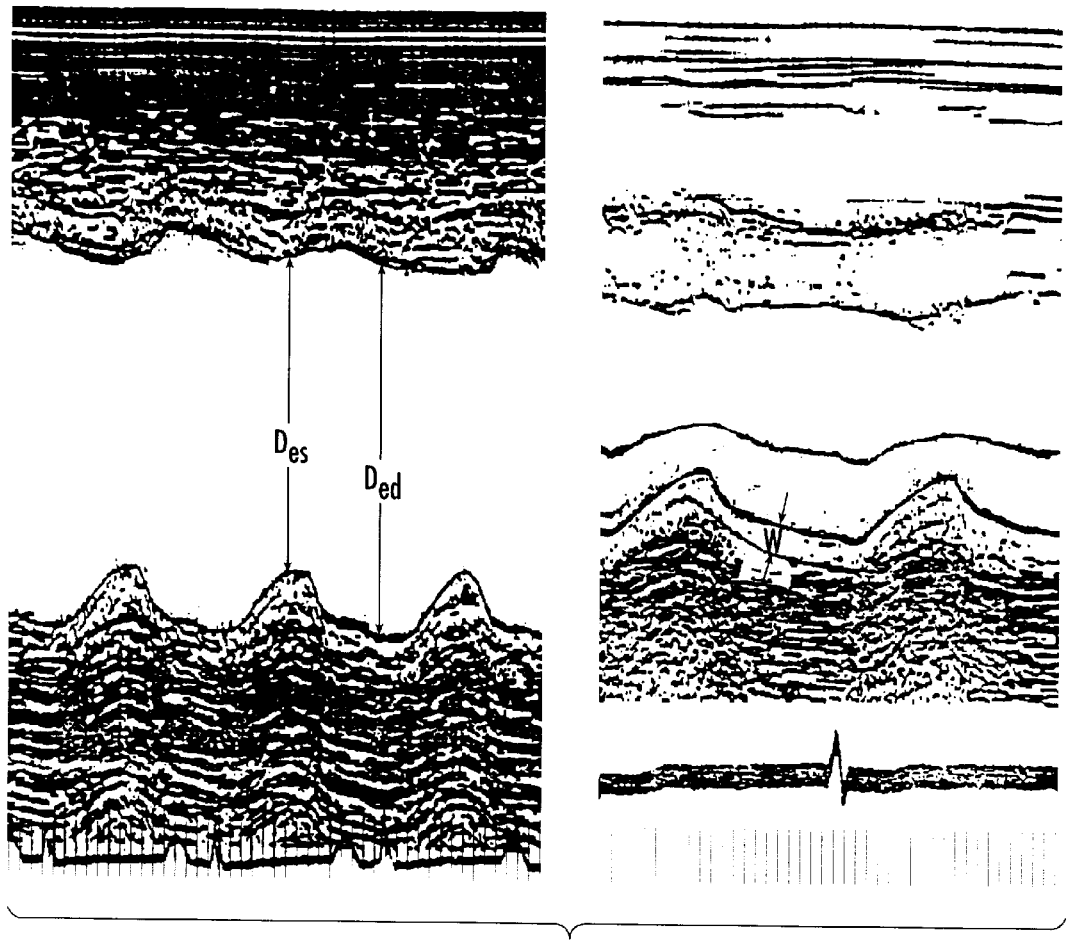
FIG. 7 is an M-mode echographic record indicating cardiac dimensions required for the aortic valve pressure calculation.

As an example of the use of eq. (4.2) and noninvasively obtained data to calculate aortic valve pressure, FIG. 7 shows an M-mode echocardiogram from which may be obtained values for W and D (here $D_{ed}$ is used). K is an empirically derived wall stress constant equal to 300 kPa.

If W/D=0.17 (Case 1 in Table 21), dPp=50 as predicted by the method of the present invention. For this case, $dP_c$ was found to be 52 from cardiac catheterization. A value <20 is considered normal.

6. Noninvasive Assessment of Mitral Valve Insufficiency

In this embodiment of the invention the principle of continuity is used in concert with the fundamental imbalance in forward and total stroke volume to develop several noninvasive methods for estimating regurgitant fraction in conditions of pure or mixed mitral insufficiency.

Theoretical Background

The fundamental expression relating forward and total stroke volume may be written as:

$$Sv_t = SV_f + Sv_r \quad (6.1)$$

where $SV_t$ is the total stroke volume, $SV_r$ is the regurgitant stroke volume, and $SV_f$ is the forward stroke volume. The regurgitant fraction may be defined as the ratio of regurgitant stroke volume to total stroke volume:

$$Rf = SV_r/(SV_r + Sv_f) \quad (6.2)$$

Thus eq. (6.1) may be written as:

$$Sv_t = SV_f + RfSV_t \quad (6.3)$$

Solving for Rf yields:

$$Rf = 1 - (SV_f/SV_t) \quad (6.4)$$

Application of the Equation of Continuity

Application of the continuity equation allows the application of Doppler ultrasound in combination with echography in several unique configurations. The equation of continuity is a mathematical expression of a fundamental law of physics, the conservation of mass. For an incompressible fluid such as blood, the flow into a portion of the vascular system must equal the flow exiting the same space if there is no blood-forming tissue in that region. In terms of vascular flow, this principle may be expressed by:

$$v_1 A_1 = v_2 A_2 \quad (6.5)$$

where $v_1$ and $v_2$ are blood velocities through cross-sectional areas $A_1$ and $A_2$, respectively. If the blood velocities and corresponding cross-sectional areas under consideration are the velocities and areas associated with the ascending aorta, mitral, and tricuspid valves, eq. (6.5) may be applied so as to estimate regurgitant fraction through eq. (6.4).

The product of velocity and cross-sectional area in eq. (6.5) represents a flow. If the product of cardiac valve or ascending aortic flow times the appropriate systolic or diastolic time interval is taken, a volume that can be identified with stroke volume is found. Using this concept the volume (V) of blood flowing through a particular cross-sectional area (A) may be expressed as:

$$V = vAt \quad (6.6)$$

where t is the duration of the flow. Considering flow across the mitral valve in the absence of a regurgitant lesion, left heart stroke volume may be expressed as:

$$Sv_l = v_m A_m t_d \quad (6.7)$$

where $SV_l$ is the left heart stroke volume, $v_m$ is the mean blood velocity across the mitral valve, $A_m$ is the diastolic mitral valve area, and $t_d$ is the diastolic filling period. Under the same conditions right heart stroke volume ($SV_r$) is given as:

$$Sv_r = v_t A_t t_d \quad (6.8)$$

where $v_t$ is the mean velocity across the tricuspid valve and $A_t$ is the diastolic tricuspid valve area.

Forward Stroke Volume

In the absence of aortic regurgitation, irrespective of the function of the mitral valve, forward stroke volume may be computed by eq. (6.1) as:

$$SV_f = v_a A_a t_s \qquad (6.9)$$

where $v_a$ is the mean blood velocity through $A_a$, a cross-sectional area in the ascending aorta, and $t_s$ is the systolic ejection time.

Total Stroke Volume

In mitral insufficiency the total stroke volume comprises a forward and regurgitant fraction. This volume is readily measured by the difference of end-diastolic volume with end-systolic volume. In terms of echographic and Doppler ultrasonic parameters, this is expressed as:

$$SV_t = V_{ed} - V_{es} \qquad (6.10)$$

$$SV_t = v_m A_m t_d \qquad (6.11)$$

$$SV_t = v_m A_m t_s + v_a A_a t_s \qquad (6.12)$$

where $V_{es}$ and $V_{ed}$ are the left ventricular end-systolic and diastolic volumes, respectively, and the remaining parameters are defined above.

Calculation of Rf from 2D Echocardiography Alone

Two-dimensional echocardiography allows direct geometric measurements of ventricular dimensions which permit calculation of Rf by eq. (6.4). In the absence of tricuspid regurgitation, the forward stroke volume may be taken as the right heart stroke volume. The total stroke volume may be expressed as the left ventricular stroke volume, which includes forward and regurgitant flow. Thus Rf is given as:

$$Rf = 1 - (SV_r/SV_l) \qquad (6.13)$$

where $SV_r$ and $SV_l$ are the right and left heart stroke volumes, respectively. These volumes may be derived from Simpson's rule of integration of the appropriate right and left ventricular dimensions or found by any of various ventricular volume formulas.

Application to Aortic and Mitral Valve Flow

The forward stroke volume across the cross-sectional area of the ascending aorta may be given as:

$$SV_f = v_a A_a t_s \qquad (6.14)$$

The total stroke volume is given by eq. (6.12) as:

$$SV_t = v_m A_m t_s + v_a A_a t_s \qquad (6.15)$$

Combining eqs. (6.12) and (6.9) with eq. (6.4) yields the regurgitant fraction as:

$$Rf = 1 - (v_a A_a t_s)/(v_m A_m t_d + v_a A_a t_s) \qquad (6.16)$$

Rf Derived from Aortic Root Flow and Left Heart Volumes

Expressing forward stroke volume in the ascending aorta by eq. (6.9):

$$SV_f = v_a A_a t_s \qquad (6.17)$$

and expressing total stroke volume as:

$$SV_t = V_{ed} - V_{es} \qquad (6.18)$$

where $V_{ed}$ and $V_{es}$ are the left heart end-diastolic and -systolic volumes, respectively. Equation (6.4) then gives:

$$Rf = 1 - (v_a A_a t_s)/(V_{ed} - V_{es}) \qquad (6.19)$$

Rf from Mitral and Tricuspid Valve Flow

In this case it is assumed that the tricuspid valve is competent. The forward and total stroke volume are expressed as:

$$SV_f = v_t A_t t_d \text{ and } SV_t = v_m A_m t_d \qquad (6.20)$$

The regurgitant fraction is thus given by eq. (6.4) as:

$$Rf = 1 - (v_t A_t)/(v_m A_m) \qquad (6.21)$$

where the valve areas are measured by 2D echography in diastole.

Rf Determined by Tricuspid and Mitral Valve Flow Combined with Aortic Root Flow In this case the right heart stroke volume may be expressed as:

$$SV_r = v_t A_t t_d \qquad (6.22)$$

The left heart stroke volume derives from aortic root flow and regurgitant mitral valve flow as:

$$SV_l = v_a A_a t_s + v_m A_m t_s \qquad (6.23)$$

where the symbols are as previously defined and $A_m$ is taken to be the systolic mitral valve area. Substituting these values into eq. (6.4) yields:

$$Rf = 1 - (v_t A_t t_d)/(v_a A_a t_s + v_m A_m t_s) \qquad (6.24)$$

Estimation of Rf by Doppler Ultrasound and 2D and M-Mode Eclography

In this case the diastolic mitral valve area is measured by 2D echography and measure the diameter of the ascending aorta by M-mode echography. Assuming a circular aortic cross-sectional area, the area may be found from the diameter. The regurgitant fraction is then given as:

$$Rf = 1 - (\pi v_a d^2 t_s)/(4 v_m A_m t_d) \qquad (6.25)$$

where d is the diameter of the ascending aorta.

Estimation of Rf Using Doppler Ultrasound and M-Mode Echography

If only Doppler and M-mode instruments are available, the diastolic mitral valve area may be found through application of a known echographic hydraulic orifice formula as:

$$A_m = 21 SV/T^2 \qquad (6.26)$$

where SV is the stroke volume as estimated by a known M-mode echographic volume formula and T is the diastolic filling interval in seconds per minute. This parameter also may be found from M-mode echographic measurements. Equation (6.4) thus yields:

$$Rf = 1 - (v_a A_a t_s T^2)/(21 SV \, v_m t_d) \qquad (6.27)$$

Discussion

The equation of continuity is applicable to all incompressible flow states and allows a unique specification of one of its four components when the other three can be measured. The formula for regurgitant fraction provides a fundamental definition of the degree of mitral insufficiency. The remaining parameters that are incorporated into the equation of continuity and the regurgitant fraction may be measured with varying degrees of accuracy. Echographic estimates of stroke volume by 2D echography have achieved correlations with angiographic and Fick principle methods at a level of up to r=0.96. Two-dimensional estimates of mitral valve area have been shown to correlate with determinations by the Gorlin formula at a level of r=0.90. Various workers have demonstrated that Doppler ultrasound can measure blood velocity through cardiac valves and blood vessels at clinically useful levels of accuracy. These studies suggest that the parameters required to measure regurgitant fraction can be computed in a noninvasive manner.

In conclusion, the present invention demonstrates eight potential methods for estimating the regurgitant fraction in mitral insufficiency.

Sample Mitral Valve Insufficiency Calculation

Using eqs. (6.4) and (6.27) and referring to the Doppler ultrasound tracing in FIG. 8, a case is given in which d=1.75, $V_a$=50, $t_s$=0.25, $t_d$=0.4, HF=75, $D_{ed}$=45, $D_{es}$=25, $v_m$=25, and A=3. Rf is then calculated to be 0.62. A value <0.01 is considered normal. $D_{ed}$ and $D_{es}$ are measured by direct optical or digital signal processing methods.

7. Noninvasive Assessment of Aortic Valve Insufficiency

Theoretical Background

The fundamental expression relating forward and total stroke volume may be written as:

$$SV_t = SV_r + SV_f \quad (7.1)$$

where $SV_t$ is the total stroke volume, $SV_r$ is the regurgitant stroke volume, and $SV_f$ is the forward stroke volume. The regurgitant fraction may be defined as the ratio of regurgitant stroke volume to total stroke volume:

$$Rf = SV_r/(SV_r + Sv_f) \quad (7.2)$$

Thus eq. (7.1) may be written as:

$$SV_t = SV_f + Rf\, Sv_t \quad (7.3)$$

Solving for Rf yields:

$$Rf = 1 - (Sv_f/SV_t) \quad (7.4)$$

Equation of Continuity

Application of the continuity equation allows us to apply Doppler ultrasound in combination with echography in several unique configurations.

The equation of continuity is a mathematical expression of a fundamental law of physics, the conservation of mass. For an incompressible fluid such as blood, the flow into a portion of the vascular system must equal the flow exiting the same space if there is no blood forming tissue in that region. In terms of vascular flow, this principle may be expressed by the equation:

$$v_1 A_1 = v_2 A_2 \quad (7.5)$$

where $v_1$ and $v_2$ are blood velocities through cross-sectional areas $A_1$ and $A_2$, respectively. If the blood velocities and corresponding cross-sectional areas under consideration are the velocities and areas associated with the ascending aorta, mitral, and tricuspid valves, we may apply eq. (7.5) so as to estimate regurgitant fraction through eq. (7.4).

The product of velocity and cross-sectional area in eq. (7.5) represents a flow. If the product of the cardiac valve or ascending aortic flow area times the appropriate systolic or diastolic time interval is taken, a volume that can be identified with stroke volume is found. Using this concept the volume (V) of blood flowing through a particular cross-sectional area (A) may be expressed as:

$$V = vAt \quad (7.6)$$

where t is the duration of the flow.

Left Heart Stroke Volume

Considering flow across the mitral valve in the absence of a regurgitant lesion, we may express left heart stroke volume as:

$$SV_l = v_a A_a t_s \quad (7.7)$$

where $SV_l$ is the left heart stroke volume, $v_a$ is the mean blood velocity across the mitral valve, $A_a$ is the systolic aortic valve area, and $t_s$ is the systolic ejection period. Under the same conditions right heart stroke volume ($SV_r$) is given as:

$$SV_r = v_t A_t t_d \quad (7.8)$$

where $v_t$ is the mean velocity across the tricuspid valve, $A_t$ is the diastolic tricuspid valve area, and $t_d$ is the diastolic filling period.

Forward Stroke Volume

In the absence of mitral regurgitation, irrespective of the function of the aortic valve, forward stroke volume may be computed by eq. (7.1) as:

$$SV_f = v_m A_m t_d \quad (7.9)$$

where $v_m$ is the mean blood velocity through $A_m$, a cross-sectional area of the mitral valve.

Total Stroke Volume

In aortic insufficiency the total stroke volume comprises a forward and regurgitant fraction. This volume is readily measured by the difference of end-diastolic volume with end-systolic volume. In terms of echographic and Doppler ultrasonic parameters, this is expressed as:

$$SV_t = V_{ed} - V_{es} \quad (7.10)$$

$$SV_t = v_m A_m t_d \quad (7.11)$$

$$SV_t = v_m A_m t_s + v_a A_a t_s \quad (7.12)$$

where $V_{es}$ and $V_{ed}$ are the left ventricular end-systolic and diastolic volumes, respectively, and the remaining parameters are defined above.

Calculation of Rf from 2D Echocardiography Alone

Two-dimensional echocardiography allows direct geometric measurements of ventricular dimensions, which permits the calculation of Rf by eq. (7.4). In the absence of tricuspid regurgitation, the forward stroke volume may be taken as the right heart stroke volume. The total stroke volume may be expressed as the left ventricular stroke volume, which includes forward and regurgitant flow. Thus Rf is given as:

$$Rf = 1 - (Sv_r/SV_l) \quad (7.13)$$

where $SV_r$ and $SV_l$ are the right and left heart stroke volumes, respectively. These volumes may be derived from Simpson's rule of integration of the appropriate right and left ventricular dimensions or found by any of various ventricular volume formulas.

Rf Derived from Aortic and Mitral Valve Flow

The forward stroke volume across the cross-sectional area of the ascending aorta may be given as:

$$SV_f = v_a A_a t_s \quad (7.14)$$

The total stroke volume is given by eq. (7.12) as:

$$SV_t = v_m A_m t_s + v_a A_a t_s \quad (7.15)$$

Combining eqs. (7.12) and (7.9) with eq. (7.4) yields the regurgitant fraction as:

$$Rf = 1 - (v_a A_a t_s)/(v_m A_m t_s + v_a A_a t_s) \quad (7.16)$$

Rf Derived from Mitral Valve Flow and Left Heart Volumes

Expressing forward stroke volume in the ascending aorta by eq. (7.9):

$$SV_f = v_m A_m t_d \quad (7.17)$$

and expressing total stroke volume as:

$$SV_t = V_{ed} - V_{es} \quad (7.18)$$

where $V_{ed}$ and $V_{es}$ are the left heart end-diastolic and -systolic volumes, respectively. Equation (7.4) then gives:

$$Rf = 1 - (v_m A_m t_d)/(V_{ed} - V_{es}) \quad (7.19)$$

Rf from Aortic and Mitral Valve Flow

In this case it is assumed that the tricuspid valve is competent. The forward and total stroke volume may be expressed as:

$$SV_f = v_t A_t t_d \text{ and } SV_t = v_a A_a t_s \quad (7.20)$$

The regurgitant fraction is thus given by eq. (7.4) as:

$$Rf = 1 - t_d v_t A_a / ts(v_a A_s + v_m A_m) \quad (7.21)$$

where the valve areas are measured by 2D echography in diastole.

Rf Determined by Mitral and Aortic Valve Flow Combined with Aortic Root Flow

In this case the forward stroke volume may be expressed as:

$$SV_f = v_m A_m t_d \quad (7.22)$$

The left heart stroke volume derives from aortic root flow and regurgitant aortic valve flow as:

$$SV_f = v_a A_a t_s + v_m A_m t_s = Sv_t \quad (7.23)$$

where the symbols are as previously defined and $A_m$ is taken to be the systolic mitral valve area. Substituting these values into eq. (7.4) yields:

$$Rf = 1 - (v_m A_m t_d)/(v_a A_a t_s + v_m A_m t_s) \quad (7.24)$$

Estimation of Rf by Doppler Ultrasound and 2D and M-Mode Echography

Here the area is determined by 2D echography and the diameter of the ascending aorta by M-mode echography. Assuming a circular aortic cross-sectional area, the area may be found from the diameter. The regurgitant fraction is then given as:

$$Rf = (4 v_m A_m t_d)/(\pi v_a d^2 t_s) \quad (7.25)$$

where d is the diameter of the ascending aorta.

Estimation of Rf Using Doppler Ultrasound and M-Mode Echography

If only Doppler and M-mode instruments are available, the diastolic mitral valve area may be found through application of an echographic hydraulic orifice formula as:

$$A_a = 7 SV/T^2 \quad (7.26)$$

where SV is the stroke volume as estimated by an M-mode echographic volume formula and T is the systolic ejection interval in seconds per minute. This parameter also may be found from M-mode echographic measurements. Equation (7.4) thus yields:

$$Rf = 1 - (7 v_a)/T^2 \quad (7.27)$$

Sample Aortic Valve Insufficiency Calculation

With the use of eqs. (7.4) and (7.7) and the equation for stroke volume:

$$Rf = 1 - \pi (d_a/2)^2 t_a v_a / 0.01 (D_{ed}^{12/5} - D_{es}^{12/5}) \quad (7.28)$$

Taking a case in which $D_a = 1.7$, $v_a = 50$, $D_{es} = 43$, $D_{ed} = 59$, $s_t = 0.25$, and $SV_t = 85$, Rf is calculated to be 0.33. A value <0.01 is considered normal.

Discussion

The formula for regurgitant fraction provides that the equation of continuity is applicable to all incompressible fundamental definition of the degree of aortic insufficiency. The remaining parameters that are incorporated into the equation of continuity and the regurgitant fraction may be measured with varying degrees of accuracy. Echographic estimates of stroke volume by 2D echography have achieved correlations with angiographic and Fick principle methods at a level of up to r=0.96. M-mode echographic estimates of aortic valve area have been shown to correlate with determinations by the Gorlin formula at a level of r=0.85. Various workers have demonstrated that Doppler ultrasound can measure blood velocity through cardiac valves and blood vessels at clinical useful levels of accuracy. These studies suggest that the parameters required to measure regurgitant fraction can be computed in a noninvasive manner. In conclusion, the present invention comprises eight methods for estimating the regurgitant fraction in aortic insufficiency.

It may be appreciated by one skilled in the art that additional embodiments may be contemplated, including related methods and devices for noninvasively measuring additional cardiovascular parameters.

In the foregoing description, certain terms have been used for brevity, clarity, and understanding, but no unnecessary limitations are to be implied therefrom beyond the requirements of the prior art, because such words are used for description purposes herein and are intended to be broadly construed. Moreover, the embodiments of the apparatus illustrated and described herein are by way of example, and the scope of the invention is not limited to the exact details of construction.

Having now described the invention, the construction, the operation and use of preferred embodiment thereof, and the advantageous new and useful results obtained thereby, the new and useful constructions, and reasonable mechanical equivalents thereof obvious to those skilled in the art, are set forth in the appended claims.

What is claimed is:

1. A noninvasive method for measuring an area of a cardiac valve of a patient comprising the steps of:

noninvasively measuring a plurality of mechanical cardiac parameters of the patient, including a heart rate, a stroke volume, and a time period between an empty state and a filled state of a cardiac chamber; and calculating a cardiac valve area with the use of the measured cardiac parameters.

2. The method recited in claim 1, wherein the stroke volume measuring step comprises:

collecting an echocardiogram;

measuring from the echocardiogram an end diastolic dimension and an end systolic dimension; and calculating the stroke volume from the end diastolic dimension and the end systolic dimension.

3. The method recited in claim 2, wherein the stroke volume calculating step comprises utilizing a formula:

$$SV=0.01(D_{ed}^{12/5}-D_{es}^{12/5})$$

where SV is the stroke volume, $D_{ed}$ is the end-diastolic dimension, and $D_{es}$ is the end-systolic dimension.

4. The method recited in claim 1, wherein:
   the measuring step further comprises measuring a diastolic filling period of the patient; and
   the calculating step comprises calculating a mitral valve area.

5. The method recited in claim 4, wherein the diastolic filling period measuring step comprises taking a phonocardiogram and calculating the diastolic filling period therefrom.

6. The method recited in claim 5, wherein the diastolic filling period calculating step comprises measuring an OS-I interval from the phonocardiogram.

7. The method recited in claim 6, wherein the heart rate measuring step comprises calculating a reciprocal of an I—I interval from the phonocardiogram.

8. The method recited in claim 4, wherein the mitral valve area calculating step comprises utilizing a formula:

$$A=21\ SV/(Rt)^2$$

where A is the mitral valve area, SV is the stroke volume, R is the heart rate, and t is the diastolic filling period.

9. The method recited in claim 1, wherein:
   the measuring step further comprises measuring a systolic ejection period of the patient; and
   the calculating step comprises calculating an aortic valve area.

10. The method recited in claim 9, wherein the systolic ejection period measuring step comprises taking a phonocardiogram and calculating the systolic ejection period therefrom.

11. The method recited in claim 10, wherein the systolic ejection period calculating step comprises measuring an ES-II interval in the phonocardiogram.

12. The method recited in claim 11, wherein the heart rate measuring step comprises calculating a reciprocal of an I—I interval from the phonocardiogram.

13. The method recited in claim 11, wherein the heart rate measuring step comprises taking an electrocardiogram and measuring an R—R interval therein to obtain the heart rate.

14. The method recited in claim 9, wherein the aortic valve area calculating step comprises utilizing a formula:

$$A=7\ SV/(Rt_s)^2$$

where A is the aortic valve area, SV is the stroke volume, R is the heart rate, and $t_s$ is the systolic ejection time.

15. A device for noninvasively measuring an area of a cardiac valve of a patient comprising:
   means for noninvasively measuring a plurality of mechanical cardiac parameters of the patient, including a heart rate, a stroke volume, and a time period between an empty state and a filled state of a cardiac chamber; and
   means for calculating a cardiac valve area with the use of the measured cardiac parameters.

16. The device recited in claim 15, wherein the stroke volume measuring means comprises:
   an echocardiograph;
   means for measuring from an echocardiogram taken with the electrocardiograph an end diastolic dimension and an end systolic dimension; and
   means for calculating the stroke volume from the end diastolic dimension and the end systolic dimension.

17. The device recited in claim 16, wherein the stroke volume calculating means comprises a processor and software resident therein having means for utilizing a formula:

$$SV=0.01(D_{ed}^{12/5}-D_{es}^{12/5})$$

where SV is the stroke volume, $D_{ed}$ is the end-diastolic dimension, and $D_{es}$ is the end-systolic dimension.

18. The device recited in claim 15, wherein:
   the means for measuring further comprises means for measuring a diastolic filling period of the patient; and
   the calculating means comprises means for calculating a mitral valve area.

19. The device recited in claim 18, wherein the diastolic filling period measuring means comprises a phonocardiograph and means for calculating the diastolic filling period from a phonocardiogram taken by the phonocardiograph.

20. The device recited in claim 19, wherein the diastolic filling period calculating means comprises means for measuring an OS-I interval from the phonocardiogram.

21. The device recited in claim 20, wherein the heart rate measuring means comprises means for calculating a reciprocal of an I—I interval from the phonocardiogram.

22. The device recited in claim 18, wherein the mitral valve area calculating means comprises a processor and software resident therein having means for utilizing a formula:

$$A=21\ SV/(Rt)^2$$

where A is the mitral valve area, SV is the stroke volume, R is the heart rate, and t is the diastolic filling period.

23. The device recited in claim 15, wherein:
   the measuring means further comprises means for measuring a systolic ejection period of the patient; and
   the calculating means comprises means for calculating an aortic valve area.

24. The device recited in claim 23, wherein the systolic ejection period measuring means comprises a phonocardiograph for taking a phonocariogram and means for calculating the systolic ejection period therefrom.

25. The device recited in claim 24, wherein the systolic ejection period calculating means comprises means for measuring an ES-II interval in the phonocardiogram.

26. The device recited in claim 25, wherein the heart rate measuring means comprises means for calculating a reciprocal of an I—I interval from the phonocardiogram.

27. The device recited in claim 25, wherein the heart rate measuring means comprises taking an electrocardiograph for taking an electrocardiogram and means for measuring an R—R interval therein to obtain the heart rate.

28. The device recited in claim 23, wherein the aortic valve area calculating means comprises a processor and software resident therein having means for utilizing a formula:

$$A=7\ SV/(Rt_s)^2$$

where A is the aortic valve area, SV is the stroke volume, R is the heart rate, and $t_s$ is the systolic ejection time.

29. A noninvasive method for measuring a cardiac left ventricular stroke volume of a patient comprising the steps of:
   collecting a cardiac echocardiogram from a patient;
   noninvasively measuring an end-diastolic dimension and an end-systolic dimension of a left ventricle from the echocardiogram; and calculating the stroke volume from the end-diastolic dimension and the end-systolic dimension.

30. The method recited in claim 29, wherein the stroke volume calculating step comprises utilizing a formula:

$$SV=0.01(D_{ed}^{12/5}-D_{es}^{12/5})$$

where SV is the stroke volume, $D_{ed}$ is the end-diastolic dimension, and $D_{es}$ is the end-systolic dimension.

31. A device for noninvasively measuring a cardiac left ventricular stroke volume of a patient comprising the steps of:

means for collecting a cardiac echocardiogram from a patient;

means for noninvasively measuring an end-diastolic dimension and an end-systolic dimension of a left ventricle from the echocardiogram; and means for calculating the stroke volume from the end-diastolic dimension and the end-systolic dimension.

32. The device recited in claim 31, wherein the stroke volume calculating means comprises a processor and software resident therein having means for utilizing a formula:

$$SV=0.01(D_{ed}^{12/5}-D_{es}^{12/5})$$

where SV is the stroke volume, $D_{ed}$ is the end-diastolic dimension, and $D_{es}$ is the end-systolic dimension.

33. A noninvasive method for calculating a mitral valve pressure gradient of a patient, comprising the steps of:

noninvasively measuring a heart rate of the patient;

noninvasively measuring a left ventricular diastolic filling period of the patient; and calculating the mitral valve pressure gradient from the heart rate and the diastolic filling period.

34. The method recited in claim 33, wherein the measuring steps comprise taking a phonocardiogram and obtaining the heart rate and diastolic filling period therefrom, the heart rate taken from an inverse of an I—I interval and the diastolic filling period taken from an OP-I interval.

35. The method recited in claim 33, wherein the calculating step comprises utilizing a formula:

$$dP=2.25\times10^{-6}R^4 t_d^2$$

where dP is the pressure gradient, R is the heart rate, and $t_d$ is the diastolic filling period.

36. A device for noninvasively determining a mitral valve pressure gradient of a patient, comprising the steps of:

means for noninvasively measuring a heart rate of the patient;

means for noninvasively measuring a left ventricular diastolic filling period of the patient; and means for calculating the mitral valve pressure gradient from the heart rate and the diastolic filling period.

37. The device recited in claim 36, wherein the measuring means comprise a phonocardiograph for taking a phonocardiogram and means for obtaining the heart rate and diastolic filling period therefrom, the heart rate taken from an inverse of an I—I interval and the diastolic filling period taken from an OP-I interval.

38. The device recited in claim 36, wherein the calculating means comprises a processor and software resident therein having means for utilizing a formula:

$$dP=2.25\times10^{-6}R^4 t_d^2$$

where dP is the pressure gradient, R is the heart rate, and $t_d$ is the diastolic filling period.

39. A noninvasive method of measuring an aortic valve pressure gradient of a patient comprising the steps of:

noninvasively measuring a left ventricular wall thickness of the patient;

noninvasively measuring a left ventricular end-diastolic dimension of the patient; and calculating the aortic valve pressure gradient from the measured wall thickness and the end-diastolic dimension.

40. The method recited in claim 39, wherein the measuring steps comprise taking an echocardiogram and obtaining values for the wall thickness and the end-diastolic dimension therefrom.

41. The method recited in claim 40, wherein the calculating step comprises utilizing a formula:

$$dP=KW/D_{ed}$$

where dP is the pressure gradient, K is an empirically derived wall stress constant equal to 300 kPa, W is the wall thickness, and $D_{ed}$ is the end-diastolic dimension.

42. A device for noninvasively measuring an aortic valve pressure gradient of a patient comprising:

means for noninvasively measuring a left ventricular wall thickness of the patient;

means for noninvasively measuring a left ventricular end-diastolic dimension of the patient; and means for calculating the aortic valve pressure gradient from the measured wall thickness and the end-diastolic dimension.

43. The device recited in claim 42, wherein the measuring means comprise an echocardiograph for taking an echocardiogram and means for obtaining values for the wall thickness and the end-diastolic dimension therefrom.

44. The device recited in claim 43, wherein the calculating means comprises a processor and software resident therein having means for utilizing a formula:

$$dP=KW/D_{ed}$$

where dP is the pressure gradient, K is an empirically derived wall stress constant equal to 300 kPa, W is the wall thickness, and $D_{ed}$ is the end-diastolic dimension.

* * * * *